United States Patent
Kohm

(10) Patent No.: US 8,568,461 B2
(45) Date of Patent: Oct. 29, 2013

(54) PERCUTANEOUS SPINAL IMPLANTS AND METHODS

(75) Inventor: Andrew C. Kohm, San Mateo, CA (US)

(73) Assignee: Warsaw Orothpedic, Inc., Warsaw, IN (US)

( * ) Notice: Subject to any disclaimer, the term of this patent is extended or adjusted under 35 U.S.C. 154(b) by 954 days.

(21) Appl. No.: 12/127,215

(22) Filed: May 27, 2008

(65) Prior Publication Data
US 2008/0288072 A1 Nov. 20, 2008

Related U.S. Application Data

(63) Continuation-in-part of application No. 11/752,981, filed on May 24, 2007, which is a continuation-in-part of application No. 11/356,302, filed on Feb. 17, 2006, now Pat. No. 7,988,709, which is a continuation-in-part of application No. 11/252,880, filed on Oct. 19, 2005, now abandoned, which is a continuation-in-part of application No. 11/059,526, filed on Feb. 17, 2005, now abandoned, application No. 12/127,215, which is a continuation-in-part of application No. 11/356,301, filed on Feb. 17, 2006, now Pat. No. 8,057,513, and a continuation-in-part of application No. 11/252,879, filed on Oct. 19, 2005, now Pat. No. 8,038,698, application No. 12/127,215, which is a continuation-in-part of application No. 11/693,496, filed on Mar. 29, 2007, now Pat. No. 8,096,994, which is a continuation-in-part of application No. 11/454,153, filed on Jun. 16, 2006, now Pat. No. 7,993,342, which is a continuation-in-part of application No. PCT/US2006/005580, filed on Feb. 17, 2006.

(60) Provisional application No. 60/695,836, filed on Jul. 1, 2005.

(51) Int. Cl.
A61B 17/88 (2006.01)
A61B 17/70 (2006.01)
A61F 2/44 (2006.01)

(52) U.S. Cl.
USPC ........ 606/279; 606/246; 606/248; 623/17.11; 623/17.16

(58) Field of Classification Search
USPC ............. 606/246, 248, 279; 623/17.11–17.16
See application file for complete search history.

(56) References Cited

U.S. PATENT DOCUMENTS

2001/0016743 A1 8/2001 Zucherman et al.
2001/0051822 A1* 12/2001 Stack et al. ................. 623/1.11

(Continued)

FOREIGN PATENT DOCUMENTS

EP 1982664 A 10/2008

*Primary Examiner* — Andrew Iwamaye
*Assistant Examiner* — Leslie Coburn

(57) ABSTRACT

Medical devices and related methods for the treatment of spinal conditions are described herein. In one embodiment, a method includes disposing at least a portion of a support member into a space between adjacent spinous processes. The support member defines a lumen between a proximal end and a distal end of the support member. An expandable member is inserted through the lumen of the support member such that a distal end portion of the expandable member is disposed outside a distal end of the lumen and a proximal end portion of the expandable member is disposed outside a proximal end of the lumen. The distal end portion and the proximal end portion of the expandable member are then expanded such that each of the distal end portion and the proximal end portion of the expandable member has an outer diameter greater than an outer diameter of the support member.

10 Claims, 45 Drawing Sheets

(56) References Cited

U.S. PATENT DOCUMENTS

| | | | |
|---|---|---|---|
| 2005/0056292 A1* | 3/2005 | Cooper | 128/898 |
| 2006/0085069 A1* | 4/2006 | Kim | 623/17.11 |
| 2007/0225807 A1 | 9/2007 | Phan et al. | |
| 2007/0276493 A1 | 11/2007 | Malandain et al. | |
| 2008/0058934 A1 | 3/2008 | Malandain et al. | |
| 2008/0262617 A1 | 10/2008 | Froehlich et al. | |

* cited by examiner

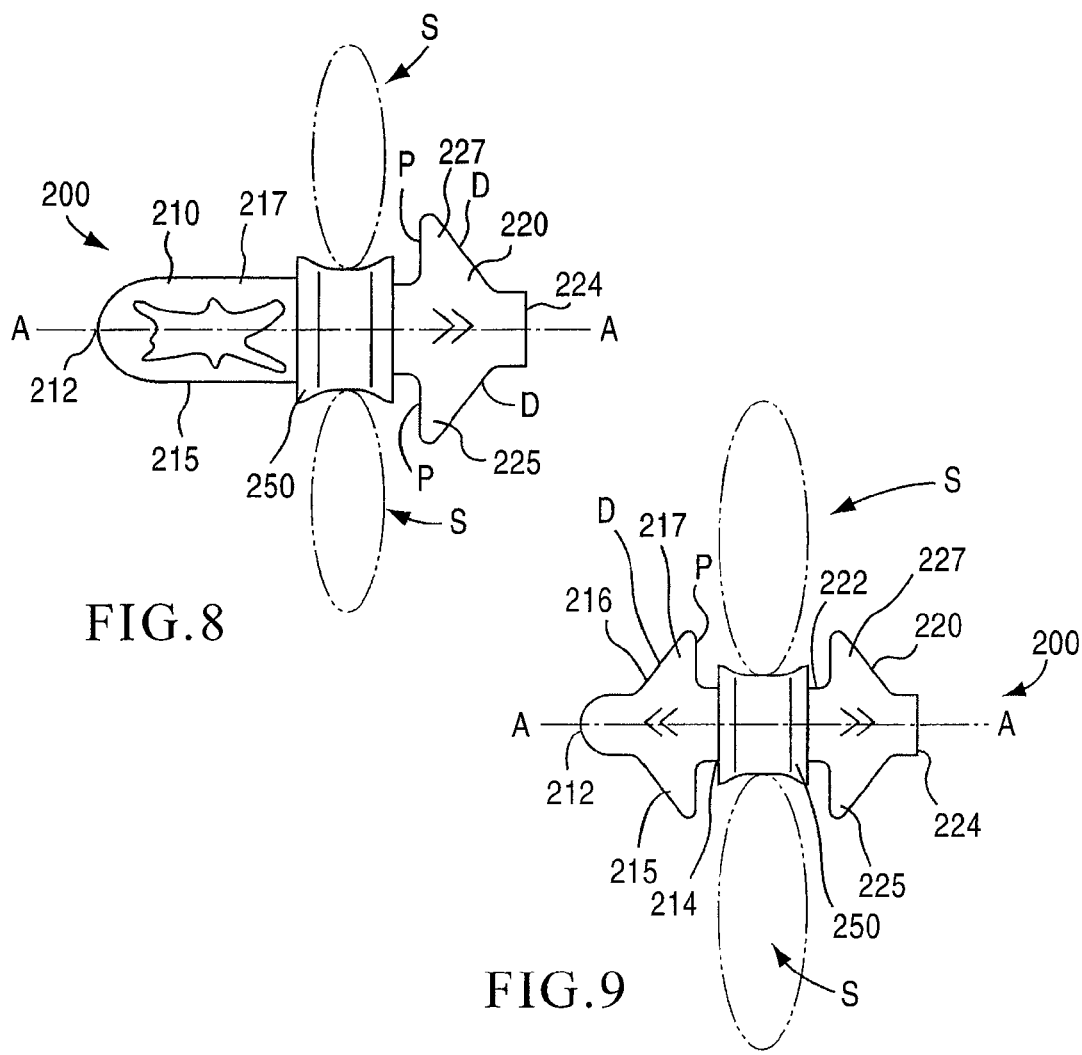
FIG.8
FIG.9
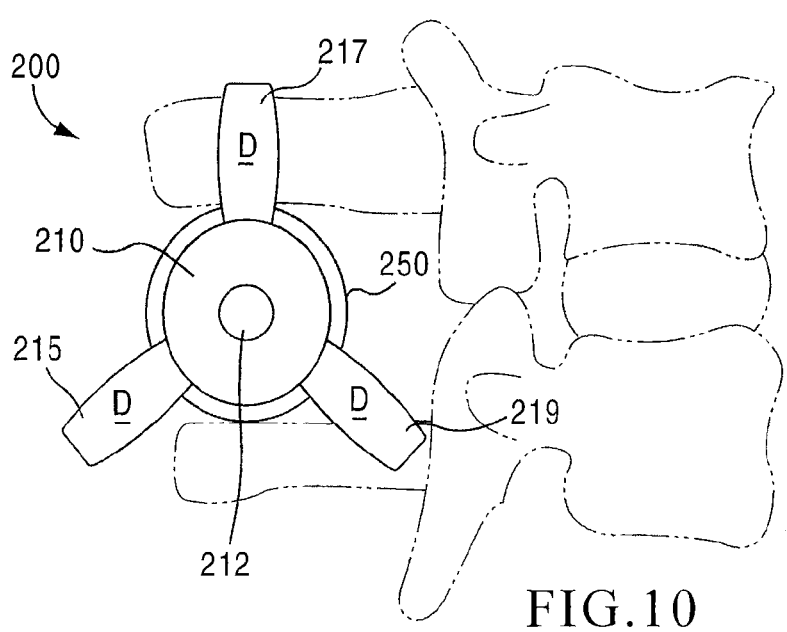
FIG.10

PERCUTANEOUS SPINAL IMPLANTS AND METHODS

CROSS-REFERENCE TO RELATED APPLICATIONS

This application claims priority to and is a continuation-in-part of U.S. patent application Ser. No. 11/752,981, entitled "Percutaneous Spinal Implants and Methods," filed May 24, 2007, which is a continuation-in-part of U.S. patent application Ser. No. 11/356,302, entitled "Percutaneous Spinal Implants and Methods," filed Feb. 17, 2006 now U.S. Pat. No. 7,988,709, which claims priority to U.S. Provisional Application Ser. No. 60/695,836, entitled "Percutaneous Spinal Implants and Methods," filed Jul. 1, 2005, and which is a continuation-in-part of U.S. patent application Ser. No. 11/252,880, entitled "Percutaneous Spinal Implants and Methods," filed Oct. 19, 2005 now abandoned, which is a continuation-in-part of U.S. patent application Ser. No. 11/059,526, entitled "Apparatus and Method for Treatment of Spinal Conditions," filed Feb. 17, 2005 now abandoned, and which claims priority to U.S. Provisional Application Ser. No. 60/695,836, entitled "Percutaneous Spinal Implants and Methods," filed Jul. 1, 2005. Each of the above-identified applications is incorporated herein by reference in its entirety.

This application also claims priority to and is a continuation-in-part of U.S. patent application Ser. No. 11/356,301, entitled "Percutaneous Spinal Implants and Methods," filed Feb. 17, 2006 now U.S. Pat. No. 8,057,513, which claims priority to U.S. Provisional Application Ser. No. 60/695,836, entitled "Percutaneous Spinal Implants and Methods," filed Jul. 1, 2005, and which is a continuation-in-part of U.S. patent application Ser. Nos. 11/252,879 and 11/252,880, each entitled "Percutaneous Spinal Implants and Methods," and filed October 19 now U.S. Pat. No. 8,038,698, each of which is a continuation-in-part of U.S. patent application Ser. No. 11/059,526, entitled "Apparatus and Method for Treatment of Spinal Conditions," filed Feb. 17, 2005 now abandoned. Each of the above-identified applications is incorporated herein by reference in its entirety.

This application also claims priority to and is a continuation-in-part of U.S. patent application Ser. No. 11/693,496 entitled "Percutaneous Spinal Implants and Methods," filed Mar. 29, 2007 now U.S. Pat. No. 8,096,994, which is a continuation-in-part of U.S. patent application Ser. No. 11/454,153, entitled "Percutaneous Spinal Implants and Methods," filed Jun. 16, 2006 now U.S. Pat. No. 7,993,342, which is a continuation-in-part of International Patent Application No. PCT/US2006/005580, entitled "Percutaneous Spinal Implants and Methods," filed Feb. 17, 2006, and which is a continuation-in-part of U.S. patent application Ser. No. 11/059,526, entitled "Apparatus and Method for Treatment of Spinal Conditions," filed Feb. 17, 2005 now abandoned, and which is a continuation-in-part of U.S. patent application Ser. No. 11/252,879, entitled "Percutaneous Spinal Implants and Methods," filed Oct. 19, 2005 now U.S. Pat. No. 8,038,698, which claims priority to U.S. Provisional Application Ser. No. 60/695,836, entitled "Percutaneous Spinal Implants and Methods," filed Jul. 1, 2005, and which is a continuation-in-part of U.S. patent application Ser. No. 11/252,880, entitled "Percutaneous Spinal Implants and Methods," filed Oct. 19, 2005, which claims priority to U.S. Provisional Application Ser. No. 60/695,836, entitled "Percutaneous Spinal Implants and Methods," filed Jul. 1, 2005. Each of the above-identified applications is incorporated herein by reference in its entirety.

This application also claims priority to and is a continuation-in-part of U.S. patent application Ser. No. 11/693,496, entitled "Percutaneous Spinal Implants and Methods," filed Mar. 29, 2007 now U.S. Pat. No. 8,096,994, which claims priority to and is a continuation-in-part of U.S. patent application Ser. No. 11/454,153, entitled "Apparatus and Method for Treatment of Spinal Conditions," filed Jun. 16, 2006 now U.S. Pat. No. 7,993,342, which is a continuation-in-part of International Patent Application No. PCT/US2006/005580, entitled "Percutaneous Spinal Implants and Methods," filed Feb. 17, 2006, and which is a continuation-in-part of U.S. patent application Ser. No. 11/059,526, entitled "Apparatus and Method for Treatment of Spinal Conditions," filed Feb. 17, 2005 now abandoned, and which is a continuation-in-part of U.S. patent application Ser. No. 11/252,879, entitled "Percutaneous Spinal Implants and Methods," filed Oct. 19, 2005 now U.S. Pat. No. 8,038,698, which claims priority to U.S. Provisional Application Ser. No. 60/695,836, entitled "Percutaneous Spinal Implants and Methods," filed Jul. 1, 2005, and which is a continuation-in-part of U.S. patent application Ser. No. 11/252,880, entitled "Percutaneous Spinal Implants and Methods," filed Oct. 19, 2005, which claims priority to U.S. Provisional Application Ser. No. 60/695,836, entitled "Percutaneous Spinal Implants and Methods," filed Jul. 1, 2005; each of which is incorporated herein by reference in its entirety.

This application also claims priority to and is a continuation-in-part of International Patent Application No. PCT/US2006/005580, entitled "Percutaneous Spinal Implants and Methods," filed Feb. 17, 2006, which claims priority to and is a continuation-in-part of U.S. patent application Ser. No. 11/059,526, entitled "Apparatus and Method for Treatment of Spinal Conditions," filed Feb. 17, 2005 now abandoned; U.S. Provisional Application Ser. No. 60/695,836 entitled "Percutaneous Spinal Implants and Methods," filed Jul. 1, 2005; U.S. patent application Ser. No. 11/252,879, entitled "Percutaneous Spinal Implants and Methods," filed Oct. 19, 2005 now U.S. Pat. No. 8,038,698; and U.S. patent application Ser. No. 11/252,880, entitled "Percutaneous Spinal Implants and Methods," filed Oct. 19, 2005 now abandoned, the entire disclosures of which are hereby incorporated by reference.

This application also claims priority to and is a continuation-in-part of U.S. patent application Ser. No. 11/356,301, entitled "Percutaneous Spinal Implants and Methods," filed Feb. 17, 2006 now U.S. Pat. No. 8,057,513, which is a continuation-in-part of U.S. patent application Ser. No. 11/252,879, entitled "Percutaneous Spinal Implants and Methods," filed Oct. 19, 2005 now U.S. Pat. No. 8,038,698; and U.S. patent application Ser. No. 11/252,880, entitled "Percutaneous Spinal Implants and Methods," filed Oct. 19, 2005 now abandoned, each of which is a continuation-in-part of U.S. patent application Ser. No. 11/059,526, entitled "Apparatus and Method for Treatment of Spinal Conditions," filed Feb. 17, 2005 now abandoned, each of which are incorporated herein by reference in its entirety. This application also claims the benefit of U.S. Provisional Application Ser. No. 60/695,836 entitled "Percutaneous Spinal Implants and Methods," filed Jul. 1, 2005, which is incorporated herein by reference in its entirety.

This application is related to U.S. patent application Ser. No. 11/752,984, entitled "Percutaneous Spinal Implants and Methods," filed on May 24, 2007; U.S. patent application Ser. No. 11/752,982, entitled "Percutaneous Spinal Implants and Methods," filed on May 24, 2007; and U.S. patent application Ser. No. 11/752,983, entitled "Percutaneous Spinal Implants and Methods," filed on May 24, 2007, the entire disclosures of which are hereby incorporated by reference.

This application is also related to U.S. patent application Ser. No. 11/693,500, entitled "Percutaneous Spinal Implants and Methods," filed on Mar. 29, 2007; and U.S. patent application Ser. No. 11/693,502, entitled "Percutaneous Spinal Implants and Methods," filed on Mar. 29, 2007, the entire disclosures of which are hereby incorporated by reference.

This application is also related to U.S. patent application Ser. No. 12/127,213, entitled "Percutaneous Spinal Implants and Methods," filed on same date, the disclosure of which is hereby incorporated by reference in its entirety.

BACKGROUND

The invention relates generally to the treatment of spinal conditions, and more particularly, to the treatment of spinal compression using percutaneous spinal implants for implantation between adjacent spinous processes.

A back condition that impacts many individuals is spinal stenosis. Spinal stenosis is a progressive narrowing of the spinal canal that causes compression of the spinal cord. Each vertebra in the spinal column has an opening that extends through it. The openings are aligned vertically to form the spinal canal. The spinal cord runs through the spinal canal. As the spinal canal narrows, the spinal cord and nerve roots extending from the spinal cord and between adjacent vertebrae are compressed and may become inflamed. Spinal stenosis can cause pain, weakness, numbness, burning sensations, tingling, and in particularly severe cases, may cause loss of bladder or bowel function, or paralysis. The legs, calves and buttocks are most commonly affected by spinal stenosis, however, the shoulders and arms may also be affected.

Mild cases of spinal stenosis may be treated with rest or restricted activity, non-steroidal anti-inflammatory drugs (e.g., aspirin), corticosteroid injections (epidural steroids), and/or physical therapy. Some patients find that bending forward, sitting or lying down may help relieve the pain. This may be due to bending forward creates more vertebral space, which may temporarily relieve nerve compression. Because spinal stenosis is a progressive disease, the source of pressure may have to be surgically corrected (decompressive laminectomy) as the patient has increasing pain. The surgical procedure can remove bone and other tissues that have impinged upon the spinal canal or put pressure on the spinal cord. Two adjacent vertebrae may also be fused during the surgical procedure to prevent an area of instability, improper alignment or slippage, such as that caused by spondylolisthesis. Surgical decompression can relieve pressure on the spinal cord or spinal nerve by widening the spinal canal to create more space. This procedure requires that the patient be given a general anesthesia as an incision is made in the patient to access the spine to remove the areas that are contributing to the pressure. This procedure, however, may result in blood loss and an increased chance of significant complications, and usually results in an extended hospital stay.

Minimally-invasive procedures have been developed to provide access to the space between adjacent spinous processes such that major surgery is not required. Such known procedures, however, may not be suitable in conditions where the spinous processes are severely compressed. Moreover, such procedures typically involve large or multiple incisions.

Thus, a need exists for improvements in the treatment of spinal conditions such as spinal stenosis.

SUMMARY OF THE INVENTION

Medical devices and related methods for the treatment of spinal conditions are described herein. In one embodiment, a method includes disposing at least a portion of a support member into a space between adjacent spinous processes. The support member defines a lumen between a proximal end and a distal end of the support member. An expandable member is inserted through the lumen of the support member such that a distal end portion of the expandable member is disposed outside a distal end of the lumen and a proximal end portion of the expandable member is disposed outside a proximal end of the lumen. The distal end portion and the proximal end portion of the expandable member are then expanded such that each of the distal end portion and the proximal end portion of the expandable member has an outer diameter greater than an outer diameter of the support member.

BRIEF DESCRIPTION OF THE DRAWINGS

FIG. 8 is a posterior view of a medical device according to an embodiment of the invention, a portion of which is in a second configuration.

FIG. 9 is a posterior view of the medical device illustrated in FIG. 7 fully deployed in the second configuration.

FIG. 10 is a front plan view of the medical device illustrated in FIG. 7 in the second configuration.

DETAILED DESCRIPTION

Figure 1:
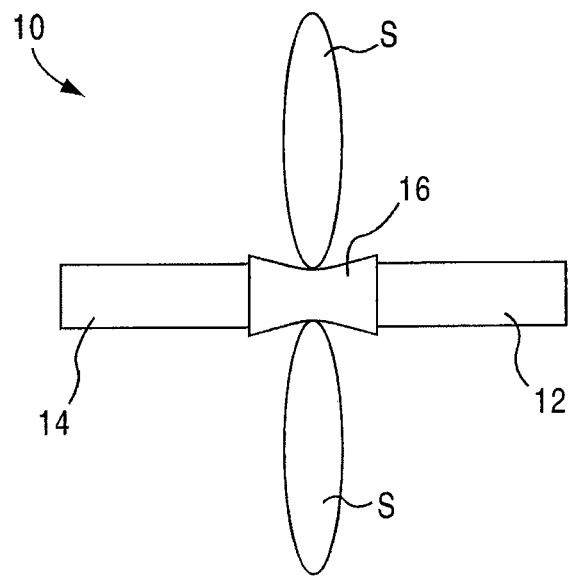
FIG. 1 is a schematic illustration of a posterior view of a medical device according to an embodiment of the invention in a first configuration adjacent two adjacent spinous processes.

As used in this specification and the appended claims, the singular forms "a," "an" and "the" include plural referents unless the context clearly dictates otherwise. Thus, for example, the term "a member" is intended to mean a single member or a combination of members, "a material" is intended to mean one or more materials, or a combination thereof. Furthermore, the words "proximal" and "distal" refer to direction closer to and away from, respectively, an operator (e.g., surgeon, physician, nurse, technician, etc.) who would insert the medical device into the patient, with the tip-end (i.e., distal end) of the device inserted inside a patient's body first. Thus, for example, the implant end first inserted inside the patient's body would be the distal end of the implant, while the implant end to last enter the patient's body would be the proximal end of the implant.

In some embodiments, a method includes disposing at least a portion of an implant in a space between adjacent spinous processes. The implant has a support member, a distal hub member, and an expandable member. At least a portion of the support member is disposed into the space between the adjacent spinous processes. A threaded member coupled to the distal hub member is rotated in a first rotational direction such that the distal hub member is moved in a first direction along a path defined by a longitudinal axis of the support member and at least a portion of the expandable member is moved to an expanded configuration.

In some embodiments, an apparatus includes a support member that defines a longitudinal axis and is configured to be implanted at least partially into a space between adjacent spinous processes. A distal hub member is coupled to the support member and an expandable member is coupled to the support member and has an expanded configuration and a collapsed configuration. An elongate member is coupled to the distal hub member and is configured to move at least a portion of the expandable member between an expanded configuration and a collapsed configuration when the elongate member is rotated. The elongate member configured to remain coupled to the distal hub member when the support member is implanted in the space between adjacent spinous processes.

In some embodiments, a method includes disposing at least a portion of a support member of an implant in a space between adjacent spinous processes. The support member of the implant defines a longitudinal axis and the implant has a first retention member and a second retention member. An axial force is exerted along the longitudinal axis such that each of the first retention member and the second retention member elastically expand in a direction transverse to the longitudinal axis. When elastically expanded, each of the first retention member and the second retention member has a greater outer perimeter than an outer perimeter of the support member.

In some embodiments, a method includes disposing at least a portion of a support member into a space between adjacent spinous processes. The support member defines a lumen between a proximal end of the support member and a distal end of the support member. An expandable member is inserted through the lumen of the support member such that a distal end portion of the expandable member is disposed outside a distal end of the lumen of the support member, and a proximal end portion of the expandable member is disposed outside a proximal end of the lumen of the support member. After the disposing and the inserting, the distal end portion of the expandable member and the proximal end portion of the expandable member are expanded such that each of the distal end portion of the expandable member and the proximal end portion of the expandable member has an outer diameter greater than an outer diameter of the support member.

In some embodiments, an apparatus includes a support member that is configured to be disposed in a space between adjacent spinous processes and that defines a lumen therethrough. An expandable member is configured to be disposed at least partially within the lumen of the support member. The expandable member is movable between a collapsed configuration and an expandable configuration while disposed within the lumen of the support member.

In some embodiments, a method includes disposing a support member of a spinal implant at least partially within a space between adjacent spinous processes. The support member has a first portion coupled to a second portion. An expandable member is inserted at least partially into a lumen of the support member when the expandable member is in a collapsed configuration. The expandable member is moved to an expanded configuration while disposed within the lumen of the support member such that the first portion of the support member and the second portion of the support member are moved from a collapsed configuration to an expanded configuration and a proximal end portion of the expandable member and a distal end portion of the expandable member each has an outer diameter greater than an outer diameter of the support member.

The term "body" is used here to mean a mammalian body. For example, a body can be a patient's body, or a cadaver, or a portion of a patient's body or a portion of a cadaver.

The term "parallel" is used herein to describe a relationship between two geometric constructions (e.g., two lines, two planes, a line and a plane, two curved surfaces, a line and a curved surface or the like) in which the two geometric constructions are substantially non-intersecting as they extend substantially to infinity. For example, as used herein, a line is said to be parallel to a curved surface when the line and the curved surface do not intersect as they extend to infinity. Similarly, when a planar surface (i.e., a two-dimensional surface) is said to be parallel to a line, every point along the line is spaced apart from the nearest portion of the surface by a substantially equal distance. Two geometric constructions are described herein as being "parallel" or "substantially parallel" to each other when they are nominally parallel to each other, such as for example, when they are parallel to each other within a tolerance. Such tolerances can include, for example, manufacturing tolerances, measurement tolerances or the like.

The term "normal" is used herein to describe a relationship between two geometric constructions (e.g., two lines, two planes, a line and a plane, two curved surfaces, a line and a curved surface or the like) in which the two geometric constructions intersect at an angle of approximately 90 degrees within at least one plane. For example, as used herein, a line is said to be normal to a curved surface when the line and the curved surface intersect at an angle of approximately 90 degrees within a plane. Two geometric constructions are described herein as being "normal" or "substantially normal" to each other when they are nominally normal to each other, such as for example, when they are normal to each other within a tolerance. Such tolerances can include, for example, manufacturing tolerances, measurement tolerances or the like.

FIG. 1 is a schematic illustration of a medical device according to an embodiment of the invention adjacent two adjacent spinous processes. The medical device 10 includes a proximal portion 12, a distal portion 14 and a central portion 16. The medical device 10 has a first configuration in which it can be inserted between adjacent spinous processes S. The central portion 16 is configured to contact the spinous processes S to prevent over-extension/compression of the spinous processes S. In some embodiments, the central portion 16 does not substantially distract the adjacent spinous processes S. In other embodiments, the central portion 16 does not distract the adjacent spinous processes S.

In the first configuration, the proximal portion 12, the distal portion 14 and the central portion 16 are coaxial (i.e., share a common longitudinal axis). In some embodiments, the proximal portion 12, the distal portion 14 and the central portion 16 define a tube having a constant inner diameter. In other embodiments, the proximal portion 12, the distal portion 14 and the central portion 16 define a tube having a constant outer diameter and/or inner diameter.

Figure 2:
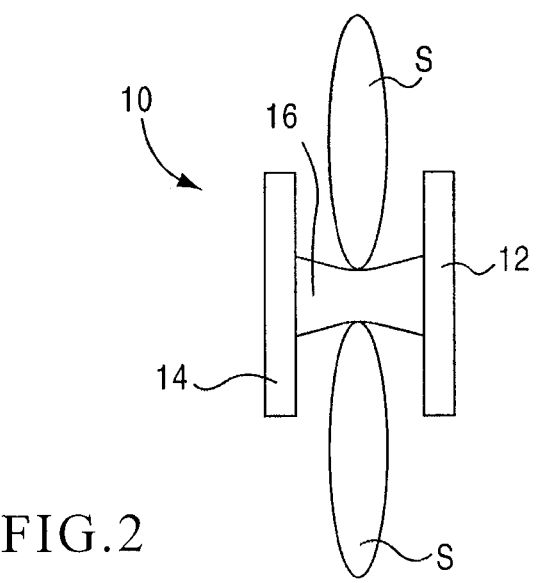
FIG. 2 is a schematic illustration of a posterior view of a medical device according to an embodiment of the invention in a second configuration adjacent two adjacent spinous processes.

The medical device 10 can be moved from the first configuration to a second configuration as illustrated in FIG. 2. In the second configuration, the proximal portion 12 and the distal portion 14 are positioned to limit lateral movement of the device 10 with respect to the spinous processes S. The proximal portion 12 and the distal portion 14 are configured to engage the spinous process (i.e., either directly or through surrounding tissue) in the second configuration. For purposes of clarity, the tissue surrounding the spinous processes S is not illustrated.

In some embodiments, the proximal portion 12, the distal portion 14 and the central portion 16 are monolithically formed. In other embodiments, one or more of the proximal portion 12, the distal portion 14 and the central portion 16 are separate components that can be coupled together to form the medical device 10. For example, the proximal portion 12 and distal portion 14 can be monolithically formed and the central portion can be a separate component that is coupled thereto.

In use, the spinous processes S can be distracted prior to inserting the medical device 10. Distraction of spinous processes is discussed below. When the spinous processes are distracted, a trocar can be used to define an access passage for the medical device 10. In some embodiments, the trocar can be used to define the passage as well as distract the spinous processes S. Once an access passage is defined, the medical device 10 is inserted percutaneously and advanced between the spinous processes, distal end 14 first, until the central portion 16 is located between the spinous processes S. Once the medical device 10 is in place between the spinous processes, the proximal portion 12 and the distal portion 14 are moved to the second configuration, either serially or simultaneously.

In some embodiments, the medical device 10 (also referred to herein as "implant" or "spinal implant") is inserted percutaneously (i.e., through an opening in the skin) and in a minimally-invasive manner. For example, as discussed in detail herein, the size of portions of the implant is expanded after the implant is inserted between the spinous processes. Once expanded, the size of the expanded portions of the implant is greater than the size of the opening. For example, the size of the opening/incision in the skin may be between 3 millimeters in length and 25 millimeters in length. In some embodiments, the size of the implant in the expanded configuration is between 3 and 25 millimeters.

Figure 3:
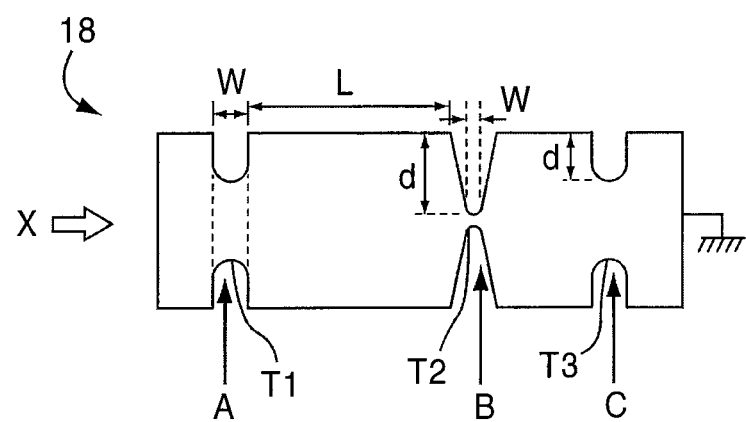
FIG. 3 is a schematic illustration of a deforming element according to an embodiment of the invention in a first configuration.

FIG. 3 is a schematic illustration of a deformable element 18 that is representative of the characteristics of, for example, the distal portion 14 of the medical device 10 in a first configuration. The deformable member 18 includes cutouts A, B, C along its length to define weak points that allow the deformable member 18 to deform in a predetermined manner. Depending upon the depth d of the cutouts A, B, C and the width w of the throats T1, T2, T3, the manner in which the deformable member 18 deforms under an applied load can be controlled and varied. Additionally, depending upon the length L between the cutouts A, B, C (i.e., the length of the material between the cutouts) the manner in which the deformable member 18 deforms can be controlled and varied.

Figure 4:
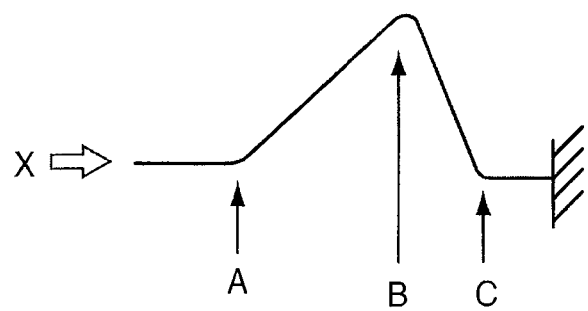
FIG. 4 is a schematic illustration of a side view of the expanding element illustrated in FIG. 3.

FIG. 4 is a schematic illustration of the expansion properties of the deformable member 18 illustrated in FIG. 3. When a load is applied, for example, in the direction indicated by arrow X, the deformable member 18 deforms in a predetermined manner based on the characteristics of the deformable member 18 as described above. As illustrated in FIG. 4, the deformable member 18 deforms most at cutouts B and C due to the configuration of the cutout C and the short distance between cutouts B and C. In some embodiments, the length of the deformable member 18 between cutouts B and C is sized to fit adjacent a spinous process.

The deformable member 18 is stiffer at cutout A due to the shallow depth of cutout A. As indicated in FIG. 4, a smooth transition is defined by the deformable member 18 between cutouts A and B. Such a smooth transition causes less stress on the tissue surrounding a spinous process than a more drastic transition such as between cutouts B and C. The dimensions and configuration of the deformable member 18 can also determine the timing of the deformation at the various cutouts. The weaker (i.e., deeper and wider) cutouts deform before the stronger (i.e., shallower and narrower) cutouts.

Figures 5, 6:
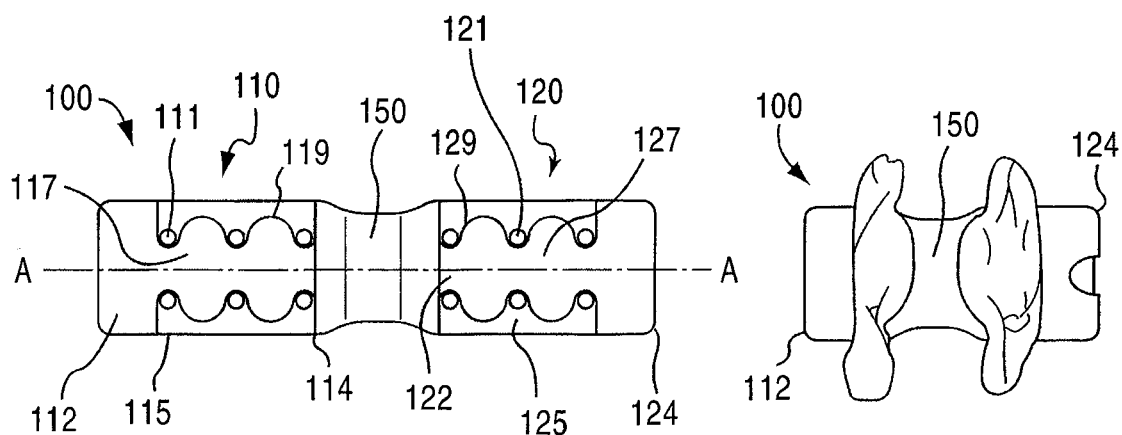
FIG. 5 is a side view of a medical device according to an embodiment of the invention in a first configuration.
FIG. 6 is a side view of the medical device illustrated in FIG. 5 in a second configuration.

FIGS. 5 and 6 illustrate a spinal implant 100 in a first configuration and second configuration, respectively. As shown in FIG. 5, the spinal implant 100 is collapsed in a first configuration and can be inserted between adjacent spinous processes. The spinal implant 100 has a first expandable portion 110, a second expandable portion 120 and a central portion 150. The first expandable portion 110 has a first end 112 and a second end 114. The second expandable portion 120 has a first end 122 and a second end 124. The central portion 150 is coupled between second end 114 and first end 122. In some embodiment, the spinal implant 100 is monolithically formed.

The first expandable portion 110, the second expandable portion 120 and the central portion 150 have a common longitudinal axis A along the length of spinal implant 100. The central portion 150 can have the same inner diameter as first expandable portion 110 and the second expandable portion 120. In some embodiments, the outer diameter of the central portion 150 is smaller than the outer diameter of the first expandable portion 110 and the second expandable portion 120.

In use, spinal implant 100 is inserted percutaneously between adjacent spinous processes. The first expandable portion 110 is inserted first and is moved past the spinous processes until the central portion 150 is positioned between the spinous processes. The outer diameter of the central portion 150 can be slightly smaller than the space between the spinous processes to account for surrounding ligaments and tissue. In some embodiments, the central portion directly contacts the spinous processes between which it is positioned. In some embodiments, the central portion of spinal implant 100 is a fixed size and is not compressible or expandable.

The first expandable portion 110 includes expanding members 115, 117 and 119. Between the expanding members 115, 117, 119, openings 111 are defined. As discussed above, the size and shape of the openings 111 influence the manner in which the expanding members 115, 117, 119 deform when an axial load is applied. The second expandable portion 120 includes expanding members 125, 127 and 129. Between the expanding members 125, 127, 129, openings 121 are defined.

As discussed above, the size and shape of the openings 121 influence the manner in which the expanding members 125, 127, 129 deform when an axial load is applied.

When an axial load is applied to the spinal implant 100, the spinal implant 100 expands to a second configuration as illustrated in FIG. 6. In the second configuration, first end 112 and second end 1140 of the first expandable portion 110 move towards each other and expanding members 115, 117, 119 project substantially laterally away from the longitudinal axis A. Likewise, first end 122 and second end 124 of the second expandable portion 120 move towards one another and expanding members 125, 127, 129 project laterally away from the longitudinal axis A. The expanding members 115, 117, 119, 125, 127, 129 in the second configuration form projections that extend to positions adjacent to the spinous processes between which the spinal implant 100 is inserted. In the second configuration, the expanding members 115, 117, 119, 125, 127, 129 inhibit lateral movement of the spinal implant 100, while the central portion 150 prevents the adjacent spinous processes from moving together any closer than the distance defined by the diameter of the central portion 150.

Figure 7:
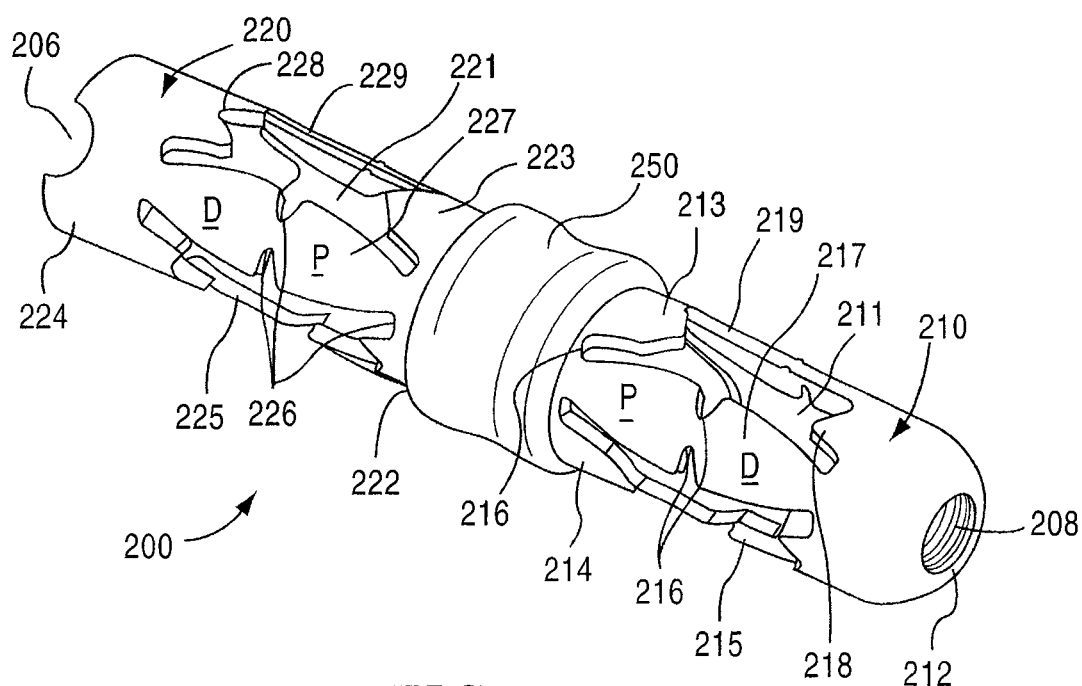
FIG. 7 is a perspective view of a medical device according to an embodiment of the invention in a first configuration.
Figure 11:
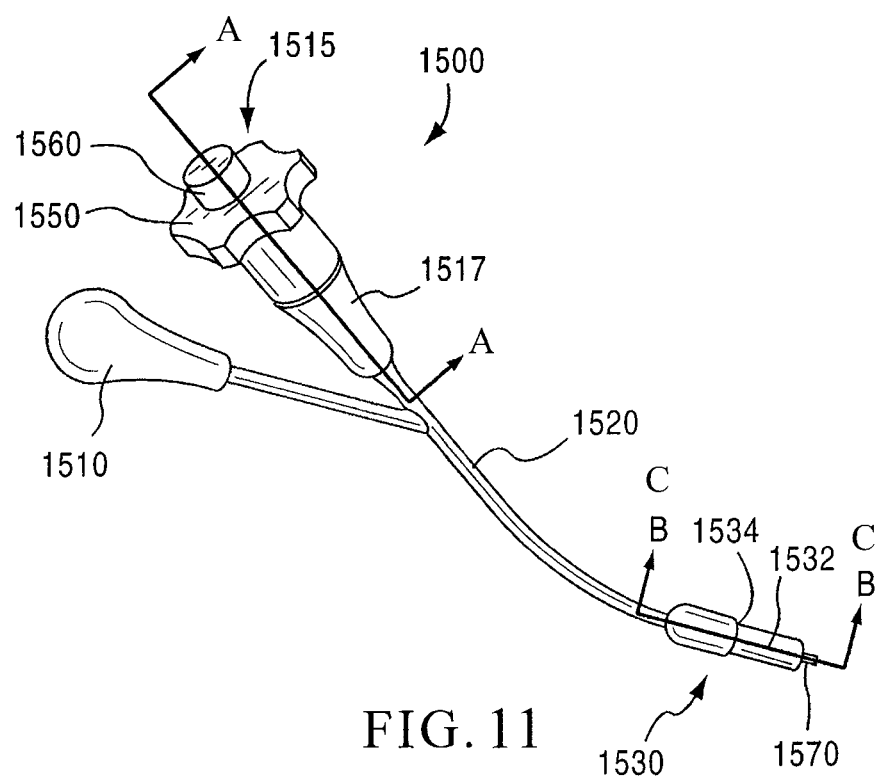
FIG. 11 is a perspective view of an implant expansion device according to an embodiment of the invention.
Figure 12:
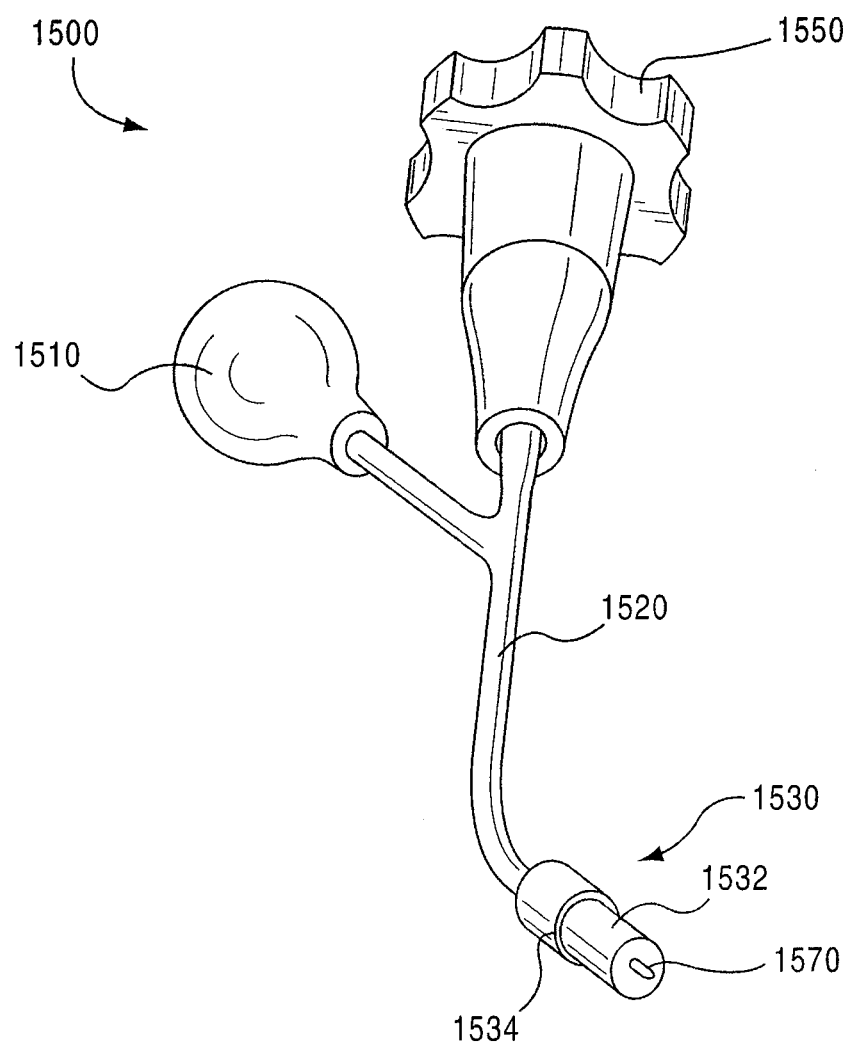
FIG. 12 is an alternative perspective view of the implant expansion device illustrated in FIG. 11.
Figure 13:
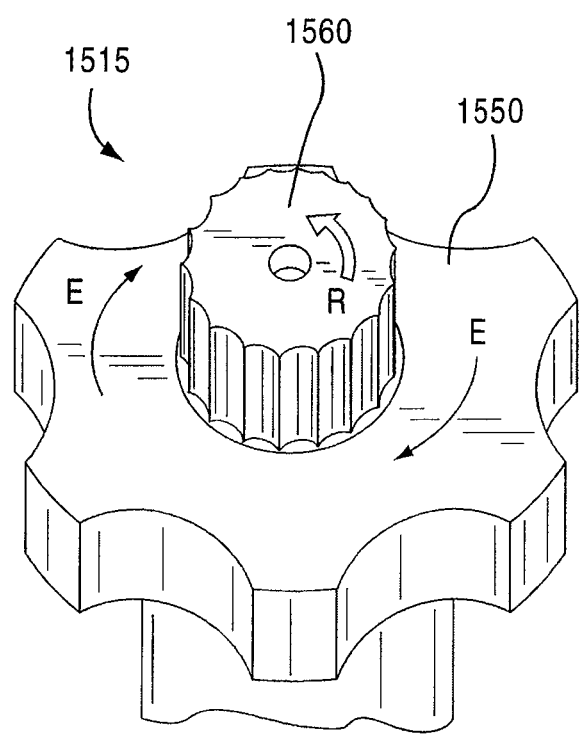
FIG. 13 is a perspective view of a portion of the implant expansion device illustrated in FIG. 11.

A spinal implant 200 according to an embodiment of the invention is illustrated in FIGS. 7-9 in various configurations. Spinal implant 200 is illustrated in a completely collapsed configuration in FIG. 7 and can be inserted between adjacent spinous processes. The spinal implant 200 has a first expandable portion 210, a second expandable portion 220 and a central portion 250. The first expandable portion 210 has a first end 212 and a second end 214. The second expandable portion 220 has a first end 222 and a second end 224. The central portion 250 is coupled between second end 214 and first end 222.

The first expandable portion 210, the second expandable portion 220 and the central portion 250 have a common longitudinal axis A along the length of spinal implant 200. The central portion 250 can have the same inner diameter as first expandable portion 210 and the second expandable portion 220. The outer diameter of the central portion 250 is greater than the outer diameter of the first expandable portion 210 and the second expandable portion 220. The central portion 250 can be monolithically formed with the first expandable portion 210 and the second expandable portion 220 or can be a separately formed sleeve coupled thereto or thereupon.

In use, spinal implant 200 is inserted percutaneously between adjacent spinous processes S. The first expandable portion 210 is inserted first and is moved past the spinous processes S until the central portion 250 is positioned between the spinous processes S. The outer diameter of the central portion 250 can be slightly smaller than the space between the spinous processes S to account for surrounding ligaments and tissue. In some embodiments, the central portion 250 directly contacts the spinous processes S between which it is positioned. In some embodiments, the central portion 250 of spinal implant 200 is a fixed size and is not compressible or expandable. In other embodiments, the central portion 250 can compress to conform to the shape of the spinous processes.

The first expandable portion 210 includes expanding members 215, 217 and 219. Between the expanding members 215, 217, 219, openings 211 are defined. As discussed above, the size and shape of the openings 211 influence the manner in which the expanding members 215, 217, 219 deform when an axial load is applied. Each expanding member 215, 217, 219 of the first expandable portion 210 includes a tab 213 extending into the opening 211 and an opposing mating slot 218. In some embodiments, the first end 212 of the first expandable portion 210 is rounded to facilitate insertion of the spinal implant 200.

The second expandable portion 220 includes expanding members 225, 227 and 229. Between the expanding members 225, 227, 229, openings 221 are defined. As discussed above, the size and shape of the openings 221 influence the manner in which the expanding members 225, 227, 229 deform when an axial load is applied. Each expanding member 225, 227, 229 of the second expandable portion 220 includes a tab 223 extending into the opening 221 and an opposing mating slot 228.

When an axial load is applied to the spinal implant 200, the spinal implant moves to a partially expanded configuration as illustrated in FIG. 8. In the partially expanded configuration, first end 222 and second end 224 of the second expandable portion 220 move towards one another and expanding members 225, 227, 229 project laterally away from the longitudinal axis A. To prevent the second expandable portion 220 from over-expanding, the tab 223 engages slot 228 and acts as a positive stop. As the axial load continues to be imparted to the spinal implant 200 after the tab 223 engages slot 228, the load is transferred to the first expandable portion 210. Accordingly, the first end 212 and the second end 214 then move towards one another until tab 213 engages slot 218 in the fully expanded configuration illustrated in FIG. 9. In the second configuration, expanding members 215, 217, 219 project laterally away from the longitudinal axis A. In some alternative embodiments, the first expandable portion and the second expandable portion expand simultaneously under an axial load.

The order of expansion of the spinal implant 200 can be controlled by varying the size of openings 211 and 221. For example, in the embodiments shown in FIGS. 7-9, the opening 221 is slightly larger than the opening 211. Accordingly, the notches 226 are slightly larger than the notches 216. As discussed above with respect to FIGS. 3 and 4, for this reason, the second expandable portion 220 will expand before the first expandable portion 210 under an axial load.

In the second configuration, the expanding members 215, 217, 219, 225, 227, 229 form projections that extend adjacent the spinous processes S. Once in the second configuration, the expanding members 215, 217, 219, 225, 227, 229 inhibit lateral movement of the spinal implant 200, while the central portion 250 prevents the adjacent spinous processes from moving together any closer than the distance defined by the diameter of the central portion 250.

The portion P of each of the expanding members 215, 217, 219, 225, 227, 229 proximal to the spinous process S expands such that portion P is substantially parallel to the spinous process S. The portion D of each of the expanding members 215, 217, 219, 225, 227, 229 distal from the spinous process S is angled such that less tension is imparted to the surrounding tissue.

In the second configuration, the expanding members 225, 227, 229 are separate by approximately 120 degrees from an axial view as illustrated in FIG. 10. While three expanding members are illustrated, two or more expanding members may be used and arranged in an overlapping or interleaved fashion when multiple implants 200 are inserted between multiple adjacent spinous processes. Additionally, regardless of the number of expanding members provided, the adjacent expanding members need not be separated by equal angles or distances.

The spinal implant 200 is deformed by a compressive force imparted substantially along the longitudinal axis A of the spinal implant 200. The compressive force is imparted, for example, by attaching a rod (not illustrated) to the first end 212 of the first expandable portion 210 and drawing the rod along the longitudinal axis while imparting an opposing force against the second end 224 of the second expandable portion 220. The opposing forces result in a compressive force causing the spinal implant 200 to expand as discussed above.

The rod used to impart compressive force to the spinal implant 200 can be removably coupled to the spinal implant 200. For example, the spinal implant 200 can include threads 208 at the first end 212 of the first expandable portion 210. The force opposing that imparted by the rod can be applied by using a push bar (not illustrated) that is removably coupled to the second end 224 of the second expandable portion 220. The push rod can be aligned with the spinal implant 200 by an alignment notch 206 at the second end 224. The spinal implant 200 can also be deformed in a variety of other ways, using a variety of expansion devices (also referred to herein as insertion tools, deployment tools and/or removal tools). While various types of implants are illustrated with various types of expansion devices, the expansion devices described herein can be used with any of the implants described herein.

FIGS. 11-16 illustrate an expansion device 1500 (also referred to herein as an insertion tool or a deployment tool) according to an embodiment of the invention. Although no particular implant is illustrated in FIGS. 11-16, any of the implants described herein, such as, for example, implant 200 (see FIG. 7), can be used with the expansion device 1500. The expansion device 1500 includes a guide handle 1510, a knob assembly 1515, a shaft 1520, a rod 1570 and an implant support portion 1530. The expansion device 1500 is used to insert an implant (not illustrated) in between adjacent spinous processes and expand the implant such that it is maintained in position between the spinous processes as described above. Both the guide handle 1510 and the knob assembly 1515 can be grasped to manipulate the expansion device 1500 to insert the implant. As described in more detail herein, the knob assembly 1515 is configured such that as the knob assembly 1515 is actuated, the rod 1570 translates and/or rotates within the shaft 1520; when the rod 1570 translates, the implant (not illustrated) is moved between its collapsed configuration and its expanded configuration; when the rod 1570 rotates, the implant is disengaged from the rod 1570.

Figure 15:
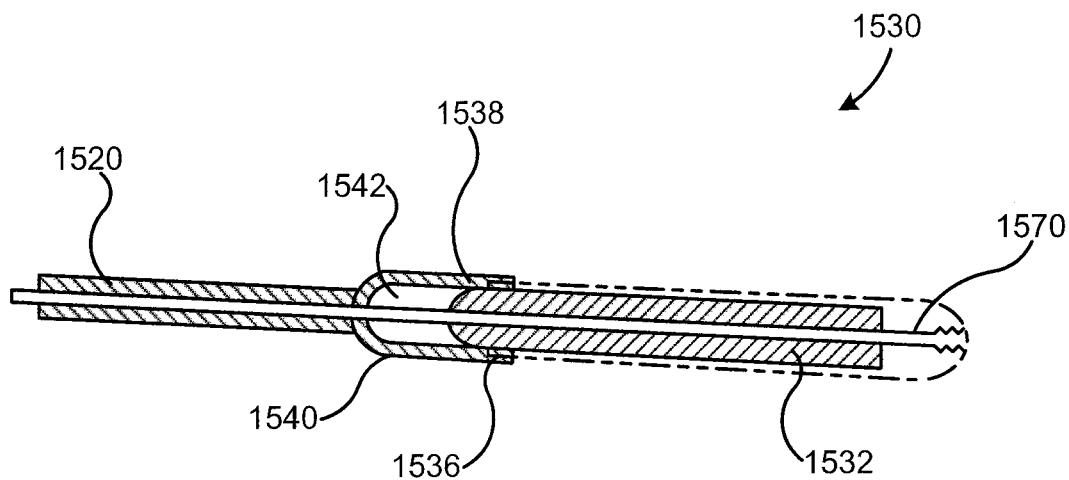
FIG. 15 is a cross-sectional view of a portion of the device illustrated in FIG. 1 in a first configuration, taken along line B-B in FIG. 11.
Figure 16:
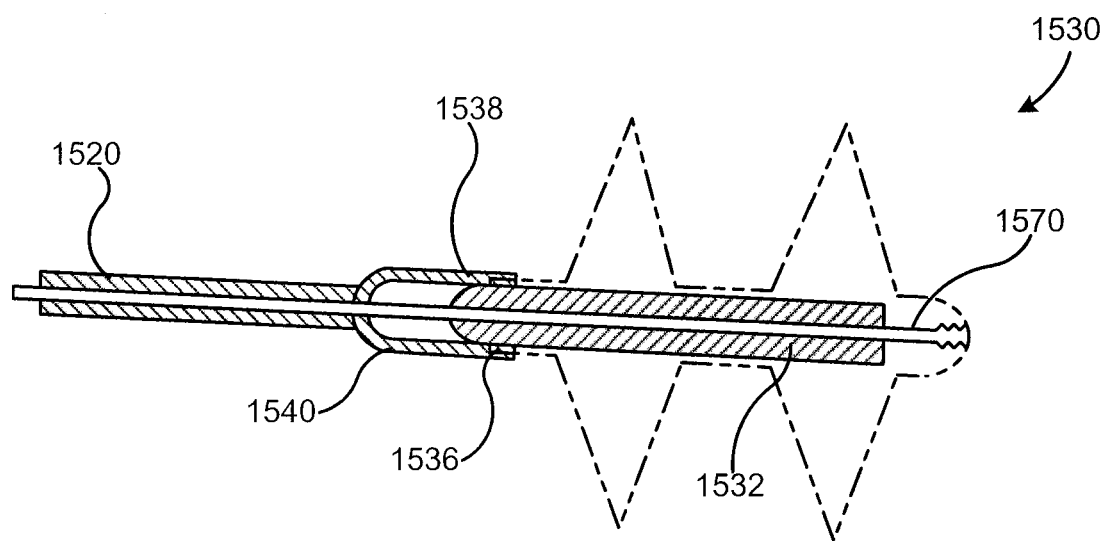
FIG. 16 is a cross-sectional view of a portion of the device illustrated in FIG. 1 in a second configuration, taken along line C-C in FIG. 11.

As best illustrated in FIGS. 15 and 16, the implant support portion 1530 includes a receiving member 1538 and a spacer 1532. The receiving member 1538 includes a side wall 1540 that is coupled to and supported by the distal end of the shaft 1520. The side wall 1540 defines an alignment protrusion 1536 and a receiving area 1542 configured to receive a portion of the spacer 1532. The implant slides over spacer 1532 until its proximal end is received within a recess 1534 defined by the side wall 1540 and the outer surface of the spacer 1532. The alignment protrusion 1536 is configured to mate with a corresponding notch on the implant (see, e.g., alignment notch 206 in FIG. 7) to align the implant with respect to the expansion device. Once the implant is aligned within the implant support portion 1530, the distal end of the implant is threadedly coupled to the distal end of rod 1570.

As illustrated, the spacer 1532 ensures that the implant is aligned longitudinally during the insertion and expansion process. The spacer 1532 can also be configured to maintain the shape of the implant during insertion and to prevent the expandable portions of the implant from extending inwardly during deployment of the implant. For example, in some embodiments, the spacer 1532 can be constructed from a solid, substantially rigid material, such as stainless steel, having an outer diameter and length corresponding to the inner diameter and length of the implant. In other embodiments, the expansion device can be configured to be used with implants that include an inner core configured to provide structural support to the implant (see, for example, FIGS. 17-23). In such embodiments, as described in more detail herein, the spacer of the insertion tool can be configured to cooperate with the inner core of the implant to provide the alignment and structural support of the implant during insertion and expansion.

Figure 14:
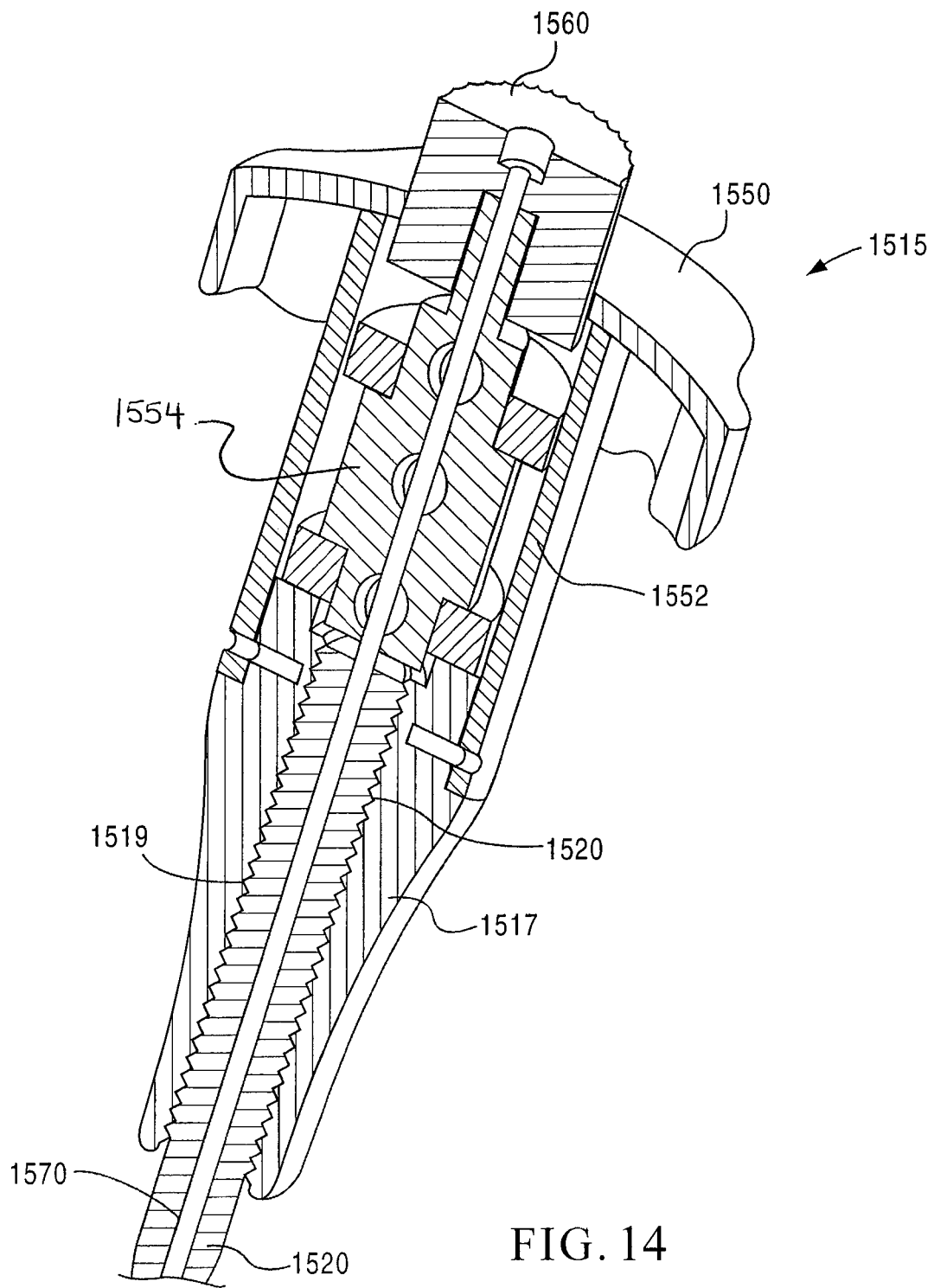
FIG. 14 is a cross-sectional view of a portion of the device illustrated in FIG. 11, taken along line A-A in FIG. 11.

The knob assembly 1515 includes an upper housing 1517 that threadedly receives the shaft 1520, an actuator knob 1550 and a release knob 1560 as best illustrated in FIG. 14. Upper housing 1517 includes internal threads 1519 that mate with external threads 1521 on shaft 1520. The proximal end of rod 1570 is coupled to the knob assembly 1515 by an adapter 1554, which is supported by two thrust bearings 1552. Actuator knob 1550 is coupled to the upper housing 1517 and is engaged with the adapter 1554 such that when actuator knob 1550 is turned in the direction indicated by arrows E (see FIG. 13), the rod 1570 translates axially relative to the shaft 1520 towards the proximal end of the device 1500, thereby acting as a draw bar and opposing the movement of the implant in the distal direction. In other words, when the implant is inserted between adjacent spinous processes and the actuator knob 1515 is turned, the distal end of the implant support portion 1530 imparts an axial force against the proximal end of the implant, while the rod 1570 causes an opposing force in the proximal direction. In this manner, the forces imparted by the implant support portion and the rod 1570 cause portions of the implant to expand in a transverse configuration such that the implant is maintained in position between the spinous processes as described above. The expansion device 1500 can also be used to move the implant from its expanded configuration to its collapsed configuration by turning the actuator knob 1550 in the opposite direction.

Once the implant is in position and fully expanded, the release knob 1560 is turned in the direction indicated by arrow R (see FIG. 13) thereby causing the rod 1570 to rotate within the shaft 1520. In this manner, the implant can be disengaged from the rod 1570. During this operation, the implant is prevented from rotating by the alignment protrusion 1536, which is configured to mate with a corresponding notch on the implant. Once the implant is decoupled from the rod 1570, the expansion tool 1500 can then be removed from the patient.

Although the knob assembly 1515 is shown and described as including an actuator knob 1550 and a release knob 1560 that are coaxially arranged with a portion of the release knob 1560 being disposed within the actuator knob 1550, in some embodiments, the release knob is disposed apart from the actuator knob. In other embodiments, the release knob and the actuator knob are not coaxially located. In yet other embodiments, the knob assembly 1515 does not include knobs having a circular shape, but rather includes levers, handles or any other device suitable for actuating the rod relative to the shaft as described above.

Figure 17:
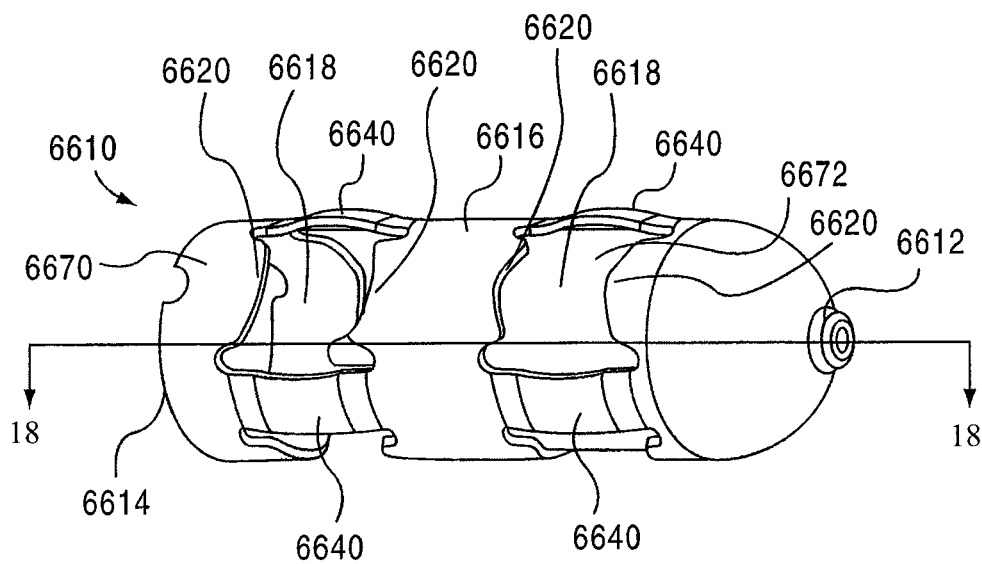
FIG. 17 is a side perspective view of an implant according to an embodiment of the invention shown in a collapsed configuration.
Figure 18:
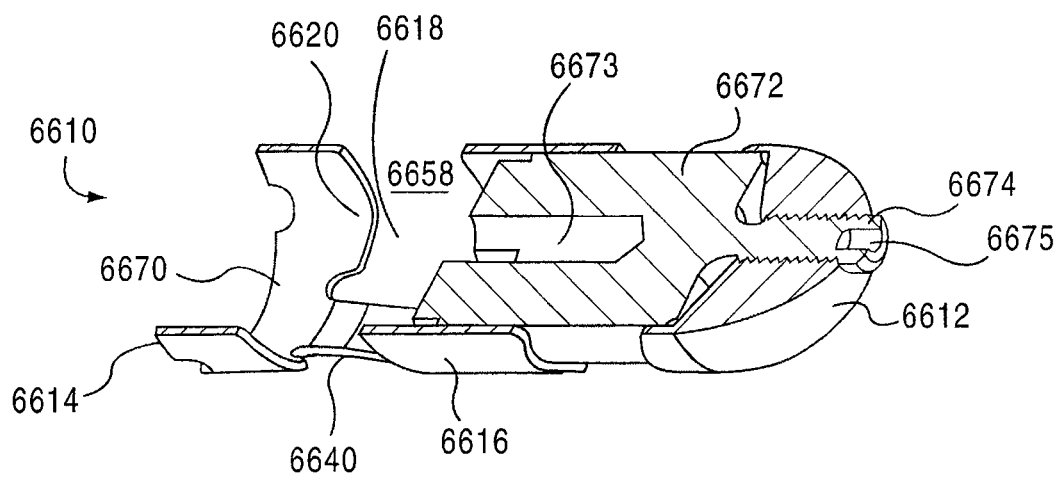
FIG. 18 is a cross-sectional view of the implant of FIG. 17 taken along line 18-18.
Figure 19:
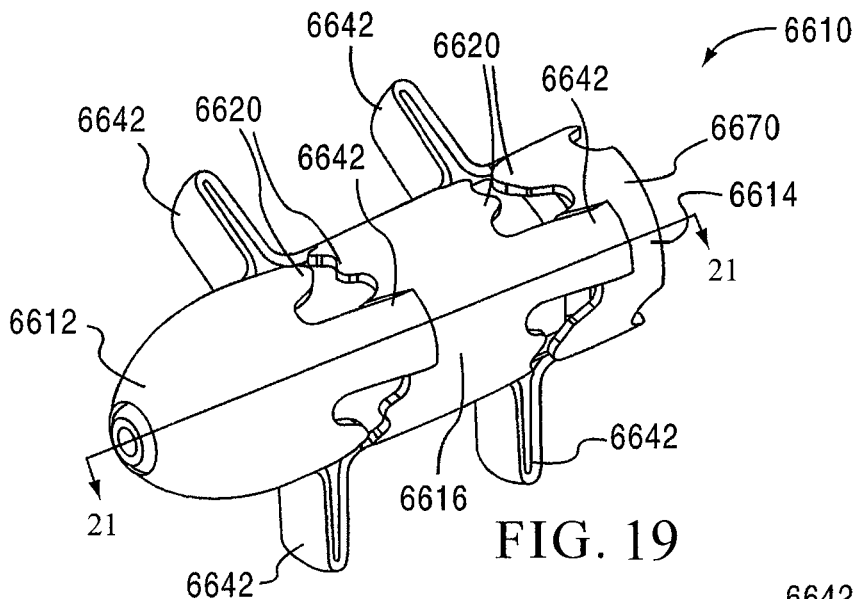
FIG. 19 is a side perspective view of the implant of FIG. 17 shown in an expanded configuration.
Figure 20:
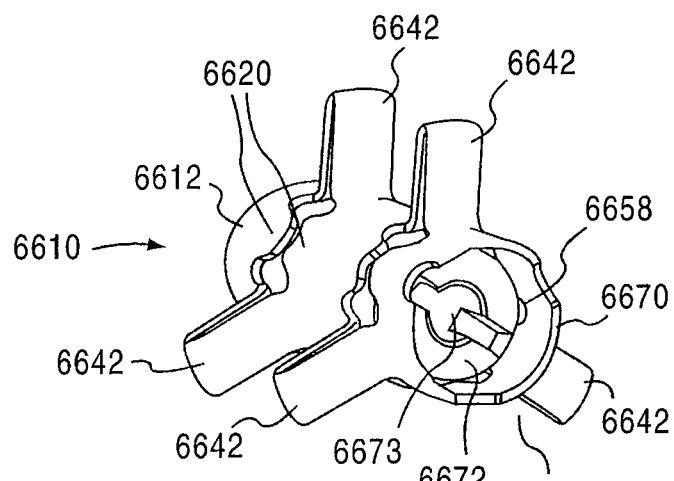
FIG. 20 is a rear perspective view of the implant of FIG. 17 shown in a collapsed configuration.
Figure 21:
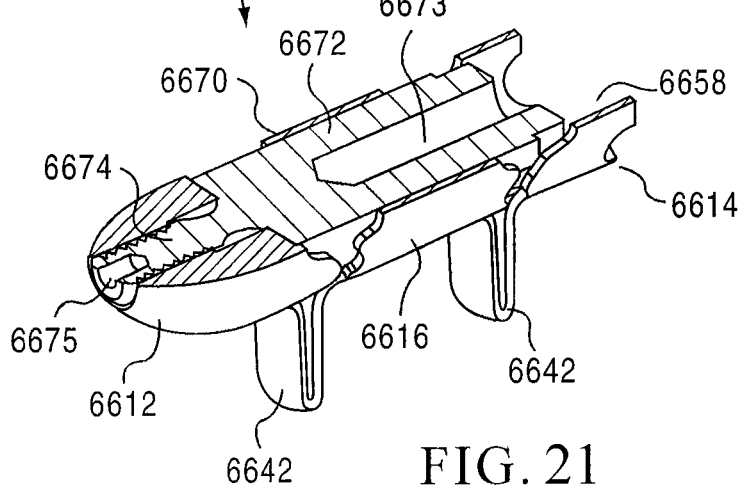
FIG. 21 is cross-sectional view of the implant of FIG. 17 shown in a collapsed configuration taken along line 21-21.
Figure 22:
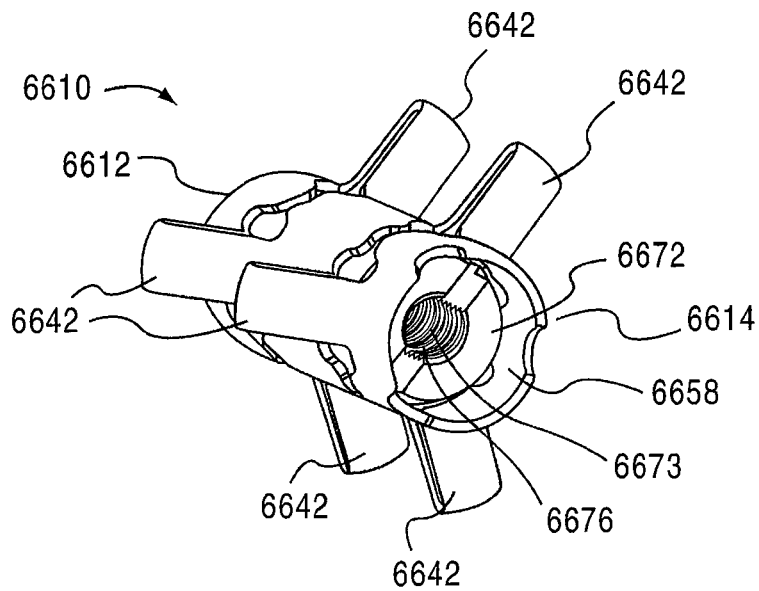
FIG. 22 is a rear perspective view of an implant according to an embodiment of the invention shown in a collapsed configuration.
Figure 23:
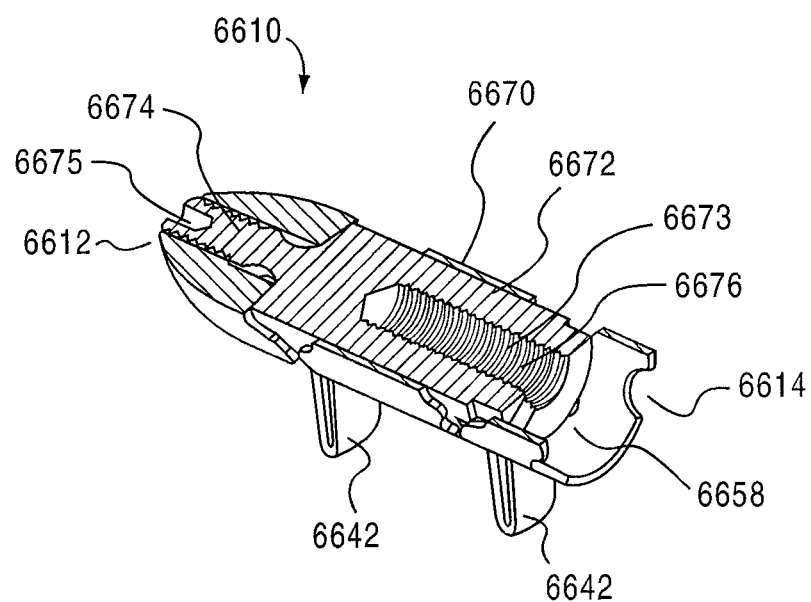
FIG. 23 is a cross-sectional view of the implant of FIG. 22 shown in a collapsed configuration.
Figure 24:
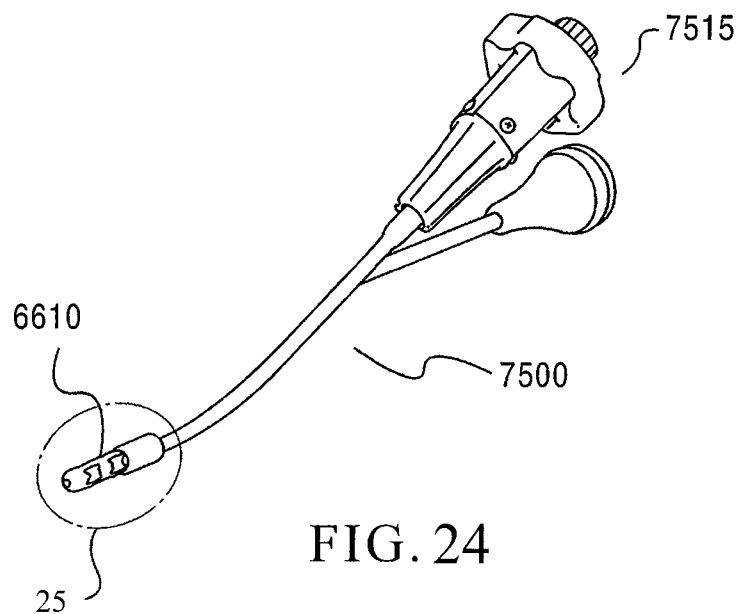
FIG. 24 is a perspective view of the implant of FIG. 22 in a collapsed configuration disposed on an expansion tool according to an embodiment of the invention.
Figure 25:
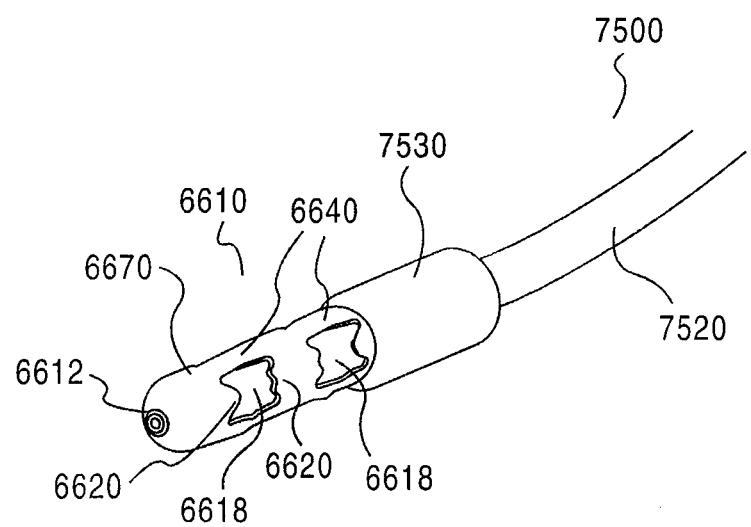
FIG. 25 is a perspective view of the implant and the expansion tool of FIG. 24 taken along region 25.
Figure 26:
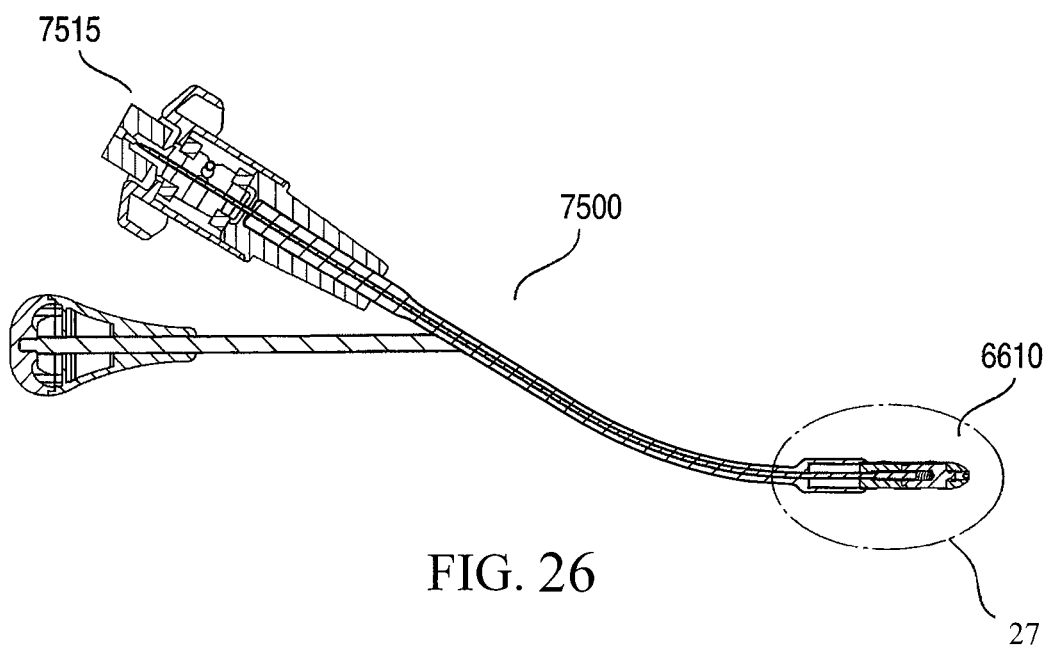
FIG. 26 is a side cross-sectional view of the implant and the expansion tool of FIG. 24.
Figure 27:
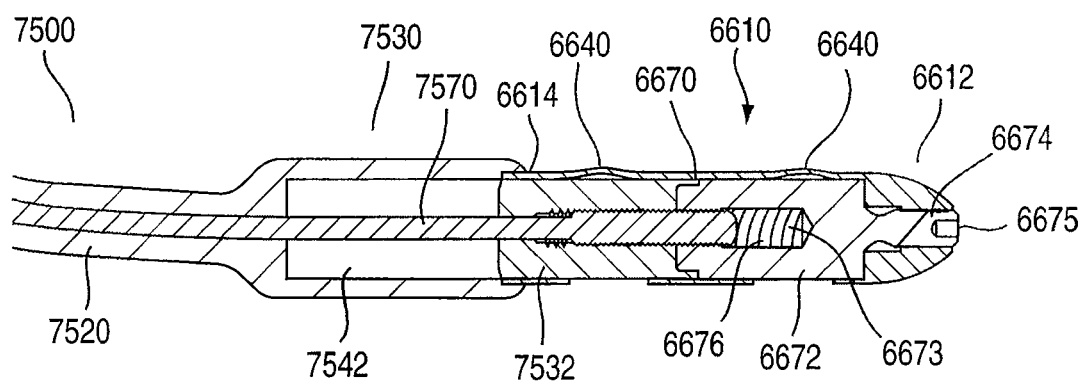
FIG. 27 is a side cross-sectional view of the implant and the expansion tool as shown in FIG. 26 taken along region 27.
Figure 28:
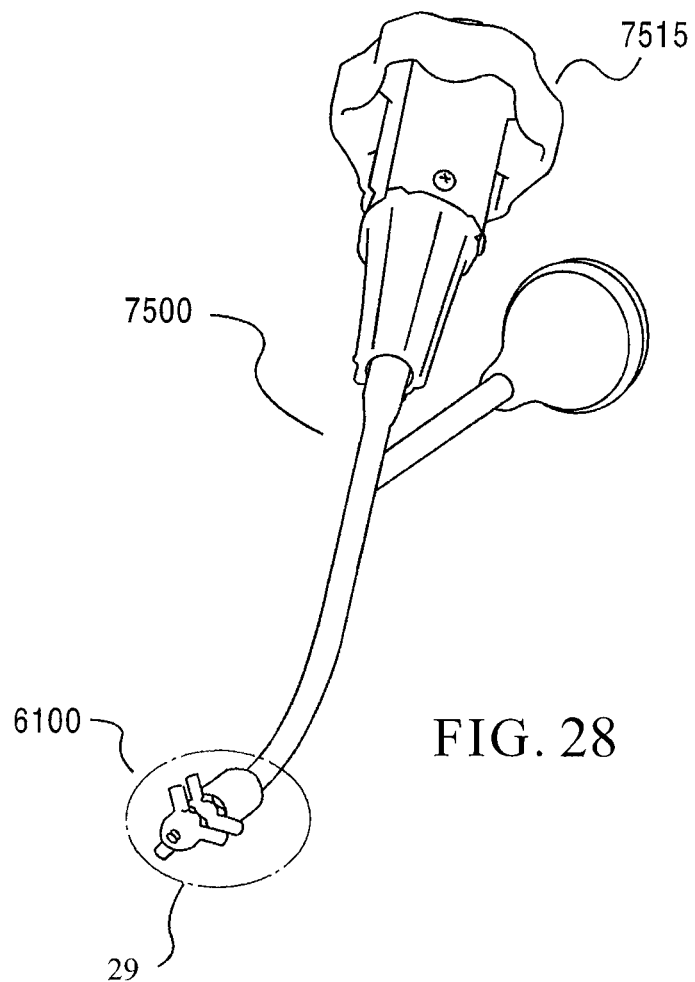
FIG. 28 is a perspective view of the implant of FIG. 22 in an expanded configuration disposed on an expansion tool according to an embodiment of the invention.

FIGS. 17-23 illustrate an implant 6610 according to another embodiment of the invention. The implant 6610 can be moved between a collapsed configuration, as shown in FIGS. 17 and 18, and an expanded configuration, as shown in FIGS. 19-23. The implant 6610 includes an outer shell 6670 having a distal portion 6612, a proximal portion 6614, and a central portion 6616. The outer shell 6670 defines a series of openings 6618 disposed between the distal portion 6612 and the central portion 6616, and the proximal portion 6614 and the central portion 6616. The outer shell 6670 includes a series of tabs 6620, a pair of which are disposed opposite each other, along the longitudinal axis of the implant 6610, on either side of each opening 6618. The outer shell 6670 also includes expandable portions 6640, which form extensions 6642 that extend radially from the outer shell 6670 when the implant 6610 is in the expanded configuration. As illustrated best in FIGS. 19-23, the arrangement of the openings 6618 and the tabs 6620 effect the shape and/or size of the extensions 6642. In some embodiments, the opposing tabs 6620 can be configured to engage each other when the implant 6610 is in the expanded configuration, thereby serving as a positive stop to limit the amount of expansion. In other embodiments, for example, the opposing tabs 6620 can be configured to engage each other during the expansion process, thereby serving as a positive stop, but remain spaced apart when the implant 6610 is in the expanded configuration (see, for example, FIGS. 19-23). In such embodiments, the elastic properties of the extensions 6642 can cause a slight "spring back," thereby causing the opposing tabs 6620 to be slightly spaced apart when the expansion device (also referred to as an insertion tool or a deployment tool) is disengaged from the implant 6610.

As illustrated best in FIG. 17, when the implant is in the collapsed configuration, the expandable portions 6640 are contoured to extend slightly radially from remaining portions of the outer shell 6670. In this manner, the expandable portions 6640 are biased such that when a compressive force is applied, the expandable portions 6640 will extend outwardly from the outer shell 6670. The expandable portions 6640 can be biased using any suitable mechanism. In some embodiments, for example, the expandable portions can be biased by including a notch in one or more locations along the expandable portion, as previously described. In other embodiments, the expandable portions can be biased by varying the thickness of the expandable portions in an axial direction. In yet other embodiments, the expandable portions can be stressed or bent prior to insertion such that the expandable portions are predisposed to extend outwardly when a compressive force is applied to the implant. In such embodiments, the radius of the expandable portions is greater than that of the remaining portions of the implant (e.g., the remaining cylindrical portions of the implant).

The implant 6610 also includes an inner core 6672 disposed within a lumen 6658 defined by the outer shell 6670. The inner core 6672 is configured to maintain the shape of the implant 6610 during insertion, to prevent the expandable portions from extending inwardly into a region inside of the outer shell 6670 during deployment and/or to maintain the shape of the central portion 6616 once the implant is in its desired position. As such, the inner core 6670 can be constructed to provide increased compressive strength to the outer shell 6670. In other words, the inner core 6672 can provide additional structural support to outer shell 6670 (e.g., in a direction transverse to the axial direction) by filling at least a portion of the region inside outer shell 6670 (e.g., lumen 6658) and contacting the walls of outer shell 6670. This can increase the amount of compressive force that can be applied to the implant 6610 while the implant 6610 still maintains its shape and, for example, the desired spacing between adjacent spinous processes. In some embodiments, the inner core 6672 can define a lumen 6673, while in other embodiments, the inner core 6672 can have a substantially solid construction. As illustrated, the inner core 6672 is fixedly coupled to the outer shell 6670 with a coupling portion 6674, which is configured to be threadedly coupled to the distal portion 6612 of the outer shell 6670. The distal end of the coupling portion 6674 of the inner core 6672 includes an opening 6675 configured to receive a tool configured to deform the distal end of the coupling portion 6674. In this manner once the inner core 6672 is threadedly coupled to the outer shell 6670, the coupling portion 6674 can be deformed or peened to ensure that the inner core 6672 does not become inadvertently decoupled from the outer shell 6670. In some embodiments, an adhesive, such as a thread-locking compound can be applied to the threaded portion of the coupling portion 6674 to ensure the that the inner core 6672 does not inadvertently become decoupled from the outer shell 6670. Although illustrated as being threadedly coupled, the inner core 6672 can be coupled to the outer shell 6670 by any suitable means. In some embodiments, for example, the inner core 6672 can be coupled to the central portion 6616 of the outer shell 6670 by, for example, a friction fit. In other embodiments, the inner core 6672 can be coupled to the outer shell 6670 by an adhesive. The inner core 6672 can have a length such that the inner core 6672 is disposed within the lumen 6658 along substantially the entire length of the outer shell 6670 or only a portion of the length of the outer shell 6670.

The proximal portion of the inner core 6672 includes an opening 6673 configured to receive a portion of an expansion device 7500 (also referred to as an insertion tool or a deployment tool), as shown in FIGS. 24-31. The expansion device 7500 is similar to the expansion device 1500 shown and described above (see e.g. FIGS. 11-16). The expansion device 7500 differs, however, from expansion device 1500 in that the expansion device 7500 includes spacer 7532 configured to cooperate with the inner core 6672 of the implant 6610. In such an arrangement, the threaded portion of rod 7570 of the expansion device 7500 removably engages to the internal threads 6676 of the inner core 6672 of the implant 6610, rather than coupling directly to the distal portion of the implant (as shown in FIGS. 15 and 16). Although the inner core 6672 is shown as being threadedly coupled to the expansion device 7500, the inner core 6672 can be removably coupled to the expansion device 7500 by any suitable means, such as a protrusion and detent arrangement.

Figure 29:
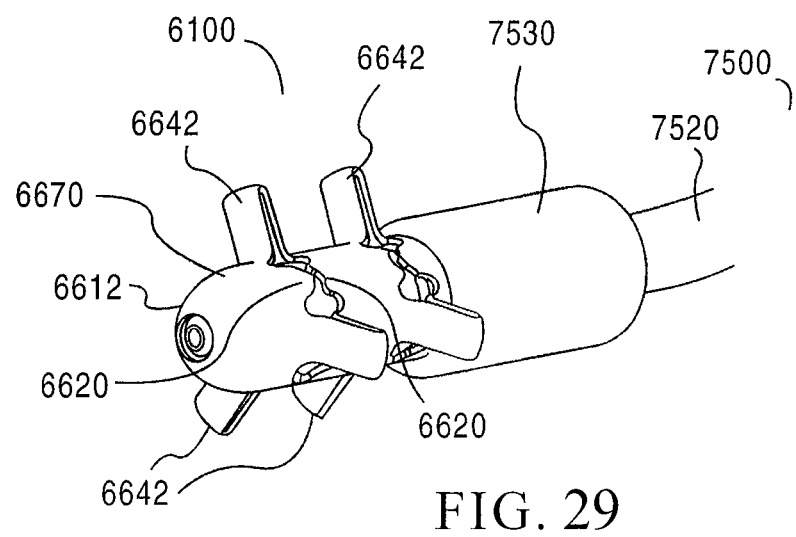
FIG. 29 is a perspective view of the implant and the expansion tool of FIG. 28 taken along region 29.
Figure 30:
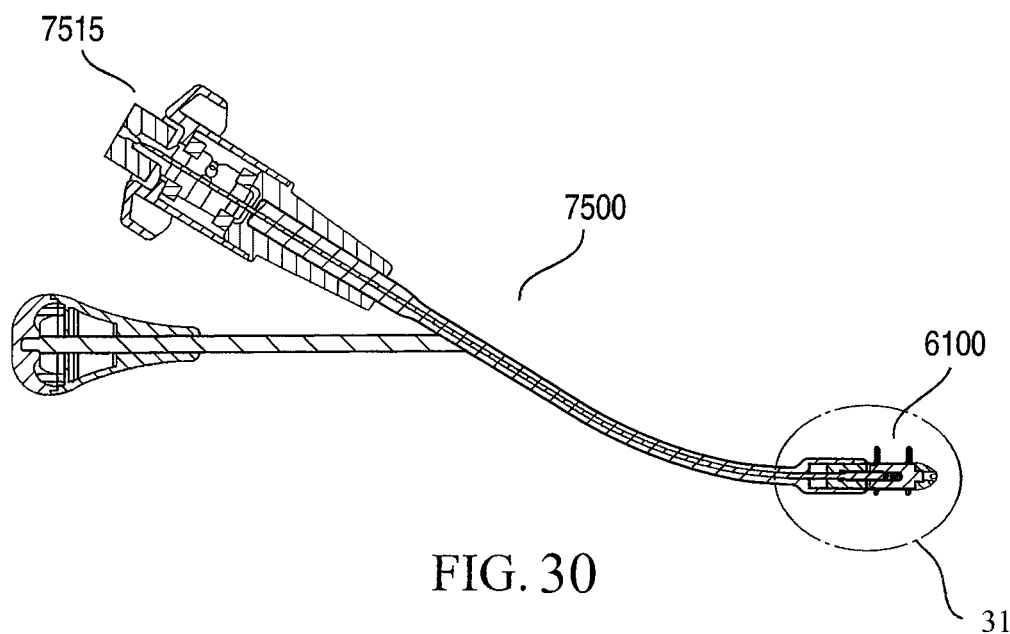
FIG. 30 is a side cross-sectional view of the implant and the expansion tool of FIG. 28.
Figure 31:
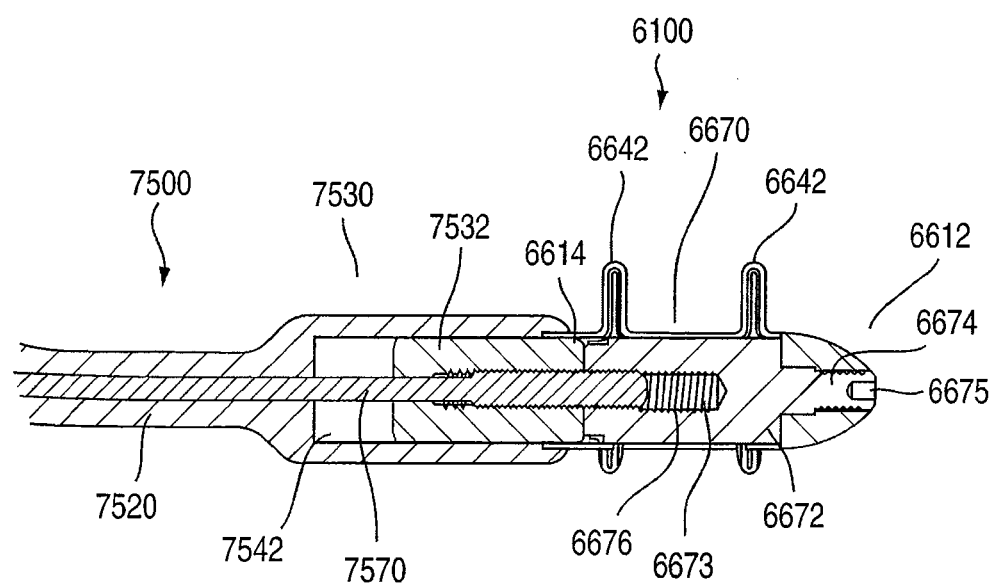
FIG. 31 is a side cross-sectional view of the implant and the expansion tool as shown in FIG. 30 taken along region 31.

In use, once the implant 6610 is positioned on the implant support portion 7530 of the expansion tool 7500 (see FIGS. 24 and 25), the implant is inserted into the patient's body and disposed between adjacent spinous processes. Once disposed between adjacent spinous processes, the expansion device can be used to move the inner core 6672 axially towards the proximal portion 6614 of the implant 6610 while simultaneously maintaining the position of the proximal portion 6614 of the implant 6610, as shown in FIGS. 29 and 31. In this manner, a compressive force is applied along the longitudinal axis of the outer shell 6670, thereby causing the outer shell 6670 to fold or bend to form extensions 6642 as described above. As illustrated, a portion of the spacer 7532 is received within the receiving area 7542 of the support portion 7530 as the implant 6610 is placed in the expanded configuration. Similarly, to move the implant 6610 from the expanded configuration to the collapsed configuration, the expansion device is actuated in the opposite direction to impart an axial force on the distal portion 6612 of the outer shell 6610 in a distal direction, moving the distal portion 6612 distally, and moving the implant 6610 to the collapsed configuration.

Once the implant 6610 is in its expanded configuration (see FIGS. 28-31), the implant 6610 can be disengaged from the expansion device 7500 by disengaging the distal portion of the rod 7570 from the opening 6673. The rod 7570 can be disengaged by actuating the knob assembly 7515 rotate the rod 7570 relative to the shaft 7520, as discussed above.

Although shown and described above without reference to any specific dimensions, in some embodiments, the outer shell 6670 can have a cylindrical shape having a length of approximately 34.5 mm (1.36 inches) and a diameter between 8.1 and 14.0 mm (0.32 and 0.55 inches). In some embodiments, the wall thickness of the outer shell can be approximately 5.1 mm (0.2 inches).

Similarly, in some embodiments, the inner core 6672 can have a cylindrical shape having an overall length of approximately 27.2 mm (1.11 inches) and a diameter between 8.1 and 14.0 mm (0.32 and 0.55 inches).

In some embodiments, the shape and size of the openings 6618 located adjacent the distal portion 6612 can be the same as that for the openings 6618 located adjacent the proximal portion 6614. In other embodiments, the openings 6618 can have different sizes and/or shapes. In some embodiments, the openings 6618 can have a length of approximately 11.4 mm (0.45 inches) and a width between 4.6 and 10 mm (0.18 and 0.40 inches).

Similarly, the shape and size of the tabs 6620 can be uniform or different as circumstances dictate. In some embodiments, for example, the longitudinal length of the tabs 6620 located adjacent the proximal portion 6614 can be shorter than the longitudinal length of the tabs 6620 located adjacent the distal portion 6612. In this manner, as the implant is moved from the collapsed configuration to the expanded configuration, the tabs adjacent the distal portion will engage each other first, thereby limiting the expansion of the expandable portions 6640 adjacent the distal portion 6612 to a greater degree than the expandable portions 6642 located adjacent the proximal portion 6614. In other embodiments, the longitudinal length of the tabs can be the same. In some embodiments, the longitudinal length of the tabs can be between 1.8 and 2.8 mm (0.07 and 0.11 inches). In some embodiments, the end portions of opposing tabs 6620 can have mating shapes, such as mating radii of curvature, such that the opposing tabs 6620 engage each other in a predefined manner.

Although illustrated as having a generally rectangular shape, the expandable portions 6640 and the resulting extensions 6642 can be of any suitable shape and size. In some embodiments, for example, the expandable portions can have a longitudinal length of approximately 11.4 mm (0.45 inches) and a width between 3.6 and 3.8 mm (0.14 and 0.15 inches). In other embodiments, size and/or shape of the expandable portions located adjacent the proximal portion 6614 can be different than the size and/or shape of the tabs 6620 located adjacent the distal portion 6612. Moreover, as described above, the expandable portions 6640 can be contoured to extend slightly radially from the outer shell 6670. In some embodiments, for example, the expandable portions can have a radius of curvature of approximately 12.7 mm (0.5 inches) along an axis normal to the longitudinal axis of the implant.

In some embodiments, the expandable portions 6640 and the outer shell 6670 are monolithically formed. In other embodiments, the expandable portions 6640 and the outer shell 6670 are formed from separate components having different material properties. For example, the expandable portions 6640 can be formed from a material having a greater amount of flexibility, while the outer shell 6670 can be formed from a more rigid material. In this manner, the expandable portions 6640 can be easily moved from the collapsed configuration to the expanded configuration, while the outer shell 6670 is sufficiently strong to resist undesirable deformation when in use.

In one embodiment, an apparatus includes a first body coupled to a second body. The first body and the second body collectively are configured to be releasably coupled to an implant device configured to be disposed between adjacent spinous processes. A first engaging portion is coupled to the first body, and a second engaging portion is coupled to the second body. The first engaging portion and/or the second engaging portion is configured to be received within a first opening defined by the implant device. The first body configured to be moved relative to the second body such that a distance between the first engaging portion and the second engaging portion is moved between a first distance and a second distance, and simultaneously a length of the implant device is moved between a first length and a second length.

In another embodiment, a kit includes an implant that is reconfigurable between an expanded configuration and a collapsed configuration while disposed between adjacent spinous processes. The implant has a longitudinal axis and defines an opening. A deployment tool is configured to be releasably coupled to the implant. The deployment tool includes an engaging portion configured to be removably received within the opening of the implant and extend in a transverse direction relative to the longitudinal axis when the deployment tool is coupled to the implant. The deployment tool is configured to move the implant between the collapsed configuration and the expanded configuration while the implant is disposed between the adjacent spinous processes.

Figure 32:
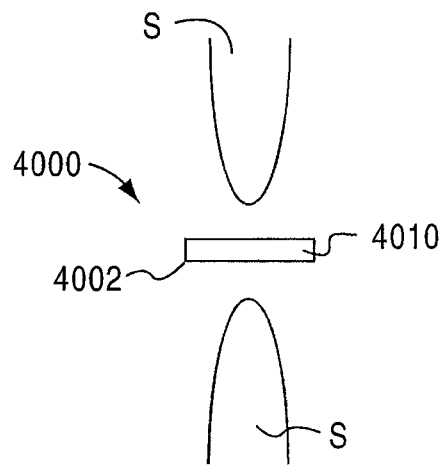
FIGS. 32-35 are schematic illustrations of a posterior view of a medical device according to an embodiment of the invention in a first configuration (FIG. 32), a second (FIGS. 33 and 35) configuration and a third configuration (FIG. 34).
Figure 33:
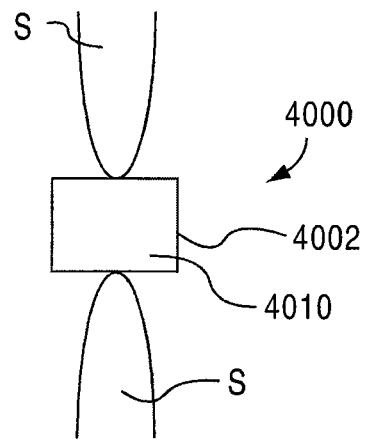
Figure 34:
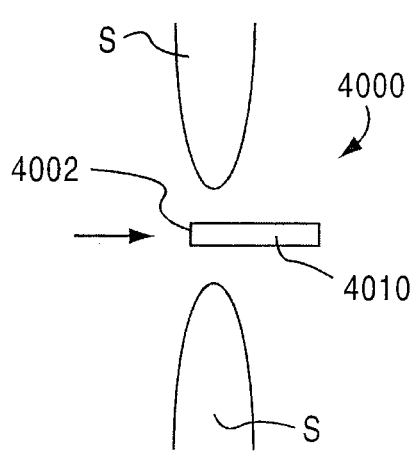

FIGS. 32-35 are schematic illustrations of a posterior view of a medical device 4000 according to an embodiment of the invention positioned adjacent two adjacent spinous processes S in a first configuration (FIG. 32), a second configuration (FIGS. 33 and 35) and a third configuration (FIG. 34). The medical device 4000 includes an expandable member 4002 having an inner area (not shown) and an outer surface 4010. The outer surface 4010 is configured to be disposed between the spinous processes S to prevent over-extension/compression of the spinous processes S. In some embodiments, the expandable member 4002 distracts the adjacent spinous processes S. In other embodiments, the expandable member 4002 does not distract the adjacent spinous processes S.

Figure 35:
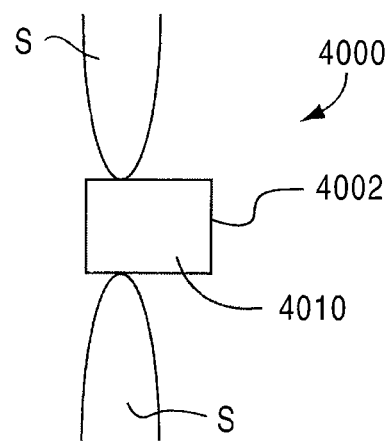

The expandable member 4002 has a first configuration, a second configuration and a third configuration. When in each configuration, the expandable member 4002 has an associated volume. As illustrated in FIG. 32, the first configuration represents a substantially contracted condition in which the expandable member 4002 has a minimal volume. When the expandable member 4002 is in the first configuration, the medical device 4000 is inserted between the adjacent spinous processes S. As illustrated in FIGS. 33 and 35, the second configuration represents an expanded condition in which the expandable member 4002 has a large volume. When the expandable member 4002 is in the second configuration, the outer surface 4010 of the medical device 4000 contacts the adjacent spinous processes S during at least a portion of the range of motion of the spinous processes. As illustrated in FIG. 34, the third configuration represents a partially expanded condition in which the expandable member 4002 has a volume between that associated with the first configuration and that associated with the second configuration. When the expandable member 4002 is in the third configuration, the medical device 4000 can be repositioned between the adjacent spinous processes, as indicated by the arrow in FIG. 34. The medical device can then be subsequently re-expanded into the second configuration, as illustrated in FIG. 35.

Figure 36:
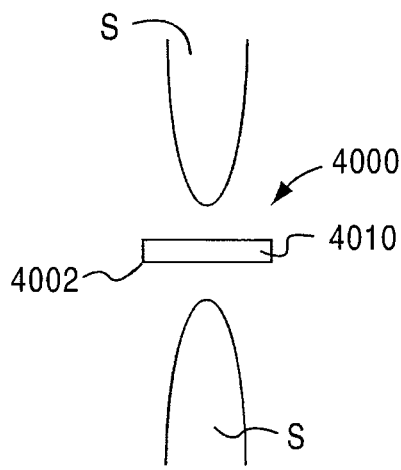
FIGS. 36-38 are schematic illustrations of a posterior view of a medical device according to an embodiment of the invention in a first configuration, a second configuration and a third configuration, respectively.
Figure 37:
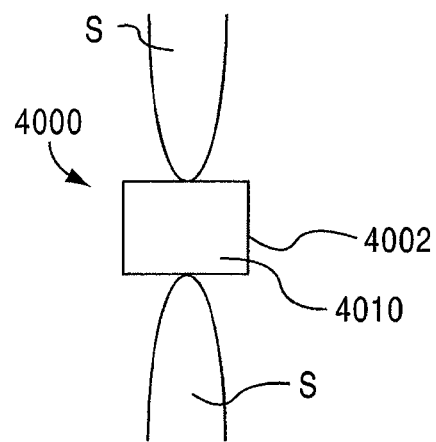
Figure 38:
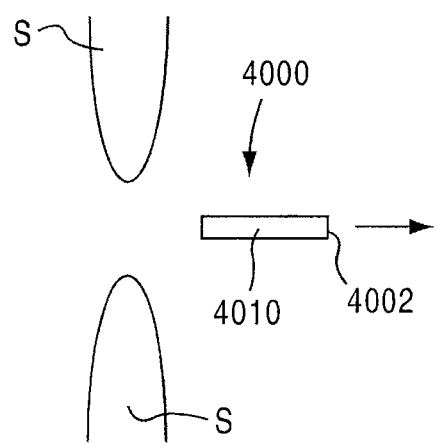
Figure 39:
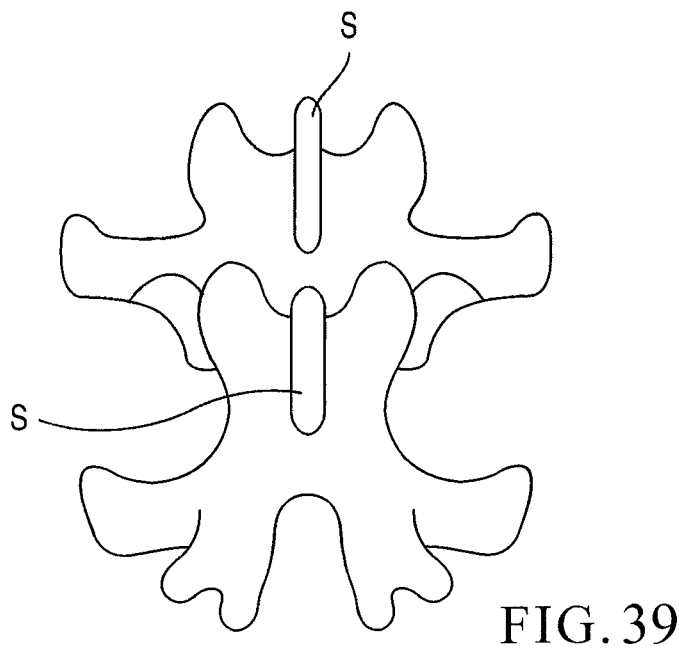
FIGS. 39-44 are posterior views of a medical device according to an embodiment of the invention inserted between adjacent spinous processes in a first lateral positions and a second lateral position.

FIGS. 36-38 are schematic illustrations of a posterior view of the medical device 4000 positioned adjacent two adjacent spinous processes S in a first configuration, a second configuration and a third configuration, respectively. As described above, when the expandable member 4002 is in the first configuration, the medical device 4000 is inserted between the adjacent spinous processes S. The expandable member 4002 is then expanded to the second configuration, in which the outer surface 4010 of the medical device 4000 is disposed between the adjacent spinous processes S. The expandable member 4002 is then contracted to the third configuration to facilitate removal of the medical device 4000, as shown in FIG. 38. In some embodiments, the third configuration can be the same as the first configuration.

In use, the adjacent spinous processes S can be distracted prior to inserting the medical device 4000 into a body, as described herein. When the spinous processes S are distracted, a trocar (not shown) can be used to define an access passageway (not shown) for the medical device 4000. In some embodiments, the trocar can be used to define the passage as well as to distract the spinous processes S. Once an access passageway is defined, the medical device 4000 is inserted percutaneously and advanced between the spinous processes S and placed in the desired position between the adjacent spinous processes S. Once the medical device 4000 is in the desired position, the expandable member is expanded to the second condition, causing the outer surface 4010 to engage the spinous processes S.

In some embodiments, the adjacent spinous processes can be distracted by a first expandable member (not shown) configured to distract bone. Upon distraction, the first expandable member is contracted and removed from the body. The medical device 4000 is then inserted percutaneously, advanced between the spinous processes S, placed in the desired position and expanded, as described above.

In some embodiments, the medical device 4000 is inserted percutaneously (i.e., through an opening in the skin) and in a minimally-invasive manner. For example, as discussed in detail herein, the overall sizes of portions of the medical device 4000 are increased by transitioning the expandable member 4002 from the first configuration to the second configuration after the medical device 4000 is inserted between the adjacent spinous processes S. When in the expanded second configuration, the sizes of portions of the medical device 4000 are greater than the size of the opening. For example, the size of the opening/incision in the skin can be between 3 millimeters in length and 25 millimeters in length across the opening. In some embodiments, the size of the medical device 4000 in the expanded second configuration is between 3 and 25 millimeters across the opening.

Figure 40:
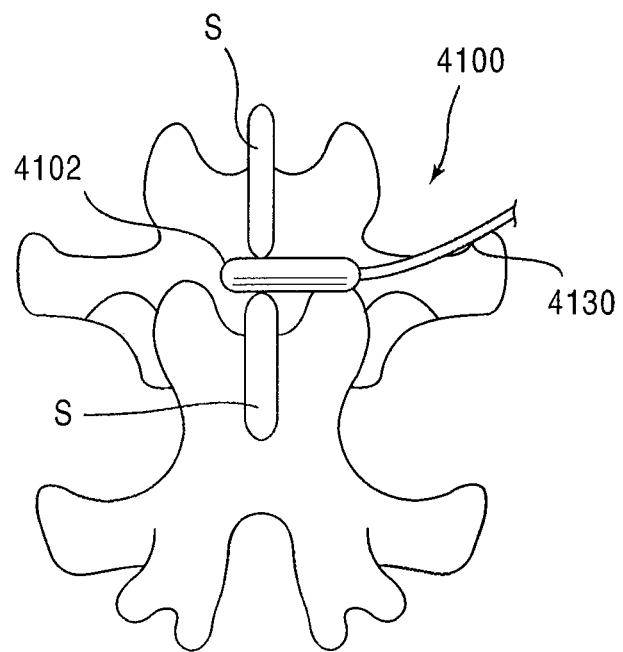
Figure 41:
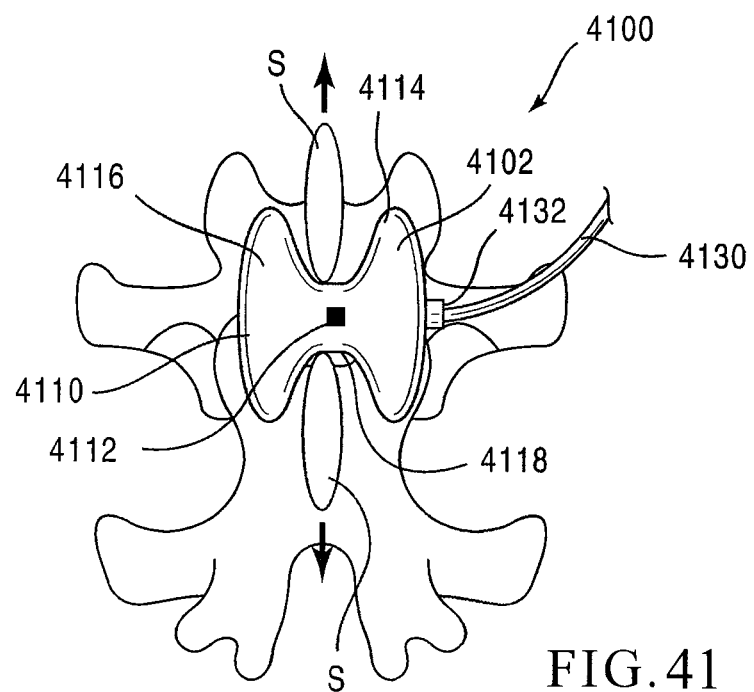
Figure 42:
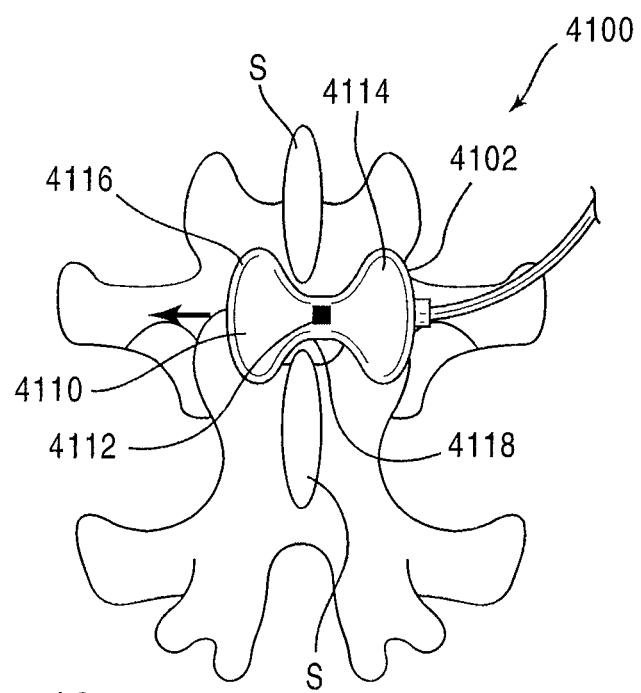
Figure 43:
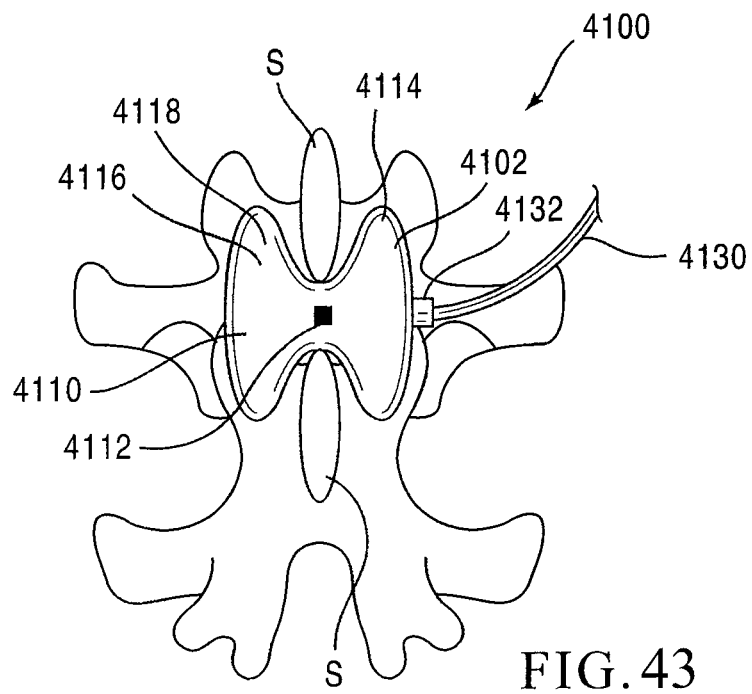

FIGS. 39-44 are posterior views of a spinal implant 4100 according to an embodiment of the invention inserted between adjacent spinous processes S in a first lateral position (FIG. 41) and a second lateral position (FIG. 43). The spinal implant 4100 includes an expandable member 4102, a sensor 4112 and a valve 4132. The expandable member 4102 has an inner area (not shown), an outer surface 4110, a support portion 4118, a proximal retention portion 4114 and a distal retention portion 4116. The expandable member 4102 is repeatably positionable in a first configuration (FIG. 40), a second configuration (FIGS. 41, 43 and 44) and a third configuration (FIG. 42). When in each configuration, the expandable member 4102 has an associated volume, as will be discussed below.

In use, the spinal implant 4100 is positioned in the substantially contracted first configuration during insertion and/or removal (see FIG. 40). As discussed above, the spinal implant 4100 is inserted percutaneously between adjacent spinous processes S. The distal retention portion 4116 of the expandable member 4102 is inserted first and is moved past the spinous processes S until the support portion 4118 is positioned between the spinous processes S. When in the first configuration, the support portion 4118 can be can be sized to account for ligaments and tissue surrounding the spinous processes S. For purposes of clarity, such surrounding ligaments and tissue are not illustrated.

As illustrated in FIG. 41, once in position, the expandable member 4102 is expanded into the second configuration by conveying a fluid (not shown) from an area outside of the expandable member 4102 to the inner area of the expandable member 4102. The fluid is conveyed by an expansion tool 4130, such as a catheter, that is matingly coupled to the valve 4132. The valve 4132 can be any valve suitable for sealably connecting the inner area of the expandable member 4102 to an area outside of the expandable member 4102. For example, in some embodiments, the valve 4132 can be, for example a poppet valve, a pinch valve or a two-way check valve. In other embodiments, the valve includes a coupling portion (not shown) configured to allow the expansion tool 4130 to be repeatably coupled to and removed from the valve 4132. For example, in some embodiments, the valve 4132 can include a threaded portion configured to matingly couple the expansion tool 4130 and the valve 4132.

The fluid is configured to retain fluidic properties while resident in the inner area of the expandable member 4102. In this manner, the spinal implant 4100 can be repeatably transitioned from the expanded second configuration to the first configuration and/or the third configuration by removing the fluid from the inner area of the expandable member 4102. In some embodiments, the fluid can be a biocompatible liquid having constant or nearly constant properties. Such liquids can include, for example, saline solution. In other embodiments, the fluid can be a biocompatible liquid configured to have material properties that change over time while still retaining fluidic properties sufficient to allow removal of the fluid. For example, the viscosity of a fluid can be increased by adding a curing agent or the like. In this manner, the fluid can provide both the requisite structural support while retaining the ability to be removed from the inner area of the expandable member 4102 via the valve 4132. In yet other embodiments, the fluid can be a biocompatible gas.

The outer surface 4110 of the support portion 4118 can distract the adjacent spinous processes S as the expandable member 4102 expands to the second configuration, as indicated by the arrows shown in FIG. 41. In some embodiments, the support portion 4118 does not distract the adjacent spinous processes S. For example, as discussed above, the adjacent spinous processes S can be distracted by a trocar and/or any other device suitable for distraction.

When in the second configuration, the outer surface 4110 of the support portion 4118 is configured to engage the spinous processes S for at least a portion of the range of motion of the spinous processes S to prevent over-extension/compression of the spinous processes S. In some embodiments, the engagement of the spinous processes S by the outer surface 4110 of the support portion 4118 is not continuous, but occurs upon spinal extension.

When in the second configuration, the proximal retention portion 4114 and the distal retention portion 4116 each have a size S1 (shown in FIG. 45) that is greater than the vertical distance D1 (shown in FIG. 45) between the spinous processes. In this manner, the proximal retention portion 4114 and the distal retention portion 4116 are disposed adjacent the sides of spinous processes S (i.e., either through direct contact or through surrounding tissue), thereby limiting movement of the spinal implant 4100 laterally along a longitudinal axis of the support portion 4118.

The expandable member 4102 can be made from any number of biocompatible materials, such as, for example, PET, Nylons, cross-linked Polyethylene, Polyurethanes, and PVC. In some embodiments, the chosen material can be substantially inelastic, thereby forming a low-compliant expandable member 4102. In other embodiments, the chosen material can have a higher elasticity, thereby forming a high-compliant expandable member 4102. In yet other embodiments, the expandable member 4102 can be made from a combination of materials such that one portion of the expandable member 4102, such as the support portion 4118, can be low-compliant while other portions of the expandable member 4102, such as the proximal retention portion 4114 and/or distal retention portion 4116 are more highly compliant. In yet other embodiments, a portion of the expandable member 4102 can include a rigid, inflexible material to provide structural stiffness. For example, the support portion 4118 can be constructed of a composite material that includes a rigid, inflexible material to facilitate distraction of the adjacent spinous processes.

In some embodiments, the expandable member 4102 includes a radiopaque material, such as bismuth, to facilitate tracking the position of the spinal implant 4100 during insertion and/or repositioning. In other embodiments, the fluid used to expand the expandable member 4102 includes a radiopaque tracer to facilitate tracking the position of the spinal implant 4100.

In the illustrated embodiment, the spinal implant 4100 includes a sensor 4112 coupled to the expandable member 4102. In some embodiments, the sensor 4112 is a strain gauge sensor that measures a force applied to the support portion 4118 of the expandable member 4102. The sensor 4112 can include multiple strain gauges to facilitate measuring multiple force quantities, such as a compressive force and/or a tensile force. In other embodiments, the sensor 4112 is a variable capacitance type pressure sensor configured to measure a force and/or a pressure of the fluid contained within the inner portion of the expandable member 4102. In yet other embodiments, the sensor 4112 is a piezoelectric sensor that measures a pressure of the fluid contained within the inner portion of the expandable member 4102. In still other embodiments, the spinal implant 4100 can include multiple sensors 4112 located at various locations to provide a spatial profile of the force and/or pressure applied to the expandable member 4102. In this manner, a practitioner can detect changes in the patient's condition, such those that may result in a loosening of the spinal implant 4100.

In some embodiments, the sensor 4112 can be remotely controlled by an external induction device. For example, an external radio frequency (RF) transmitter (not shown) can be used to supply power to and communicate with the sensor 4112. In other embodiments, an external acoustic signal transmitter (not shown) can be used to supply power to and communicate with the sensor 4112. In such an arrangement, for example, the sensor can include a pressure sensor, of the types described above, for measuring a pressure; an acoustic transducers, and an energy storage device. The acoustic transducer converts energy between electrical energy and acoustic energy. The energy storage device stores the electrical energy converted by the acoustic transducer and supplies the electrical energy to support the operation of the pressure sensor. In this manner, acoustic energy from an external source can be received and converted into electrical energy used to power the pressure sensor. Similarly, an electrical signal output from the pressure sensor can be converted into acoustic energy and transmitted to an external source.

Figure 44:
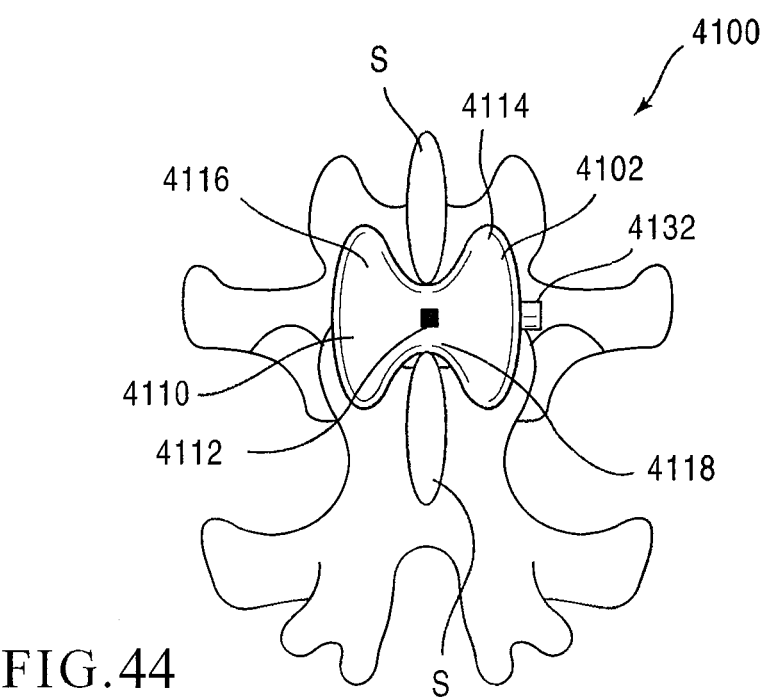

At times, the spinal implant 4100 may need to be repositioned. Such repositioning can be required, for example, to optimize the lateral position of the support portion 4118 during the insertion process. In other instances, the spinal implant 4100 can require repositioning subsequent to the insertion process to accommodate changes in the conditions of the patient. In yet other instances, the spinal implant 4100 can be removed from the patient. To allow for such repositioning and/or removal, the spinal implant is repeatably positionable in the first configuration, the second configuration and/or the third configuration. In FIG. 42, for example, the expandable member 4102 is contracted to the third configuration by removing all or a portion of the fluid contained in the inner area, as described above. In this manner, the spinal implant 4100 can be repositioned in a lateral direction, as indicated by the arrow. Once in the desired position, the expandable member is reexpanded to the second condition as described above. Finally, as shown in FIG. 44, the expansion tool 4130 is removed from the valve 4132.

Figure 45:
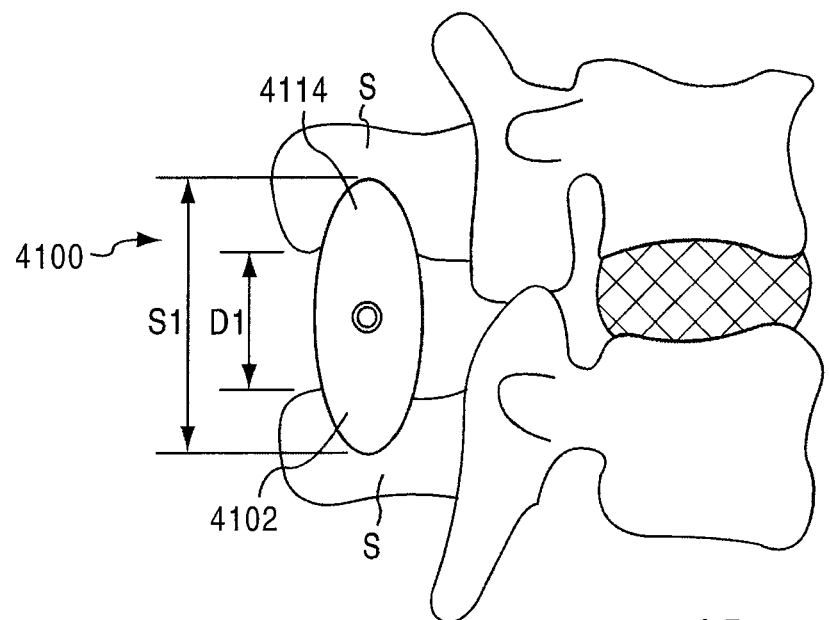
FIG. 45 is a lateral view of the medical device illustrated in FIGS. 39-44 inserted between adjacent spinous processes in a second configuration.

FIG. 45 is a lateral view of the spinal implant 4100 illustrated in FIGS. 39-44 inserted between adjacent spinous processes S in a second configuration. Although FIG. 45 only shows the proximal retention portion 4114 of the expandable member 4102, it should be understood that the distal retention portion 4116 has characteristics and functionality similar to those described below for proximal retention portion 4114. As illustrated, the proximal retention portion 4114 has a size S1 that is greater than the vertical distance D1 between the spinous processes S. In this manner, the proximal retention portion 4114 and the distal retention portion 4116 limit the lateral movement of the spinal implant 4100 when in the second configuration, as discussed above.

Figure 46:
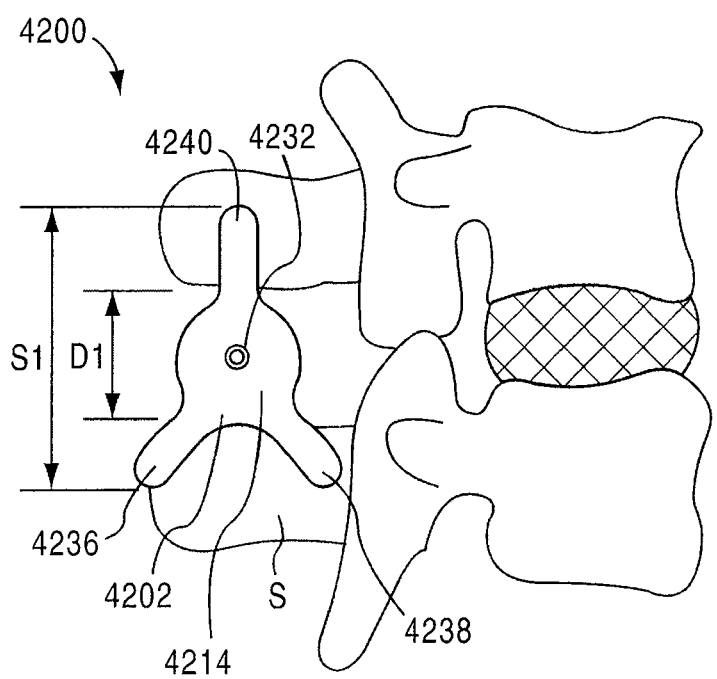
FIG. 46 is a lateral view of a medical device according to an embodiment of the invention inserted between adjacent spinous processes in a second configuration.

FIG. 46 is a lateral view of a spinal implant 4200 according to an embodiment of the invention inserted between adjacent spinous processes and in a second configuration. Similar to the spinal implant 4100 discussed above, the spinal implant 4200 includes an expandable member 4202 and a valve 4232. The expandable member 4202 has a support portion (not shown), a proximal retention portion 4214 and a distal retention portion (not shown). The expandable member 4202 is repeatably positionable in a first configuration, a second configuration and/or a third configuration. When in each configuration, the expandable member 4202 has an associated volume, as discussed above.

In the illustrated embodiment, the proximal retention portion 4214 of the expandable member 4202 has a first radial extension 4236, a second radial extension 4238 and a third radial extension 4240. As illustrated, the distance S1 between the ends of the radial extensions is greater than the vertical distance D1 between the spinous processes S. In this manner, the proximal retention portion 4214 and the distal retention portion limit the lateral movement of the spinal implant 4200 when in the second configuration. In some embodiments, the proximal retention portion and the distal retention portion can assume a variety of different shapes.

Figure 47:
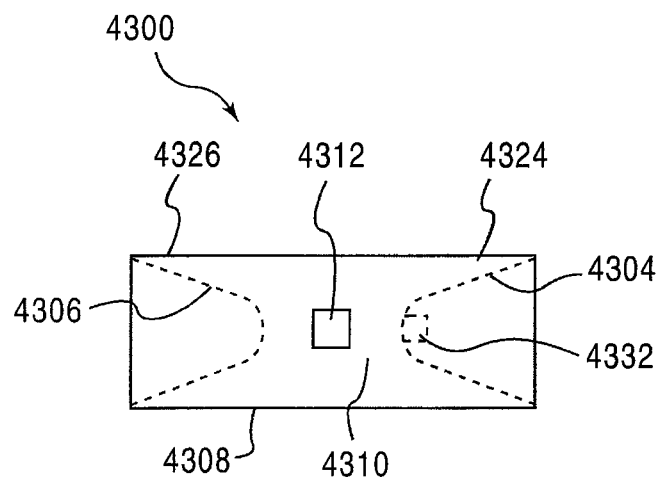
FIGS. 47 and 48 are front views of a medical device according to an embodiment of the invention in a first configuration and a second configuration, respectively.
Figure 48:
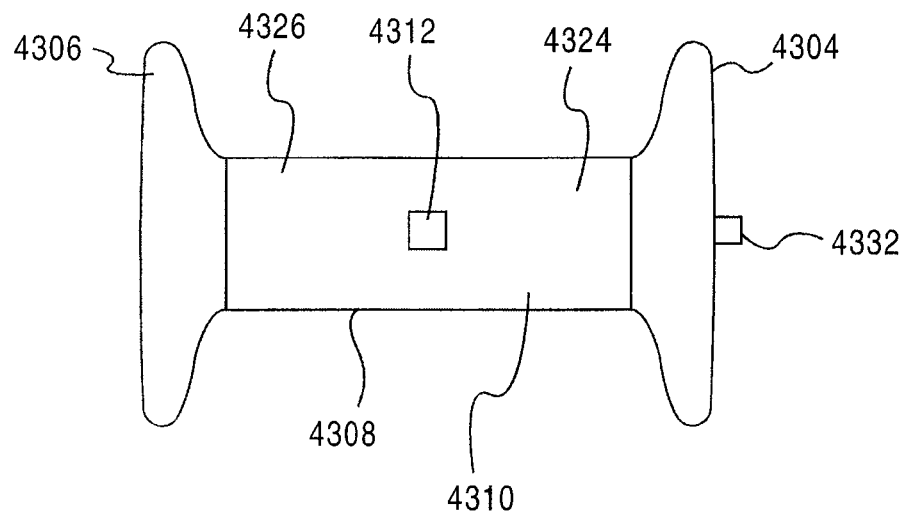

FIGS. 47 and 48 are front views of a spinal implant 4300 according to an embodiment of the invention in a first configuration and a second configuration, respectively. The spinal implant 4300 includes a proximal expandable member 4304, a distal expandable member 4306, a support member 4308, a sensor 4312 and a valve 4332. The support member 4308 has an inner area (not shown) and an outer surface 4310. The outer surface 4310 is configured to contact the spinous processes (not shown). In some embodiments, the support member 4308 distracts the adjacent spinous processes. In other embodiments, the support member 4308 does not distract the adjacent spinous processes. In yet other embodiments, the engagement of the spinous processes by the support member 4308 is not continuous, but occurs upon spinal extension.

The support member 4308 has a proximal portion 4324, to which the proximal expandable member 4304 is coupled, and a distal portion 4326, to which the distal expandable member 4306 is coupled. The proximal expandable member 4304 and the distal expandable member 4306 are each repeatably positionable in a first configuration (FIG. 47) and a second configuration (FIG. 48). As described above, the first configuration represents a substantially contracted condition in which the proximal expandable member 4304 and the distal expandable member 4306 each have a minimal volume. When the spinal implant 4300 is in the first configuration, it can be inserted, repositioned and/or removed. In the illustrated embodiment, the proximal expandable member 4304 and the distal expandable member 4306 are each contained within the inner area of the support member 4308 when the spinal implant 4300 is in the first configuration. In some embodiments, the proximal expandable member 4304 and the distal expandable member 4306 are not contained within the support member 4308.

Conversely, the second configuration represents an expanded condition in which the proximal expandable member 4304 and the distal expandable member 4306 each have a large volume. When the spinal implant 4300 is in the second configuration, the proximal expandable member 4304 and the distal expandable member 4306 each have a size that is greater than the vertical distance between the spinous processes, as described above. In this manner, the proximal expandable member 4304 and the distal expandable member 4306 engage the spinous processes, thereby limiting the lateral movement of the spinal implant 4300.

The proximal expandable member 4304 and the distal expandable member 4306 are expanded into the second configuration by conveying a fluid (not shown) from an area outside of each expandable member 4304, 4306 to an inner area defined by each expandable member 4304, 4306. The fluid is conveyed through a valve 4332, as described above. In the illustrated embodiment, the inner area of the proximal expandable member 4304, the inner area of the distal expandable member 4306 and the inner area of the support member 4308 are in fluid communication with each other to form a single inner area. As such, the fluid can be conveyed to both the inner area of the proximal expandable member 4304 and the inner area of the distal expandable member 4306 by a single valve 4332. In some embodiments, the inner areas of the proximal expandable member 4304 and the distal expandable member 4306 are not in fluid communication. In such an arrangement, each expandable member can be independently transformed between configurations.

The support member 4308 can be made from any number of biocompatible materials, such as, for example, stainless steel, plastic, polyetheretherketone (PEEK), carbon fiber, ultra-high molecular weight (UHMW) polyethylene, and the like. The material of the support member 4308 can have a tensile strength similar to or higher than that of bone. In some embodiments, the support member 4308 is substantially rigid. In other embodiments, the support member 4308 or portions thereof is elastically deformable, thereby allowing it to conform to the shape of the spinous processes. In yet other embodiments, the support member 4308 includes a radiopaque material, such as bismuth, to facilitate tracking the position of the spinal implant 4300 during insertion and/or repositioning.

The proximal expandable member 4304 and the distal expandable member 4306 can be made from any number of biocompatible materials, as discussed above. The proximal expandable member 4304 and the distal expandable member 4306 can be coupled to the support member by an suitable means, such as a biocompatible adhesive.

In the illustrated embodiment, the spinal implant 4300 includes a sensor 4312 coupled to the support member 4308.

As described above, the sensor 4312 can be configured to measure multiple force quantities and/or a pressure of the fluid contained within the proximal expandable member 4304 and the distal expandable member 4306.

Although the spinal implants 4100, 4200 and 4300 are shown and described above as be movable from a retracted configuration to an expanded configuration by conveying a fluid to an inner area of an expandable member, in some embodiments, an implant can be configured to receive any suitable substance to move from a retracted configuration to an expanded configuration. For example, in some embodiments, an implant can include an expandable portion configured to receive a mixture of solid particles contained within a carrier fluid (e.g., a slurry). In other embodiments, an implant can include an expandable portion configured to be filled solely with solid particles to move from a retracted configuration to an expanded configuration. In this manner, the solid particles can form a substrate within the expandable portion that is incompressible and/or more rigid than a liquid or gas.

The solid particles can be of any suitable size and/or shape. In some embodiments, for example, the solid particles can be approximately spherical particles having a diameter of between 0.010 mm and 0.100 mm. In other embodiments, the solid particles can include one or more flat surfaces. In yet other embodiments, the solid particles can be irregularly shaped.

The solid particles can be constructed from any suitable biocompatible material, such as, for example, PET, Nylons, cross-linked Polyethylene, Polyurethanes, and PVC. In some embodiments, the solid particles can be substantially inelastic, thereby forming a low-compliant substrate within the expandable portion of the implant. In other embodiments, the solid particles can have a higher elasticity, thereby forming a high-compliant filler within the expandable portion of the implant. In yet other embodiments, the solid particles can be constructed from a combination of materials such that the characteristics of the filler within the expandable portion of the implant can vary spatially.

Similarly, in some embodiments, the solid particles can be constructed from a material having a high rigidity (i.e., a high shear modulus). In this manner, the solid particles can form a substrate within the expandable portion that has a high resistance to deformation when exposed to a shear stress. In other embodiments, the solid particles can be constructed from a material having a low rigidity. In such embodiments, for example, the solid particles can form a substrate with the expandable portion that can deform when compressed during extension of the spinal column.

In some embodiments, the materials from which the solid particles and the expandable portion are constructed can be selected cooperatively such that the implant, when filled, has suitable strength, rigidity, elasticity and the like. For example, in some embodiments, an implant includes an expandable portion constructed from a low-compliant material that is configured to be expanded by flexible solid particles. In other embodiments, an implant includes an expandable portion constructed from a low-compliant material that is configured to be expanded by rigid solid particles. In yet other embodiments, an implant includes an expandable portion constructed from a high-compliant material that is configured to be expanded by flexible solid particles. In yet other embodiments, an implant includes an expandable portion constructed from a high-compliant material that is configured to be expanded by rigid solid particles.

In some embodiments, the solid particles and/or mixture of solid particles and carrier fluid can be conveyed into and/or removed from the expandable portion of the implant by an expansion tool and via a valve, as described above. In other embodiments, the solid particles and/or mixture of solid particles and carrier fluid can be removed from the expandable portion of the implant by puncturing the expandable portion and applying a vacuum to withdraw the solid particles and/or mixture of solid particles and carrier fluid. In yet other embodiments, the solid particles and/or mixture of solid particles and carrier fluid can be removed from the expandable portion of the implant by puncturing the expandable portion and applying a pressure against an outer portion of the expandable portion to cause the solid particles and/or mixture of solid particles and carrier fluid to be expelled within the body.

In some embodiments, the solid particles can be configured to absorb liquid to expand the expandable portion of an implant. For example, in some embodiments, an expandable portion of an implant can include solid particles constructed from a hydrogel. When the implant is disposed between adjacent spinous processes, a liquid can be conveyed to the expandable portion of the implant, which is then absorbed by the hydrogel particles. Accordingly, the size of the hydrogel particles will increase, thereby expanding the expandable portion of the implant.

Similarly, in some embodiments, a kit can include an implant having an expandable portion, multiple sets of solid particles, and multiple different liquids. The different sets of solid particles can have different characteristics, such as, for example, a size, a shape, and/or an absorption coefficient. Similarly, the different liquids can have different characteristics, such as, for example, viscosity, density and/or an absorption coefficient. In this manner, a user can select a particular set of particles for inclusion in the expandable portion of the implant and a particular liquid for use in expanding the solid particles.

Figure 49:
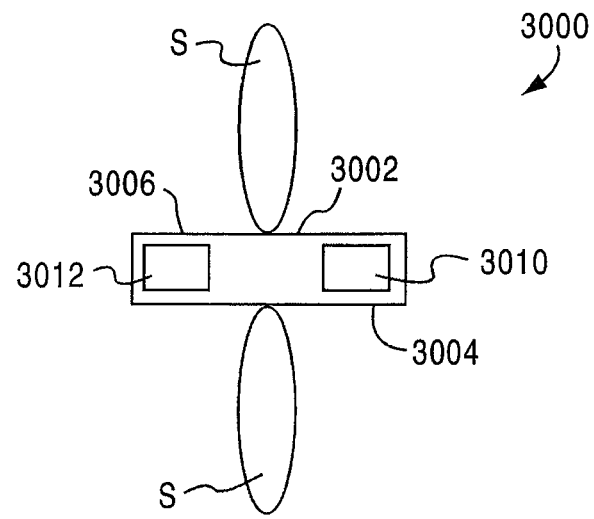
FIG. 49 is a schematic illustration of a posterior view of a medical device according to an embodiment of the invention in a first configuration disposed between two adjacent spinous processes.
Figure 50:
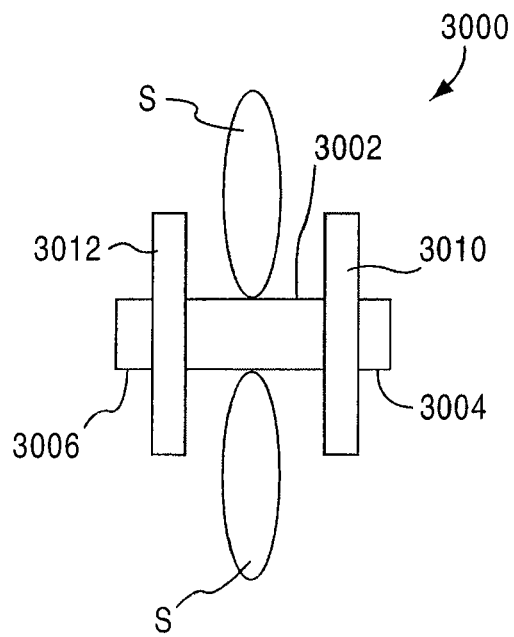
FIG. 50 is a schematic illustration of a posterior view of a medical device according to an embodiment of the invention in a second configuration disposed between two adjacent spinous processes.

FIGS. 49 and 50 are schematic illustrations of a posterior view of a medical device 3000 according to an embodiment of the invention disposed between two adjacent spinous processes S in a first configuration and a second configuration, respectively. The medical device 3000 includes a support member 3002, a proximal retention member 3010 and a distal retention member 3012. The support member 3002 has a proximal portion 3004 and a distal portion 3006, and is configured to be disposed between the spinous processes S to prevent over-extension/compression of the spinous processes S. In some embodiments, the support member 3002 distracts the adjacent spinous processes S. In other embodiments, the support member 3002 does not distract the adjacent spinous processes S.

The proximal retention member 3010 has a first configuration in which it is substantially disposed within the proximal portion 3004 of the support member 3002, as illustrated in FIG. 49. Similarly, the distal retention member 3012 has a first configuration in which it is substantially disposed within the distal portion 3006 of the support member 3002. When the proximal retention member 3010 and the distal retention member 3012 are each in their respective first configuration, the medical device 3000 can be inserted between the adjacent spinous processes S.

The proximal retention member 3010 can be moved from the first configuration to a second configuration in which a portion of it is disposed outside of the support member 3002, as illustrated in FIG. 50. Similarly, the distal retention member 3012 can be moved from the first configuration to a second configuration. When each is in their respective second configuration, the proximal retention member 3010 and the distal retention member 3012 limit lateral movement of the support member 3002 with respect to the spinous processes S by contacting the spinous processes S (i.e., either directly or through surrounding tissue). For purposes of clarity, the tissue surrounding the spinous processes S is not illustrated.

In use, the adjacent spinous processes S can be distracted prior to inserting the medical device 3000 into the patient. When the spinous processes S are distracted, a trocar (not shown in FIG. 49 or 50) can be used to define an access passageway (not shown in FIGS. 49 and 50) for the medical device 3000. In some embodiments, the trocar can be used to define the passage as well as to distract the spinous processes S.

Once an access passageway is defined, the medical device 3000 is inserted percutaneously and advanced, distal portion 3006 first, between the spinous processes S. The medical device 3000 can be inserted from the side of the spinous processes S (i.e., a posterior-lateral approach). The use of a curved shaft assists in the use of a lateral approach to the spinous processes S. Once the medical device 3000 is in place between the spinous processes S, the proximal retention member 3010 and the distal retention member 3012 are moved to their second configurations, either serially or simultaneously. In this manner, lateral movement of the support member 3002 with respect to the spinous processes S is limited.

When it is desirable to change the position of the medical device 3000, the proximal retention member 3010 and the distal retention member 3012 are moved back to their first configurations, thereby allowing the support member 3002 to be moved laterally. Once the support member 3002 is repositioned, the medical device 3000 can be returned to the second configuration. Similarly, when it is desirable to remove the medical device 3000, proximal retention member 3010 and the distal retention member 3012 are moved to their first configurations, thereby allowing the support member 3002 to be removed.

In some embodiments, the medical device 3000 is inserted percutaneously (i.e., through an opening in the skin) and in a minimally-invasive manner. For example, as discussed in detail herein, the overall sizes of portions of the medical device 3000 can be increased by moving the proximal retention member 3010 and the distal retention member 3012 to their respective second configurations after the medical device 3000 is inserted between the adjacent spinous processes S. When in the expanded second configuration, the sizes of portions of the medical device 3000 can be greater than the size of the opening. For example, the size of the opening/incision in the skin can be between 3 millimeters in length and 25 millimeters in length across the opening. In some embodiments, the size of the medical device 3000 in the expanded second configuration is between 3 and 25 millimeters across the opening.

Figure 51:
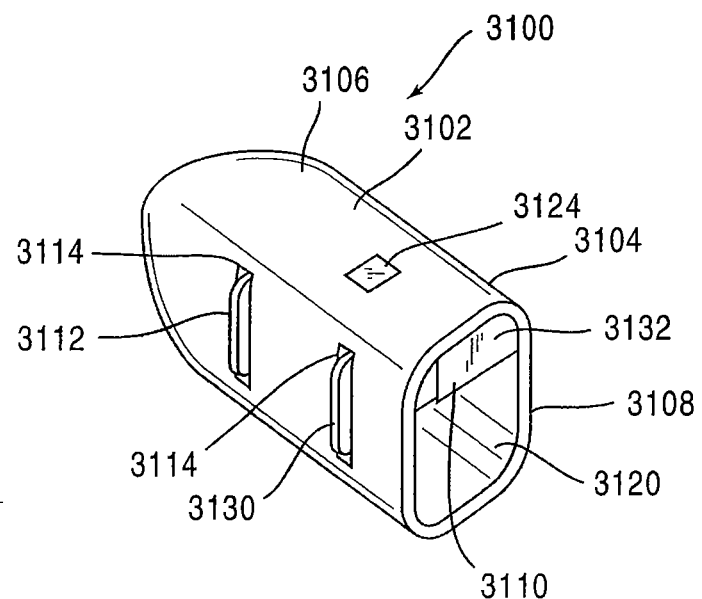
FIGS. 51 and 52 are perspective views of a medical device according to an embodiment of the invention in a first configuration and a second configuration, respectively.
Figure 52:
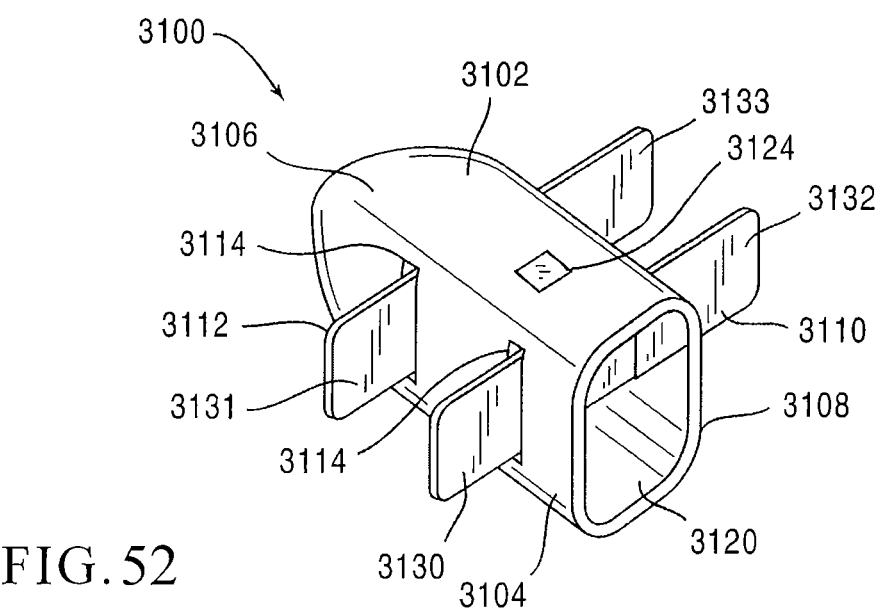
Figure 53:
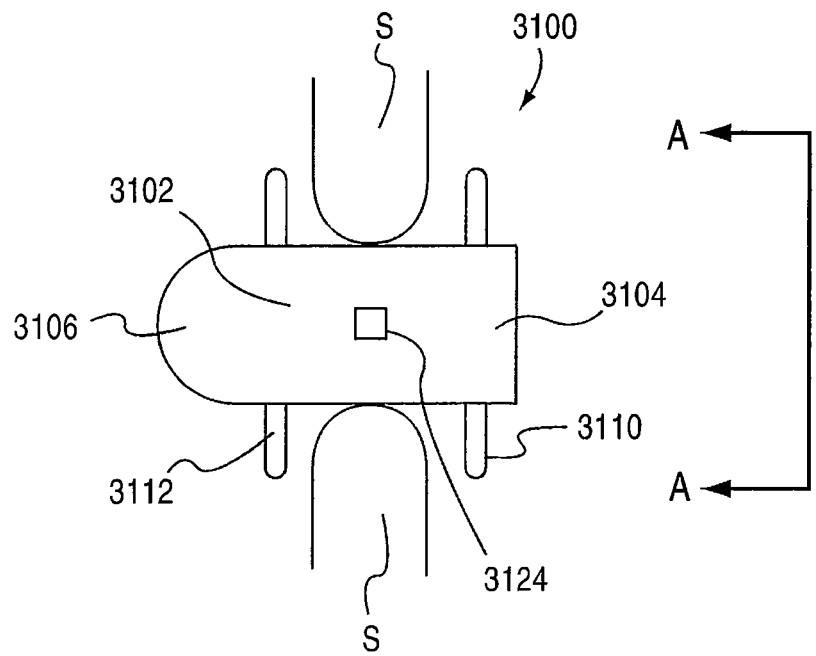
FIG. 53 is a posterior view of the medical device illustrated in FIGS. 51 and 52 disposed between adjacent spinous processes in a second configuration.
Figure 54:
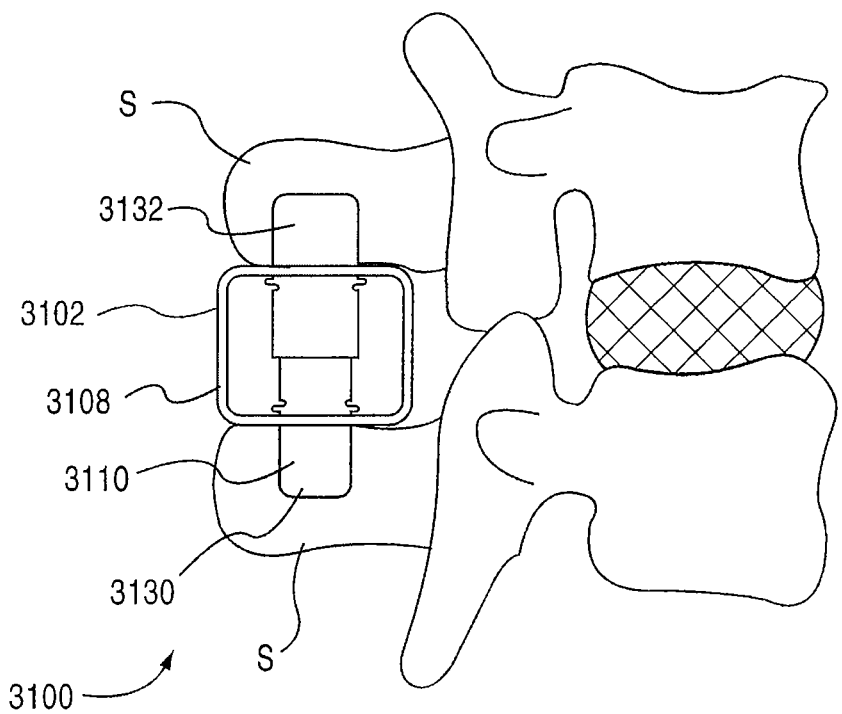
FIG. 54 is a lateral view taken from a proximal perspective A-A of the medical device illustrated in FIG. 53 disposed between adjacent spinous processes in a second configuration.

FIGS. 51-56 illustrate a spinal implant 3100 according to an embodiment of the invention. FIGS. 51 and 52 are perspective views of the spinal implant 3100 in a first configuration and a second configuration, respectively. The spinal implant 3100 includes a support member 3102, a proximal retention member 3110 and a distal retention member 3112. The support member 3102 is positioned between adjacent spinous processes S, as illustrated in FIGS. 53 and 54. As shown in FIGS. 51 and 52, the proximal retention member 3110 and the distal retention member 3112 are each repeatably positionable in a first configuration in which they are substantially disposed within the support member 3102 (FIG. 51), and a second configuration in which a portion of each retention member 3110, 3112 is disposed outside of the support member 3102 (FIG. 52). When the spinal implant 3100 is in the first configuration, it can be inserted between the adjacent spinous processes S, repositioned between the adjacent spinous processes and/or removed from the patient. When the spinal implant 3100 is in the second configuration, its lateral movement is limited, thereby allowing the desired position of the support member 3102 to be maintained.

In some embodiments, the support member 3102 distracts the adjacent spinous processes S. In other embodiments, the support member 3102 does not distract the adjacent spinous processes S. In yet other embodiments, the engagement of the spinous processes S by the support member 3102 is not continuous, but occurs upon spinal extension.

The support member 3102 can be made from any number of biocompatible materials, such as, for example, stainless steel, plastic, polyetheretherketone (PEEK), carbon fiber, ultra-high molecular weight (UHMW) polyethylene, and the like. The material of the support member 3102 can have a tensile strength similar to or higher than that of bone. In some embodiments, the support member 3102 is substantially rigid. In other embodiments, the support member 3102 or portions thereof is elastically deformable, thereby allowing it to conform to the shape of the spinous processes. In yet other embodiments, the support member 3102 includes a radiopaque material, such as bismuth, to facilitate tracking the position of the spinal implant 3100 during insertion and/or repositioning.

In the illustrated embodiment, the spinal implant 3100 includes a sensor 3124 coupled to the support member 3102. In some embodiments, the sensor 3124 is a strain gauge sensor that measures a force applied to the support member 3102. In some embodiments, the sensor 3124 can include multiple strain gauges to facilitate measuring multiple force quantities, such as a compressive force and/or a bending moment. In other embodiments, the sensor 3124 is a variable capacitance type pressure sensor configured to measure a force and/or a pressure applied to the support member 3102. In yet other embodiments, the sensor 3124 is a piezoelectric sensor that measures a force and/or a pressure applied to the support member 3102. In still other embodiments, the spinal implant 3100 can include multiple sensors located at various locations to provide a spatial profile of the force and/or pressure applied to the support member 3102. In this manner, a practitioner can detect changes in the patient's condition, such those that may result in a loosening of the spinal implant.

In some embodiments, the sensor 3124 can be remotely controlled by an external induction device. For example, an external radio frequency (RF) transmitter (not shown) can be used to supply power to and communicate with the sensor 3124. In other embodiments, an external acoustic signal transmitter (not shown) can be used to supply power to and communicate with the sensor 3124. In such an arrangement, for example, the sensor can include a pressure sensor, of the types described above, for measuring a pressure; an acoustic transducers, and an energy storage device. The acoustic transducer converts energy between electrical energy and acoustic energy. The energy storage device stores the electrical energy converted by the acoustic transducer and supplies the electrical energy to support the operation of the pressure sensor. In this manner, acoustic energy from an external source can be received and converted into electrical energy used to power the pressure sensor. Similarly, an electrical signal output from the pressure sensor can be converted into acoustic energy and transmitted to an external source.

The support member 3102 includes a sidewall 3108 that defines an inner area 3120 and multiple openings 3114 that connect the inner area 3120 to an area outside of the support member 3102. When the spinal implant 3100 is in the first configuration, the proximal retention member 3110 and the distal retention member 3112 are substantially disposed within the inner area 3120 of the support member 3102, as shown in FIG. 51. When the spinal implant 3100 is in the second configuration, a portion of each of the proximal retention member 3110 and the distal retention member 3112 extends through the openings 3114 to an area outside of the support member 3102. In the second configuration, the proximal retention member 3110 and the distal retention member 3112 engage the adjacent spinous processes, thereby limiting lateral movement of the spinal implant 3100.

Figure 56:
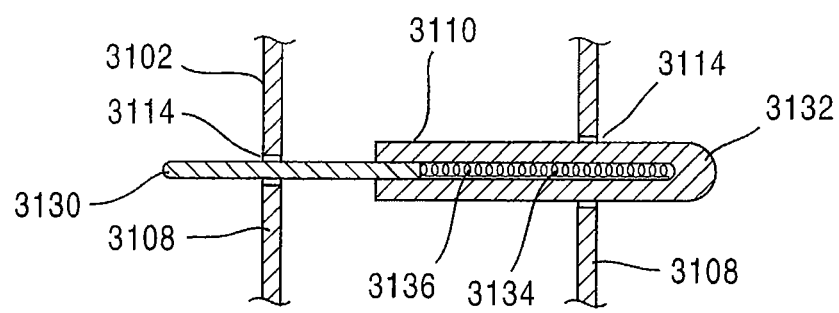
FIG. 56 is a cross-sectional plan view taken along section A-A of the medical device illustrated in FIGS. 51 and 52 in a second configuration.

The proximal retention member 3110 includes a first elongate member 3130 and a second elongate member 3132. Similarly, the distal retention member 3112 includes a first elongate member 3131 and a second elongate member 3133. As illustrated in FIG. 56, which shows is a cross-sectional plan view of the proximal portion 3104 of the support member 3102, the first elongate member 3130 is slidably disposed within a pocket 3134 defined by the second elongate member 3132. A biasing member 3136, such as a spring or an elastic member, is disposed within the pocket 3134 and is coupled to the first elongate member 3130 and the second elongate member 3132. In this manner, the retention members can be biased in the second configuration. In other embodiments, the biasing member 3136 can be configured to bias the retention members in the first configuration. In yet other embodiments, the retention members do not include a biasing member, but instead use other mechanisms to retain a desired configuration. Such mechanisms can include, for example, mating tabs and slots configured to lockably engage when the retention members are in a desired configuration.

In use, the spinal implant 3100 is positioned in the first configuration during insertion, removal or repositioning. As discussed above, the spinal implant 3100 is inserted percutaneously between adjacent spinous processes. The distal portion 3106 of the support member 3102 is inserted first and is moved past the spinous processes until the support member 3102 is positioned between the spinous processes. The support member 3102 can be sized to account for ligaments and tissue surrounding the spinous processes S. In some embodiments, the support member 3102 contacts the spinous processes between which it is positioned during a portion of the range of motion of the spinous processes S. In some embodiments, the support member 3102 of spinal implant 3100 is a fixed size and is not compressible or expandable. In yet other embodiments, the support member 3102 can compress to conform to the shape of the spinous processes S. Similarly, in some embodiments, the proximal retention member 3110 and the distal retention member 3112 are substantially rigid. In other embodiments, the retention members or portions thereof are elastically deformable, thereby allowing them to conform to the shape of the spinous processes.

Figure 55:
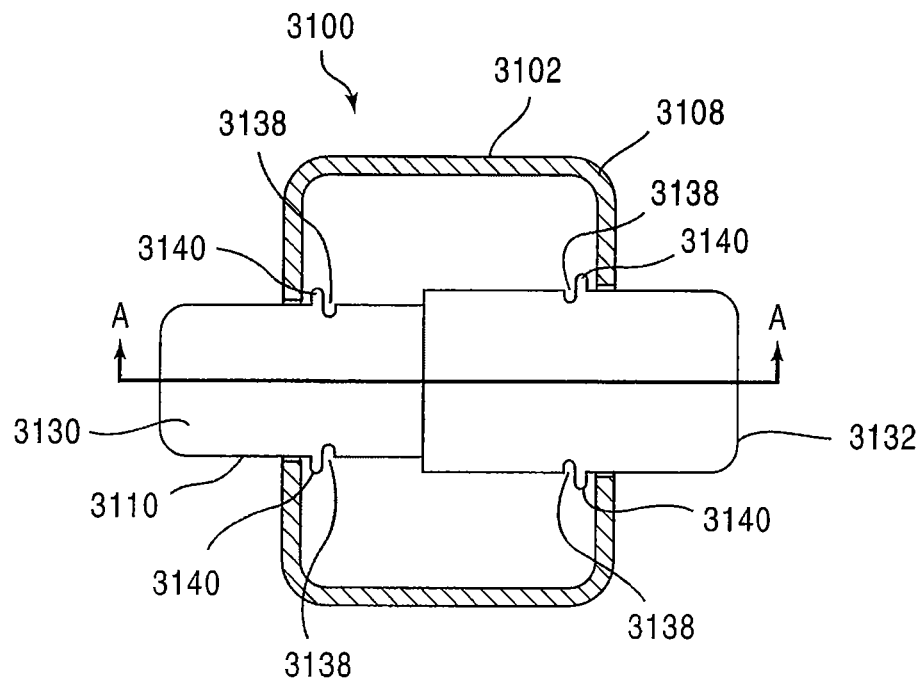
FIG. 55 is a cross-sectional front view of the medical device illustrated in FIGS. 51 and 52 in a second configuration.

In the illustrated embodiment, the spinal implant 3100 is held in the first configuration by an insertion tool (not shown) that overcomes the force exerted by the biasing member 3136, thereby disposing a portion of the first elongate member 3130 within the pocket 3134 of the second elongate member 3132. In this manner, the spinal implant 3100 can be repeatedly moved from the first configuration to the second configuration, thereby allowing it to be repositioned and/or removed percutaneously. As illustrated in FIG. 55, the first elongate member 3130 and the second elongate member 3132 each include notches 3138 configured to receive a portion of the insertion tool. When the insertion tool is released, the biasing member 3136 is free to extend, thereby displacing a portion of the first elongate member 3130 out of the pocket 3134 of the second elongate member 3132. In this manner, portions of both the first elongate member 3130 and the second elongate member 3132 are extended through the adjacent openings 3114 and to an area outside of the support member 3102. In some embodiments, the proximal retention member 3110 and the distal retention member 3112 are transitioned between their respective first and second configurations simultaneously. In other embodiments, the proximal retention member 3110 and the distal retention member 3112 are transitioned between their first and second configurations serially.

As illustrated, the first elongate member 3130 and the second elongate member 3132 each include one or more tabs 3140 that engage the side wall 3108 of the support member 3102 when in the second configuration, thereby ensuring that the first and second elongate members remain coupled to each other and that portions of the first and second elongate members remain suitably disposed within the support member 3102. In other embodiments, the first elongate member 3130 and the second elongate member 3132 are coupled to each other by other suitable mechanisms, such as mating tabs and slots configured to engage when the retention member reaches a predetermined limit of extension.

Figure 57:
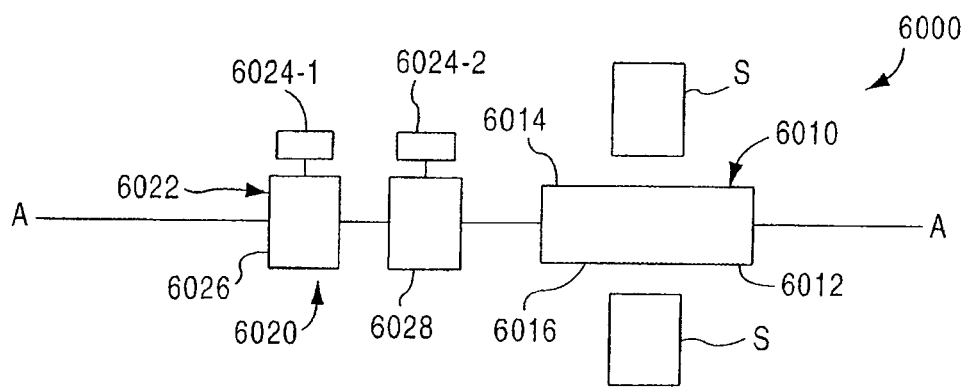
FIG. 57 is a schematic illustration of a medical device according to an embodiment of the invention in a collapsed configuration adjacent two spinous processes.
Figure 58:
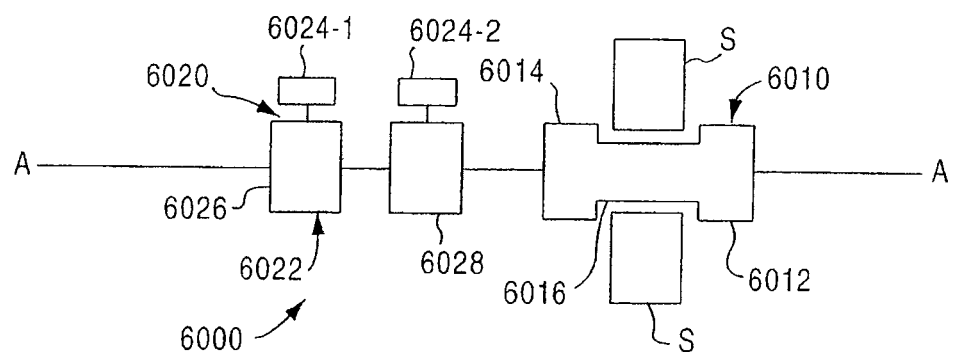
FIG. 58 is a schematic illustration of the medical device of FIG. 57 in an expanded configuration adjacent two spinous processes.

FIGS. 57 and 58 are schematic illustrations of a medical device according to an embodiment of the invention positioned between two adjacent spinous processes. FIG. 57 illustrates the medical device in a first configuration, and FIG. 58 illustrates the medical device in a second configuration. The medical device 6000 includes an implant 6010 and a deployment tool 6020. The implant 6010 includes a distal portion 6012, a proximal portion 6014, and a central portion 6016. The implant 6010 is configured to be inserted between adjacent spinous processes S. The central portion 6016 is configured to contact and provide a minimum spacing between the spinous processes S when adjacent spinous processes S move toward each other during their range of motion to prevent over-extension/compression of the spinous processes S. In some embodiments, the central portion 6016 does not substantially distract the adjacent spinous processes S. In other embodiments, the central portion 6016 does distract the adjacent spinous processes S. The implant 6010 and the deployment tool 6020 can each be inserted into a patient's back and moved in between adjacent spinous processes from the side of the spinous processes (i.e., a posterior-lateral approach). The use of a curved insertion shaft assists in the use of a lateral approach to the spinous processes S.

The implant 6010 has a collapsed configuration in which the proximal portion 6014, the distal portion 6012 and the central portion 6016 share a common longitudinal axis. In some embodiments, the proximal portion 6014, the distal portion 6012 and the central portion 6016 define a tube having a constant inner diameter. In other embodiments, the proximal portion 6014, the distal portion 6012 and the central portion 6016 define a tube having a constant outer diameter and/or inner diameter. In yet other embodiments, the proximal portion 6014, the distal portion 6012 and/or the central portion 6016 have different inner diameters and/or outer diameters.

The implant 6010 can be moved from the collapsed configuration to an expanded configuration, as illustrated in FIG. 58. In the expanded configuration, the proximal portion 6014 and the distal portion 6012 each have a larger outer perimeter (e.g., outer diameter) than when in the collapsed configuration, and the proximal portion 6014 and the distal portion 6012 each have a larger outer perimeter (e.g., outer diameter) than the central portion 6016. In the expanded configuration, the proximal portion 6014 and the distal portion 6012 are positioned to limit lateral movement of the implant 6010 with respect to the spinous processes S. The proximal portion 6014 and the distal portion 6012 are configured to engage the spinous process (i.e., either directly or through surrounding tissue and depending upon the relative position of the adjacent spinous processes S) in the expanded configuration. For purposes of clarity, the tissue surrounding the spinous processes S is not illustrated.

In some embodiments, the proximal portion 6014, the distal portion 6012 and the central portion 6016 are monolithically formed. In other embodiments, one or more of the proximal portion 6014, the distal portion 6012 and/or the central portion 6016 are separate components that can be coupled together to form the implant 6010. For example, the proximal portion 6014 and distal portion 6012 can be monolithically formed and the central portion 6016 can be a separate component that is coupled thereto. These various portions can be coupled, for example, by a friction fit, welding, adhesive, etc.

The implant 6010 is configured to be coupled to the deployment tool 6020. The deployment tool 6020 includes an elongate member 6022 and two or more engaging portions 6024. In the embodiment shown in FIGS. 57 and 58, there are two engaging portions 6024-1 and 6024-2 shown, but it should be understood that more than two engaging portions 6024 can be included. The elongate member 6022 can include a first body portion 6026 coupled to a second body portion 6028. In some embodiments, the first body portion 6026 is threadedly coupled to the second body portion 6028. The first body portion 6026 and the second body portion 6028 are configured to be moved relative to each other. For example, a threaded connection between the first body portion 6026 and the second body portion 6028 can be used to decrease or increase a distance between the first body portion 6026 and the second body portion 6028. The first body portion 6026 and the second body portion 6028 can be a variety of different shapes and sizes, and can be the same shape and/or size, or have a different shape and/or size than each other. For example, in some embodiments, the first body portion includes a straight distal end and a straight proximal end, and the second body portion includes a straight proximal end and a curved or rounded distal end. The curved distal end can assist with the insertion of the deployment tool into a lumen of an implant and also with the insertion of the medical device into a portion of a patient's body.

The first engaging portion 6024-1 can be coupled to the first body portion 6026 and the second engaging portion 6024-2 can be coupled to the second body portion 6028. The engaging portions 6024 can be, for example, substantially rectangular, square, circular, oval, semi-circular, or quarter-moon shaped. The engaging portions 6024, can be spring-loaded devices coupled to the elongate member 6022 of the deployment tool 6020, such that the engaging portions 6024 are biased into a position transverse to a longitudinal axis A defined by the elongate member 6022 and extending from an outer surface of the elongate member 6022. Upon force exerted on the engaging portions 6024, the engaging portions 6024 can be moved or collapsed to a position substantially below the outer surface of the elongate member 6022. The engaging portions 6024 can alternatively be coupled to an actuator (not shown) configured to move the engaging portions 6024 from a position transverse to the longitudinal axis A and extending from an outer surface of the elongate member 6022, to a position substantially below the outer surface of the elongate member 6022.

Figure 59:
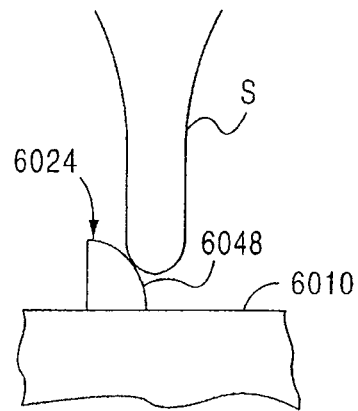
FIG. 59 is a side view of a portion of a medical device including an engaging portion in an extended configuration, according to an embodiment of the invention, positioned adjacent a spinous process.
Figure 60:
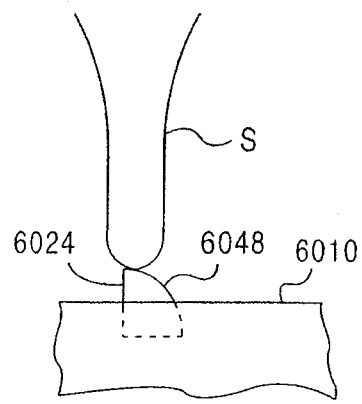
FIG. 60 is a side view of the portion of the medical device of FIG. 59 including the engaging portion in a partially collapsed configuration.
Figure 61:
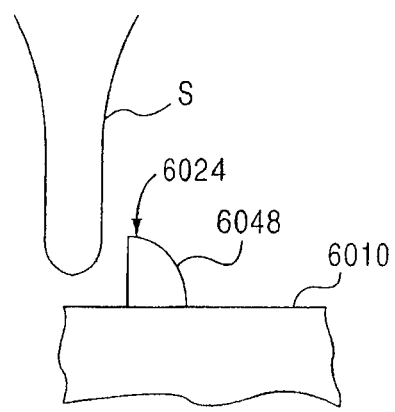
FIG. 61 is a side view of the portion of the medical device of FIG. 59 including the engaging portion in the extended configuration after being inserted past the spinous process.

FIGS. 59-61 illustrate the movement of an engaging portion 6024 as it passes by a spinous process S when an implant and deployment tool (collectively also referred to as medical device) are coupled together and being inserted between adjacent spinous processes. In some cases, as the medical device is being inserted, an engaging portion 6024 extending from a proximal portion of an implant may come into contact with a spinous process (or other tissue). To allow the engaging portion 6024 to pass by the spinous process, the engaging portion 6024 can be moved downward (as described above) so as to clear the spinous process. FIG. 59 illustrates an engaging portion 6024 having a spring-biased construction. The engaging portion 6024 includes a curved portion 6048 that initially contacts the spinous process S as the medical device is being inserted adjacent a spinous process S. As the curved portion 6048 contacts the spinous process S, the engaging portion 6024 is moved downward at least partially into an interior of the implant 6010, as shown in FIG. 60. The engaging portion 6024 moves back to an extended position (e.g., extending transversely from a surface of the implant 6010) after the engaging portion clears the spinous process S, as shown in FIG. 61, due to the bias of the spring (not shown).

Figure 62:
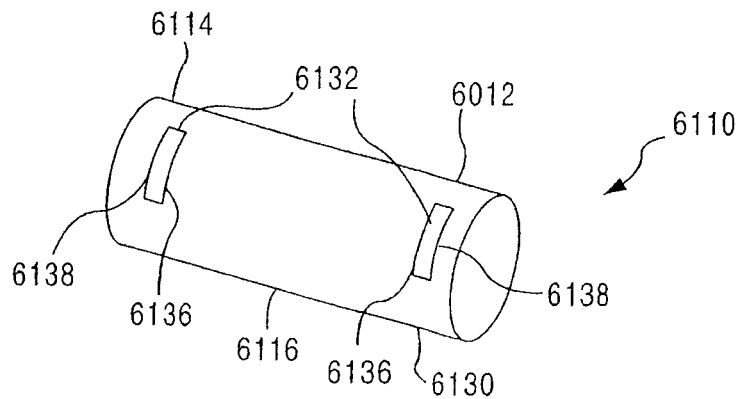
FIG. 62 is a side perspective view of an implant according to an embodiment of the invention in an expanded configuration.
Figure 72:
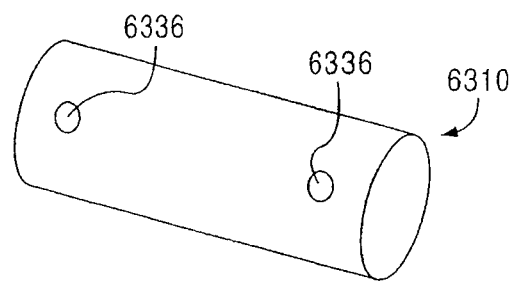
FIG. 72 is a side perspective view of an implant according to another embodiment of the invention.

The deployment tool 6020 can be used to move the implant 6010 from the collapsed configuration to the expanded configuration, and vice versa, as will be discussed in more detail below. The first body portion 6026 and the second body portion 6028 are collectively configured to be inserted at least partially into a lumen (not shown in FIGS. 57 and 58) of the implant 6010, such that at least one engaging portion 6024 extends through an opening (not shown in FIGS. 57 and 58) defined by the implant 6010. The implant 6010 can be configured with one or more such openings, each of which is configured to receive an engaging portion 6024 disposed on the elongate member 6022 (e.g., the first body portion 6026 or the second body portion 6028). The openings defined by the implant 6010 can be, for example, the openings can be circular, oval, square, rectangular, etc. FIG. 62 illustrates an example of an implant 6110 defining curved rectangular openings 6136, and FIG. 72 illustrates an implant 6310 defining curved round or circular openings 6336.

The openings are at least partially defined by an edge (not shown in FIGS. 57 and 58) on the implant 6010. The engaging portions 6024 on the deployment tool 6020 include a surface (not shown in FIGS. 57 and 58) that is configured to engage or contact the edge of the openings of the implant 6010 when the elongate member 6022 is inserted into the lumen of the implant 6010.

In use, the spinous processes S can be distracted prior to inserting the implant 6010. When the spinous processes are distracted, a trocar can be used to define an access passage for the implant 6010. In some embodiments, the trocar can be used to define the passage as well as distract the spinous processes S. Once an access passage is defined, the implant 6010 can be inserted percutaneously and advanced between the spinous processes, distal end 6012 first, until the central portion 6016 is located between the spinous processes S. In some embodiments, the implant 6010 can be coupled to the deployment tool 6020 prior to being inserted between the adjacent spinous processes. In other embodiments, the implant 6010 can be inserted between adjacent spinous processes without being coupled to the deployment tool 6020. In the latter configuration, after the implant 6010 is disposed between the adjacent spinous processes, the deployment tool 6020 can be inserted into the lumen defined by the implant 6010.

Once the implant 6010 is in place between the spinous processes, and the deployment tool 6020 is in position within the lumen of the implant 6010, the implant 6010 can be moved to the second configuration (i.e., the expanded configuration) by actuating the deployment tool 6020. For example, when the deployment tool 6020 is inserted into the lumen of the implant 6010, the first body portion 6026 is positioned at a first distance from the second body portion 6028, and the first engaging portion 6024-1 is positioned at a first distance from the second engaging portion 6024-2, as shown in FIG. 57. The deployment tool 6020 can then be actuated at a proximal end portion (e.g., by turning a handle) (not shown in FIGS. 57 and 58) causing the threaded coupling between the first body portion 6026 and the second body portion 6028 to move the first body portion 6026 and the second body portion 6028 towards each other such that the first body portion 6026 is now at a second distance (closer) from the second body portion 6028, as shown in FIG. 58. This movement likewise moves the first engaging portion 6024-1 and the second engaging portion 6024-2 to a closer position relative to each other. For example, in FIG. 57, the first engaging portion 6024-1 is positioned at a distance from the second engaging portion 6024-2 that is greater than a distance between the first engaging portion 6024-1 and the second engaging portion 6024-2 shown in FIG. 58.

As the engaging portions 6024-1 and 6024-2 are moved relative to each other, the surface (described above and described in more detail below) on the engaging portions 6024 imparts a force on the edge (described above and described in more detail below) of the opening defined by the implant causing the implant to move from the collapsed configuration to the expanded configuration.

The deployment tool 6020 is configured such that the deployment tool 6020 can be removed from the implant 6010 after the implant has been moved to the expanded configuration. The implant can remain disposed between the spinous processes indefinitely or removed as needed. For example, the deployment tool 6020 can be reinserted into the lumen of the implant 6010 and actuated in an opposite direction to cause the implant 6010 to be moved from the expanded configuration back to the collapsed configuration. In the collapsed configuration, the implant can be removed from the patient's body or repositioned to a new location between the spinous processes.

In some embodiments, the implant 6010 is inserted percutaneously (i.e., through an opening in the skin) and in a minimally-invasive manner. For example, as discussed in detail herein, the sizes of portions of the implant are expanded after the implant is inserted between the spinous processes. Once expanded, the sizes of the expanded portions of the implant are greater than the size of the opening. For example, the size of the opening/incision in the skin can be between 3 millimeters in length and 25 millimeters in length across the opening. In some embodiments, the size of the implant in the expanded configuration is between 3 and 25 millimeters across the opening.

Figure 63:
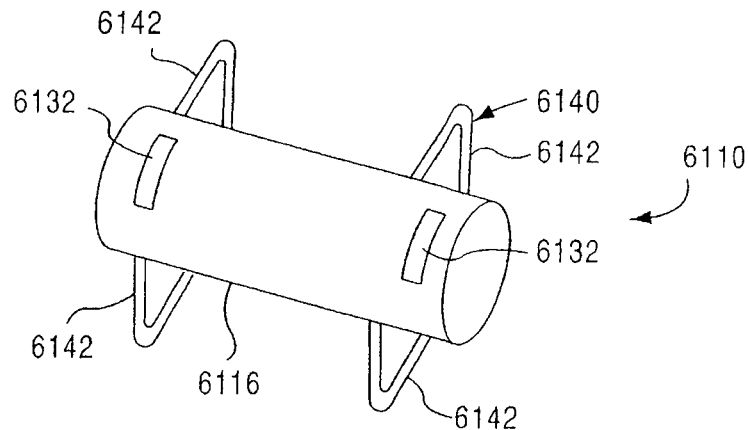
FIG. 63 is a side perspective view of the implant of FIG. 62 shown in a collapsed configuration.
Figure 64:
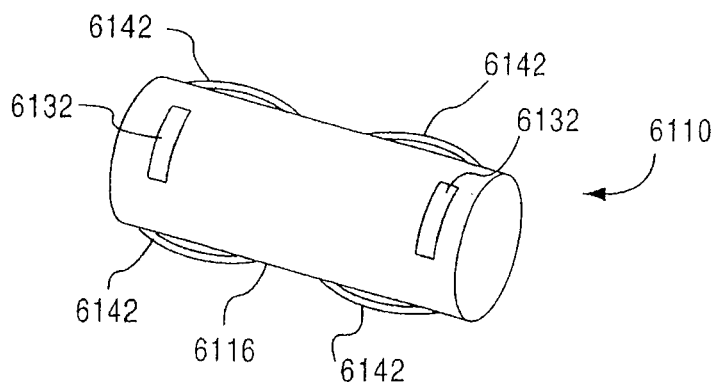
FIG. 64 is a side perspective view of the medical device of FIG. 62 shown in a collapsed configuration.
Figure 71:
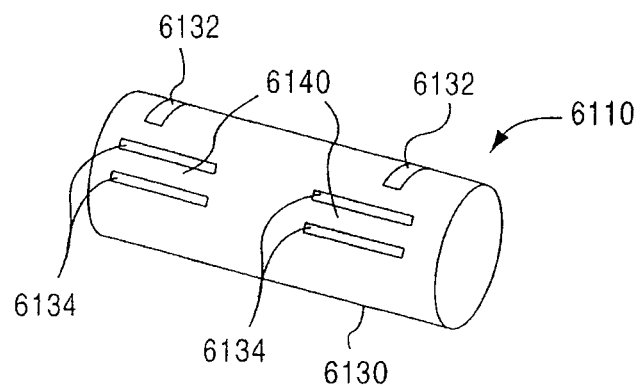
FIG. 71 is a side perspective view of the implant of FIG. 62 shown rotated about a longitudinal axis of the implant.

FIGS. 62-64 illustrate an implant according to an embodiment of the invention. An implant 6110 includes a proximal portion 6114, a distal portion 6112, and a central portion 6116. The implant 6110 also defines multiple openings 6132 on an outer surface of the implant 6110. The openings 6132 are in communication with a lumen 6158 (shown in FIG. 69) defined by the implant 6110. The openings 6132 are partially defined by a first edge 6136 and a second edge 6138. The implant 6110 includes expandable portions disposed at the distal portion 6112 and the proximal portion 6114. The expandable portions 6140 can be coupled to the implant 6110 or formed integral with the implant 6110, as shown in FIG. 71. As shown in FIG. 71, elongated slots 6134 can be defined on an outer surface of the implant 6110. The elongated slots 6134 create weakened areas on the implant 6110 that allow the expandable portions 6140 to fold when exposed to axial force, forming extensions 6142, as shown in FIG. 63.

The implant 6110 can be inserted between adjacent spinous processes (not shown) in a collapsed configuration, as shown in FIG. 62, and then moved to an expanded configuration, as shown in FIG. 63. The implant 6110 can then be moved back to a collapsed configuration as shown in FIG. 64, which illustrates the expandable portions 6140 in a partially collapsed configuration. Although FIG. 64 shows a partially collapsed configuration, in some embodiments, the implant can be moved back to the collapsed configuration as shown in FIG. 62.

Figure 65:
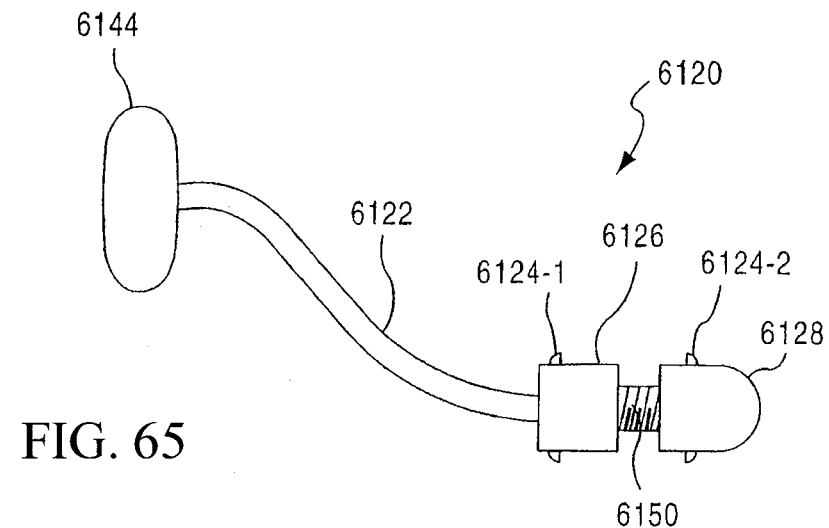
FIG. 65 is a side view of a deployment tool according to an embodiment of the invention.
Figure 66:
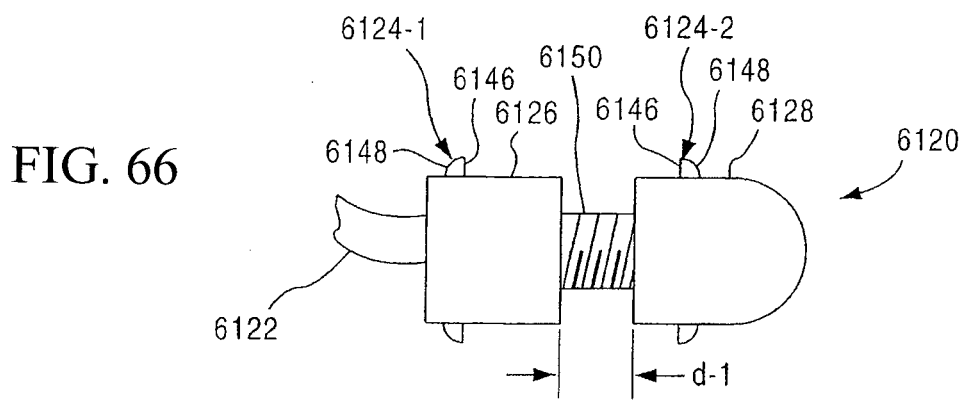
FIG. 66 is a side view of a portion of the deployment tool of FIG. 65 shown in a first configuration.
Figure 67:
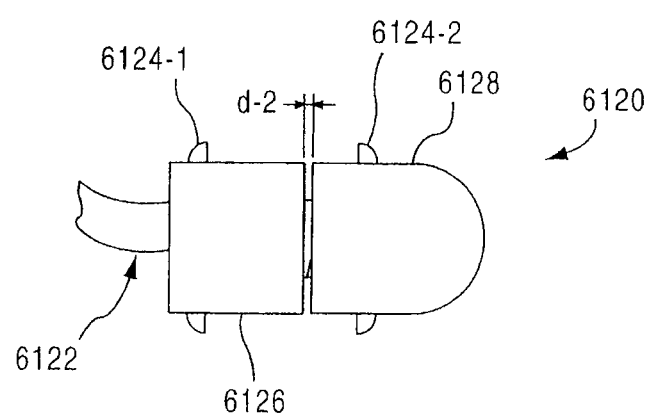
FIG. 67 is a side view of the portion of the deployment tool of FIG. 66 shown in a second configuration.

To move the implant 6110 from the collapsed configuration to the expanded configuration, and vice versa, a deployment tool, as described above and as shown in FIGS. 65-67, can be used. The deployment tool 6120 includes an elongate member 6122 coupled to a handle 6144. The elongate member 6122 includes a first body portion 6126 coupled to a second body portion 6128 through a threaded coupling 6150. A pair of engaging portions 6124-1 are disposed on the first body portion 6126, and a pair of engaging portions 6124-2 are disposed on the second body portion 6128. The engaging portions 6124-1 and 6124-2 (also collectively referred to as engaging portions 6124) include a surface 6146 and a rounded portion 6148. The threaded coupling 6150 between the first body portion 6126 and the second body portion 6128 is used to move the first body portion 6126 and the second body portion 6128 such that a distance between the first body portion 6126 and the second body portion 6128 is changed. For example, FIG. 66 illustrates a first distance d-1 between the first body portion 6126 and the second body portion 6128, and FIG. 67 illustrates a second distance d-2 between the first body portion 6126 and the second body portion 6128. As shown in FIGS. 66 and 67, as the distance between the first body portion 6126 and the second body portion 6128 is changed, a distance between the engaging portions 6124-2 and 6124-2 is also changed.

Figure 68:
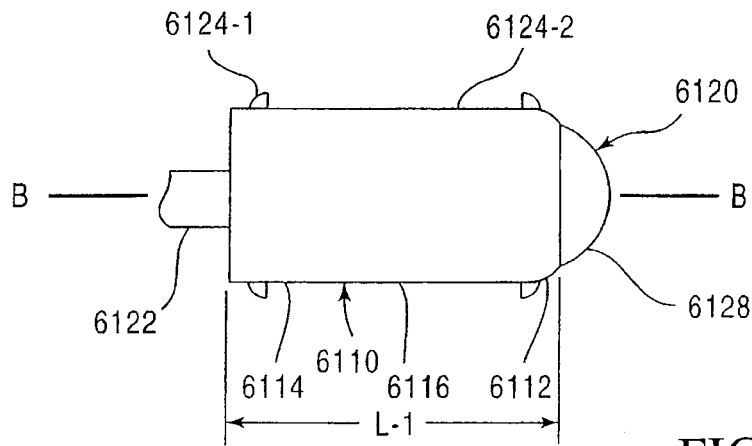
FIG. 68 is a side view of a portion of the deployment tool of FIG. 66 and the implant of FIG. 62 with the implant shown in an expanded configuration.
Figure 69:
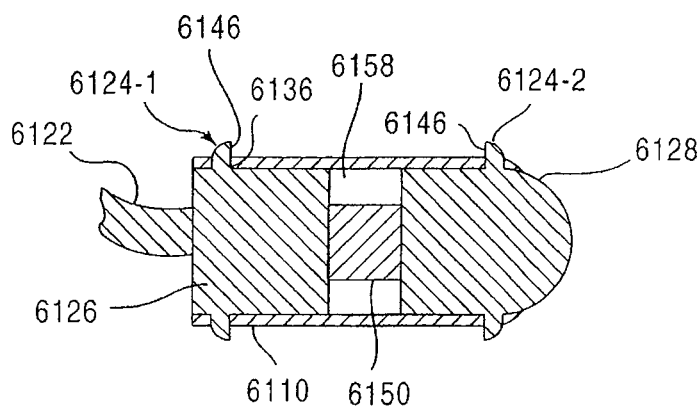
FIG. 69 is a cross-sectional view of the portion of the deployment tool and implant shown in FIG. 68.
Figure 70:
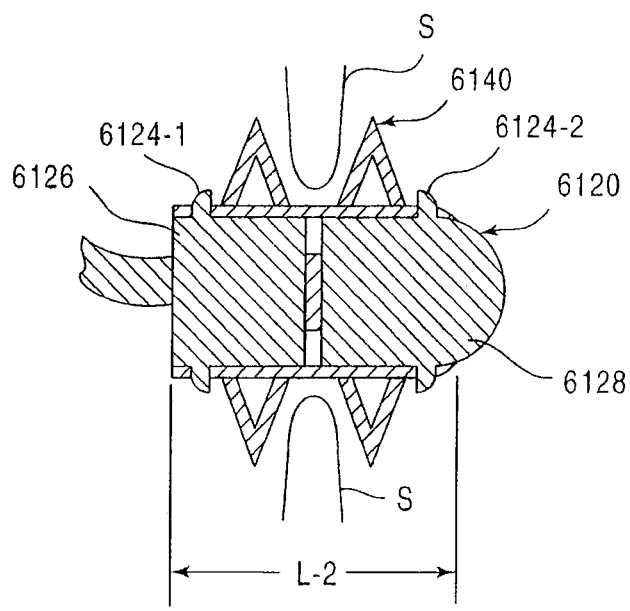
FIG. 70 is a cross-sectional view of the deployment tool and implant of FIG. 68 with the implant shown in a collapsed configuration positioned between adjacent spinous processes.

In use, the first body portion 6126 and the second body portion 6128 are collectively disposed within the lumen 6158 of the implant 6110, such that the engaging portions 6124 extend through the openings 6132 and transverse to an axis B defined by the implant 6110, as shown in FIGS. 68-70. In this position, the surface 6146 of the engaging portions 6124 is configured to contact the edge 6136 of the openings 6132. FIGS. 68 and 69 illustrate the first body portion 6126 and the second body portion 6128 disposed within the lumen of the implant 6110, when the implant is in a collapsed configuration. In this position, the first body portion 6126 is at a first distance from the second body portion 6128, the engaging portions 6124-1 are at a first distance from the engaging portions 6124-2, and the implant has a first length L-1.

When the implant is positioned between spinous processes S, the deployment tool 6120 can be actuated to move the implant 6110 to the expanded configuration, as shown in FIG. 70. When the deployment tool 6120 is actuated, the first body portion 6126 is moved closer to the second body portion 6128, and the engaging portions 6124-1 are moved closer to the engaging portions 6124-2. When this occurs, the surface 6146 on the engaging portions 6124 impart a force on the edge 6136 of the openings 6132, which axially compresses the implant 6110 until the implant 6110 has a second length L-2, as shown in FIG. 70.

Figure 76:
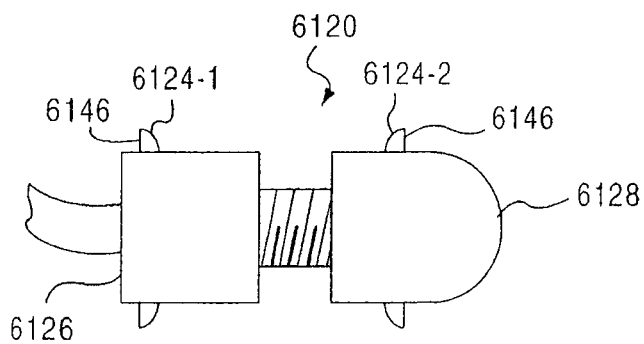
FIG. 76 is a side view of a deployment tool according to another embodiment of the invention.

To move the implant 6110 back to the collapsed configuration, the deployment tool 6120 can be reconfigured such that the surface 6146 of the engaging portions 6124 are positioned facing an opposite direction and configured to contact the edge 6138 of the implant 6110, as shown in FIG. 76. In some embodiments, the engaging portions 6124 can be, for example, removed and re-coupled to the elongate member 6122 (e.g., the first body portion 6126 and the second body portion 6128) such that the same engaging portions 6124 are simply repositioned. In other embodiments, a second deployment tool can be used having engaging portions positioned in the opposite direction. In either case, the deployment tool is inserted into the lumen 6158 of the implant 6110 as done previously, such that the engaging portions 6124 extend through the openings 6132 of the implant 6110 and the surface 6146 contacts the edge 6136 of the implant 6110. The deployment tool 6120 is then actuated in an opposite direction (e.g., turned in an opposite direction) such that the first body portion 6126 and the second body portion 6128 are threadedly moved further away from each other. In doing so, the engaging portions 6124-1 are moved further away from the engaging portions 6124-2, and the surface 6146 of the engaging portions 6124 impart a force on the edge 6138 (instead of edge of 6136) of openings 6132, which moves the implant 6110 back to the collapsed or straightened configuration. Thus, the implant described in all of the embodiments of the invention can be repeatedly moved between the collapsed and expanded configurations as necessary to insert, reposition or remove the implant as desired.

Figure 73:
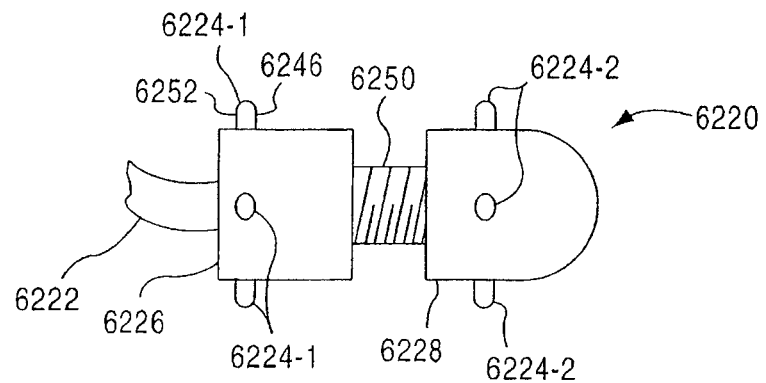
FIG. 73 is a side view of a deployment tool according to another embodiment of the invention.

FIG. 73 illustrates a deployment tool according to another embodiment of the invention. A deployment tool 6220 includes an elongate member 6222 having a first body portion 6226 coupled to a second body portion 6228 through a threaded coupling 6250. In this embodiment, the deployment tool 6220 includes two sets of four (8 total) engaging portions 6224 (only six engaging portions are shown in FIG. 73). A first set of engaging portions 6224-1 are coupled to the first body portion 6226, and a second set of engaging portions 6224-2 are coupled to the second body portion 6228. The engaging portions 6224 include a first surface 6246 and a second surface 6252. When the deployment tool 6220 is coupled to an implant, the first surface 6246 is configured to contact an edge of an opening defined on the implant (such as edge 6136 on implant 6110), and the second surface 6252 is configured to contact an opposite edge on the opening defined by the implant (such as edge 6138 on implant 6110).

Thus, in this embodiment, the deployment tool 6220 can be inserted into an implant and used to move the implant between a collapsed configuration and an expanded configuration without having to reposition the engaging portions 6224, or use a second deployment tool. To move the implant from a collapsed configuration to an expanded configuration, the deployment tool 6220 is actuated in a first direction. To move the implant back to the collapsed configuration, the deployment tool 6220 is actuated in an opposite direction (e.g., turned in an opposite direction). When the deployment tool 6220 is actuated to move the implant from the collapsed configuration to the expanded configuration, the surface 6246 of the engaging portions 6224 impart a force on an edge of an opening (e.g., edge 6136 on implant 6110), causing the implant to be axially compressed, as previously described. When the deployment tool 6220 is actuated to move the implant from the expanded configuration to the collapsed configuration, the surface 6252 of the engaging portions 6224 imparts a force on an opposite edge of the opening (e.g., edge 6138 on implant 6110), causing the implant to be substantially straightened as previously described.

Figure 74:
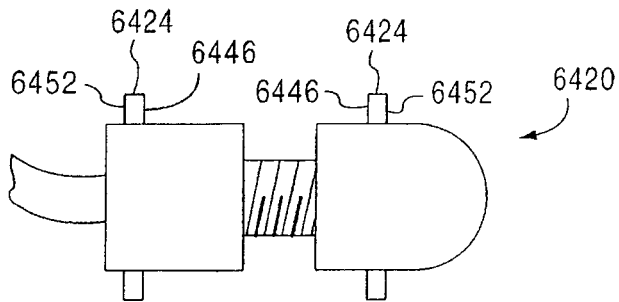
FIG. 74 is a side view of a deployment tool according to another embodiment of the invention.

FIG. 74 illustrates a deployment tool according to another embodiment of the invention. A deployment tool 6420 is similar to the deployment tool 6220 described above, except in this embodiment, there are only two sets of two engaging portions 6424 (4 total). The engaging portions 6424 are similar to the engaging portions 6224 except the engaging portions 6424 are substantially rectangular shaped. The engaging portions 6424 include a surface 6446 configured to contact an edge of an opening defined by an implant, and a surface 6452 configured to contact an opposite edge of the opening defined by the implant.

Figure 75:
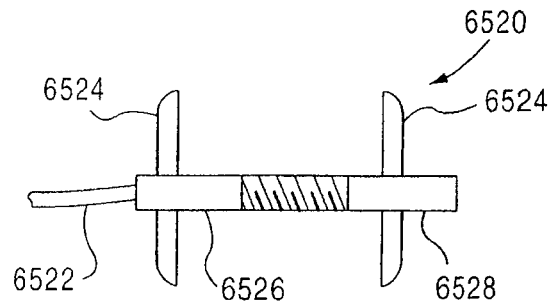
FIG. 75 is a side view of a deployment tool according to another embodiment of the invention.

FIG. 75 illustrates a deployment tool according to yet another embodiment of the invention. A deployment tool 6520 is similarly constructed and functions similarly to the previous embodiments. The deployment tool 6520 includes an elongate member 6522 that includes a first body portion 6526 and a second body portion 6528. In this embodiment, the first body portion 6526 and the second body portion 6528 are smaller than illustrated in the previous embodiments, and engaging portions 6524 are coupled to the first body portion 6526 and the second body portion 6528 that are more elongate than previously shown.

Figure 77:
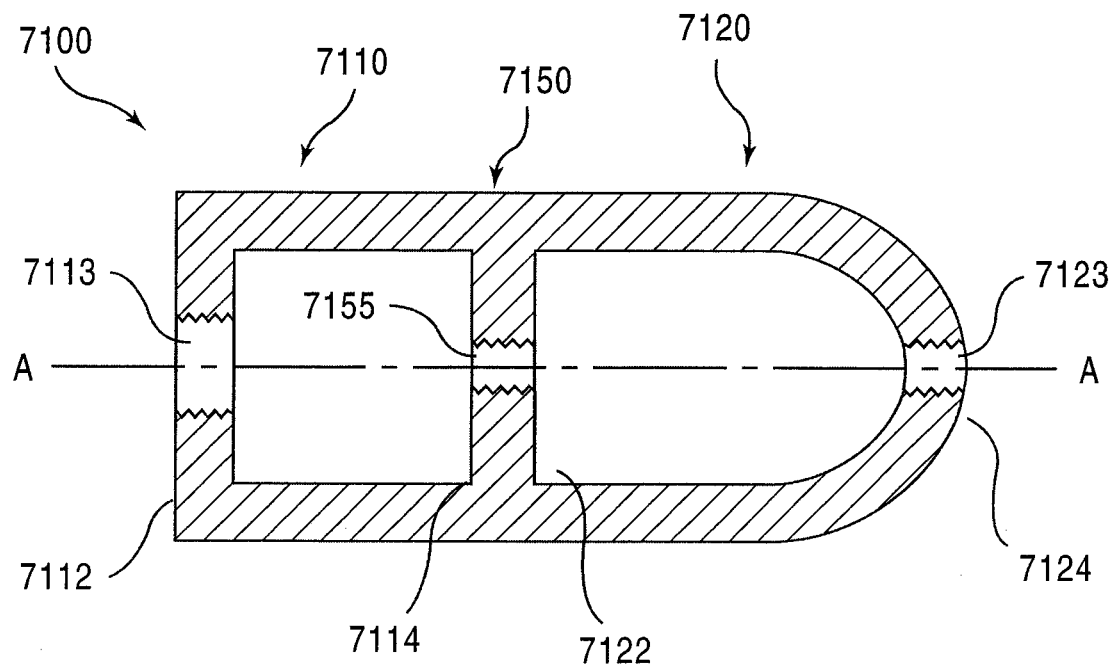
FIG. 77 is a side cross-sectional view of a medical device according to an embodiment of the invention in a first configuration.
Figure 78:
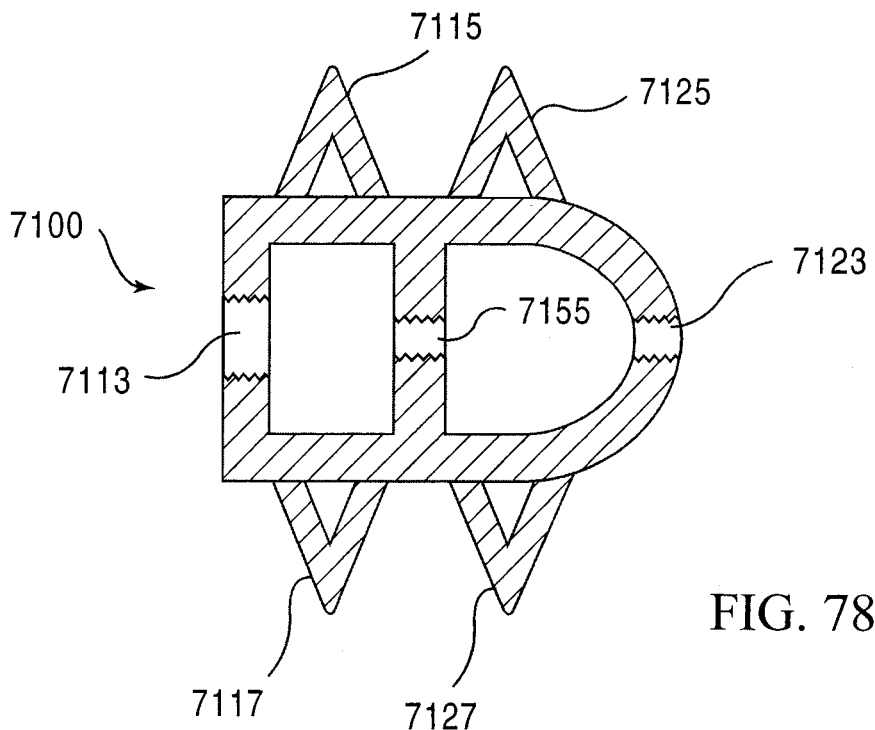
FIG. 78 is a side cross-sectional view of the medical device illustrated in FIG. 77 in a second configuration.

FIGS. 77 and 78 illustrate a spinal implant 7100 in a first configuration and second configuration, respectively. As shown in FIG. 77, the spinal implant 7100 is collapsed in a first configuration and can be inserted between adjacent spinous processes. The spinal implant 7100 has a first deformable portion 7110, a second deformable portion 7120 and a central, non-deformable portion 7150. The first deformable portion 7110 has a first end 7112 and a second end 7114. The second deformable portion 7120 has a first end 7122 and a second end 7124. The central portion 7150 is coupled between second end 7114 and first end 7122. In some embodiments, the spinal implant 7100 is monolithically formed.

The first deformable portion 7110, the second deformable portion 7120 and the central portion 7150 have a common longitudinal axis A along the length of spinal implant 7100. The central portion 7150 can have the same inner diameter as first deformable portion 7110 and the second deformable portion 7120. In some embodiments, the outer diameter of the central portion 7150 is smaller than the outer diameter of the first deformable portion 7110 and the second deformable portion 7120.

In use, spinal implant 7100 is inserted percutaneously between adjacent spinous processes. The first deformable portion 7110 is inserted first and is moved past the spinous processes until the central portion 7150 is positioned between the spinous processes. The outer diameter of the central portion 7150 can be slightly smaller than the space between the spinous processes to account for surrounding ligaments and tissue. In some embodiments, the central portion 7150 directly contacts the spinous processes between which it is positioned. In some embodiments, the central portion of spinal implant 7100 is a fixed size and is not compressible or expandable. Note the spinal implant 7100 and/or the first deformable portion 7110, second deformable portion 7120, and central portion 7150 can engage the spinous processes during all or just a portion of the range of motion of the spinous processes associated with the patient's movement.

The first deformable portion 7110 includes, for example, expanding members 7115, and 7117. Between the expanding members 7115, 7117, openings (not illustrated) are defined. As discussed above, the size and shape of the openings influence the manner in which the expanding members 7115, 7117 deform when an axial load is applied. The second deformable portion 7120 includes expanding members 7125 and 7127. Between the expanding members 7125, 7127, openings (not illustrated) are defined. As discussed above, the sizes and shapes of the openings influence the manner in which the expanding members 7125, 7127 deform when an axial load is applied.

When an axial load is applied to the spinal implant 7100, the spinal implant 7100 expands to a second configuration as illustrated in FIG. 109. In the second configuration, first end 7112 and second end 7114 of the first deformable portion 7110 move towards each other and expanding members 7115, 7117 project substantially laterally away from the longitudinal axis A. Likewise, first end 7122 and second end 7124 of the second deformable portion 7120 move towards one another and expanding members 7125, 7127 project laterally away from the longitudinal axis A. The expanding members 7115, 7117, 7125, 7127 in the second configuration form projections that extend to positions adjacent to the spinous processes between which the spinal implant 7100 is inserted. In the second configuration, the expanding members 7115, 7117, 7125, 7127 inhibit lateral movement of the spinal implant 7100, while the central portion 7150 prevents the adjacent spinous processes from moving together any closer than the distance defined by the diameter of the central portion 7150 during spinal extension.

The first end 7112 of the first deformable portion 7110 defines a threaded opening 7113. The central portion 7150 defines a second threaded opening 7155. The second end 7124 of the second deformable portion 7120 defines a third threaded opening 7123. The threaded openings 7113, 7155, 7123 receive portions of an actuator 7200 (see FIG. 79) to move the first deformable portion 7100 and the second deformable portion 7120 between their respective first configurations and second configurations as described in greater detail herein. In some embodiments, the first threaded opening 7113 has a greater diameter than the second threaded opening 7155 and the third threaded opening 7123 (see FIGS. 77-80). In some embodiments the second threaded opening 7155 and the third threaded opening 7123 have the same diameter (see FIGS. 77-80). In other embodiments, the first threaded opening 7113' and the second threaded opening 7155' have the same diameter (see FIGS. 81-84) and the third threaded opening 7123' has a smaller diameter than the first threaded opening and the second threaded opening. The threaded openings 7113, 7155, 7123, 7113', 7155', 7123' are coaxially aligned. In other embodiments, the threaded openings can be any combination of different or the same sizes.

Figure 79:
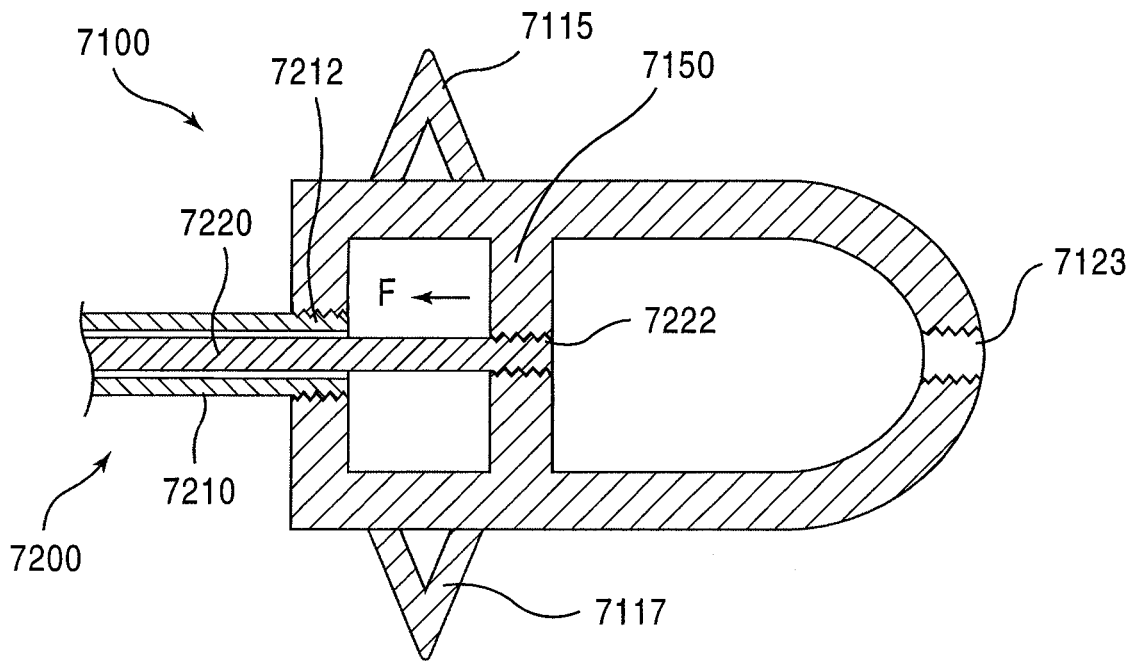
FIG. 79 is a cross-sectional side view of a medical device and an actuator according to an embodiment of the invention with a portion of the medical device deployed in a second configuration.

The spinal implant 7100 is deformed by a compressive force imparted substantially along the longitudinal axis A of the spinal implant 7100. As illustrated in FIG. 79, the compressive force is imparted to the first deformable portion 7110 by actuator 7200. The actuator includes a first portion 7210 and a second portion 7220 movably received within first portion 7210. In some embodiments, the second portion 7220 is slidably received within the first portion 7210. In other embodiments, the first portion 7210 and the second portion 7220 are threadedly coupled. Each of the first portion 7210 and the second portion 7220 is provided with external threads 7212 and 7222, respectively, to engage the threaded openings 7113, 7155, 7123, 7113', 7155', 7123'.

As illustrated in FIG. 79, the compressive force is imparted to the first deformable portion 7110, for example, by attaching the threaded portion 7212 to the first threaded opening 7113, attaching the threaded portion 7222 to the second threaded opening 7155 of the central portion 7150, and drawing the second portion 7220 along the longitudinal axis A while imparting an opposing force against the first end 7112 of the first deformable portion 7110. The opposing force results in a compressive force causing the spinal implant 7100 to expand as discussed above.

Figure 80:
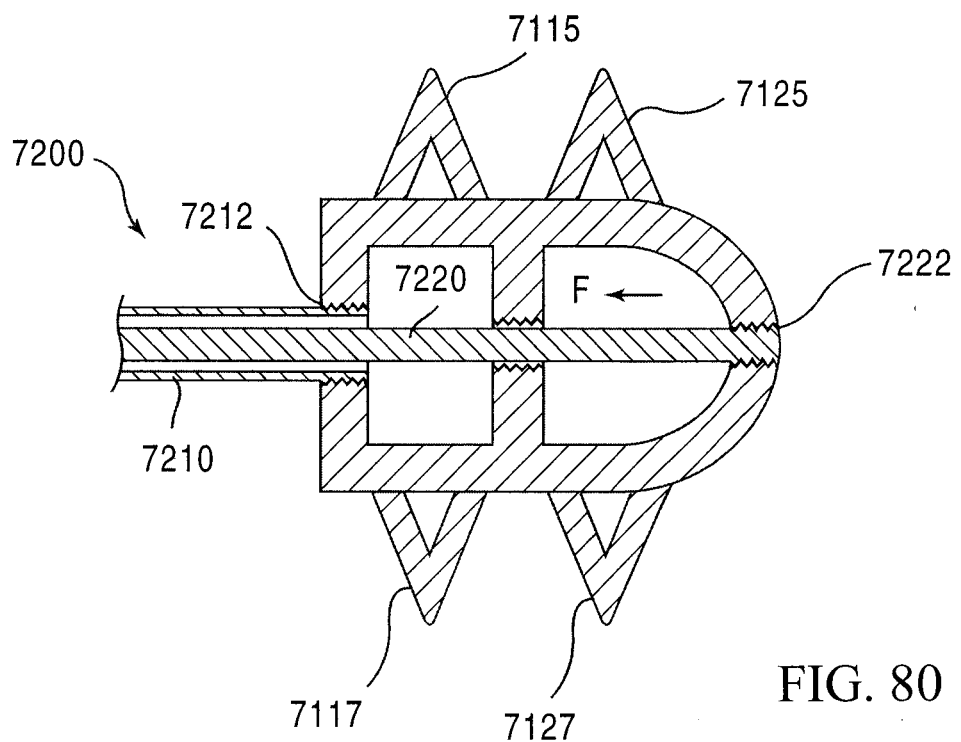
FIG. 80 is a side cross-sectional view of a medical device and an actuator according to an embodiment of the invention with the medical device fully deployed in the second configuration.
Figure 81:
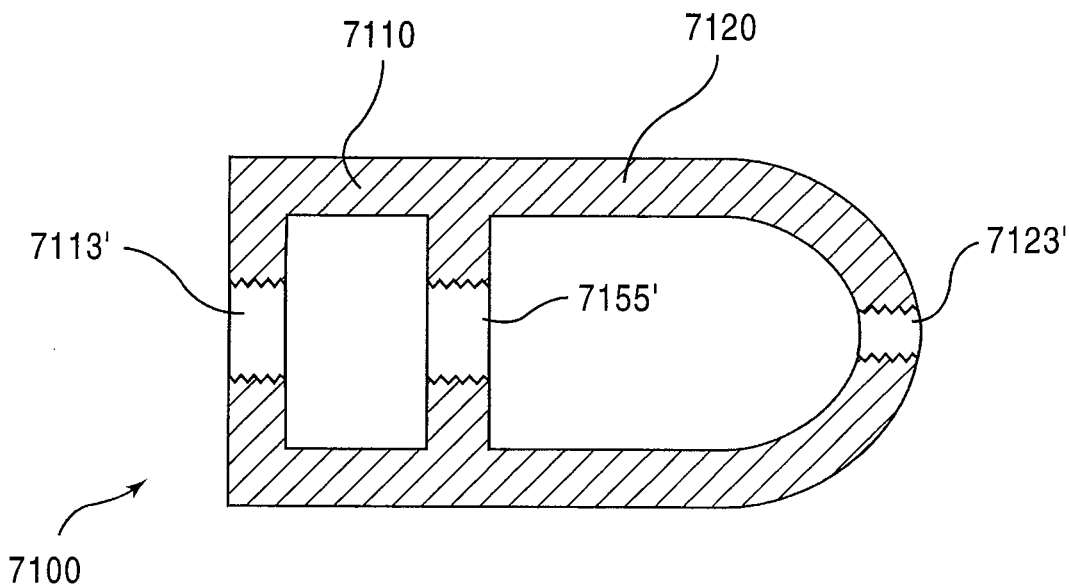
FIG. 81 is a side cross-sectional view of a medical device according to another embodiment of the invention in a first configuration.
Figure 82:
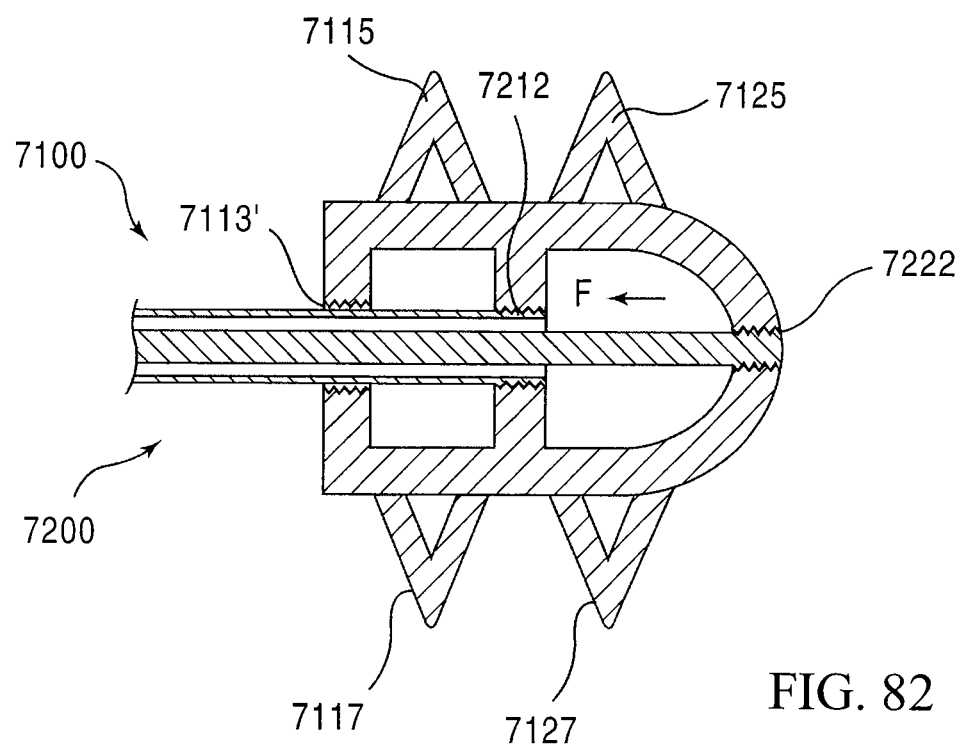
FIG. 82 is a side cross-sectional view of the medical device illustrated in FIG. 81 in a second configuration.

Once the first deformable portion 7110 is moved to its second configuration, the threaded portion 7222 is threaded through the second threaded opening 7155 and threadedly coupled to the third threaded opening 7123. A compressive force is imparted to the second deformable portion 7120 of the spinal implant 7100 by drawing the second portion 7220 of the actuator in the direction indicated by the arrow F while applying an opposing force using the first portion 7210 of the actuator against the spinal implant 7100. The opposing forces result in a compressive force causing the spinal implant to expand as illustrated in FIG. 80.

In some embodiments, the first deformable portion 7110 and the second deformable portion 7120 can be expanded simultaneously when the second portion 7220 of the actuator is coupled to the third threaded opening 7123 and the first portion 7210 is coupled to the first threaded opening 7113 and a compressive force is applied.

In embodiments in which the first threaded opening 7113' has the same diameter as the second threaded opening 7155' (best seen, for example, in FIGS. 81 and 82), the first threaded portion 7212 can be threadedly coupled to the second threaded opening 7155' and the second threaded portion 7222 can be threadedly coupled to the third threaded opening 7123'. A compressive force is then applied between the central portion 7150 and the second end 7124 of the second deformable portion 7120. Once the second deformable portion 7120 is in its second configuration, the first threaded portion 7212 can be threadedly coupled to the first threaded opening 7113' and the first deformable portion 7110 can be deformed into its second configuration.

Figure 83:
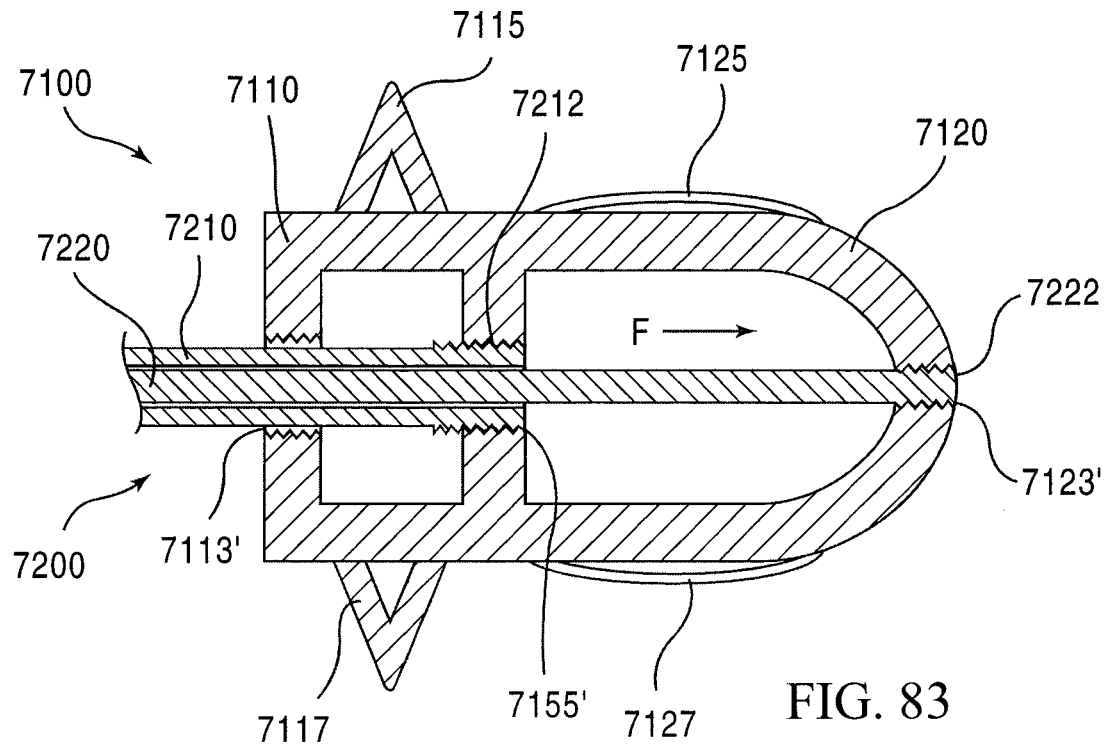
FIG. 83 is a side cross-sectional view of a medical device and an actuator according to an embodiment of the invention with a portion of the medical device moved back to its first configuration.
Figure 84:
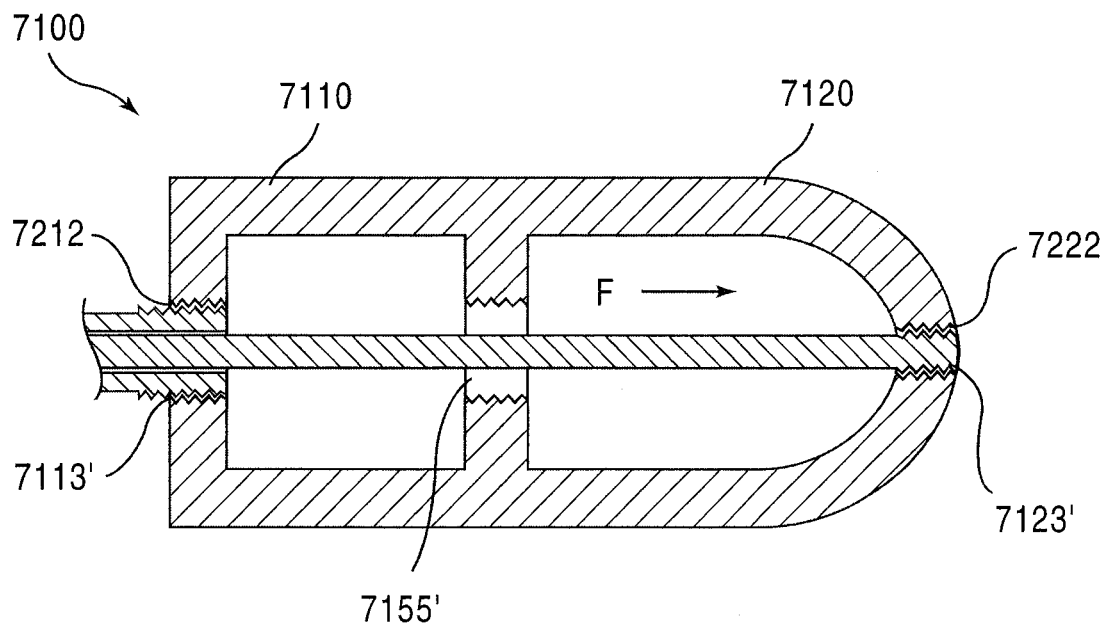
FIG. 84 is a side cross-sectional view of a medical device and an actuator according to an embodiment of the invention with the medical device moved back to its first configuration.

After each of the first deformable portion 7110 and the second deformable portion 7120 are moved to the second expanded configuration, they subsequently can each be moved back to the first collapsed configuration by applying a force in the opposite direction along longitudinal axis A as illustrated, for example, in FIGS. 83-84. In this example, as discussed above, the spinal implant 7100 illustrated in FIGS. 81-84 has a first threaded opening 7113' that has the same diameter as the second threaded opening 7155'.

With the first threaded portion 7212 coupled to the second threaded opening 7155' and the second threaded portion 7222 coupled to the third threaded opening 7123', the second portion 7220 of the actuator 7200 is moved in the direction indicated by arrow F to move the second deformable portion 7120 to its first collapsed configuration.

The first threaded portion 7212 is then coupled to the first threaded opening 7113' and the second portion 7220 of actuator 7200 is again moved in the direction of arrow F to move the first deformable portion 7110 to its first collapsed configuration. When the entire spinal implant 7100 has been completely collapsed, the spinal implant 7100 can be repositioned between the spinous processes, or removed from its position between the spinous processes and removed from the body in which it was previously inserted. In some embodiments, the first deformable portion 7110 and the second deformable portion 7120 are not completely collapsed, but are instead moved to a configuration between fully expanded and fully collapsed. In this manner the spinal implant 7100 may be repositioned or removed without being completely collapsed.

Figure 85:
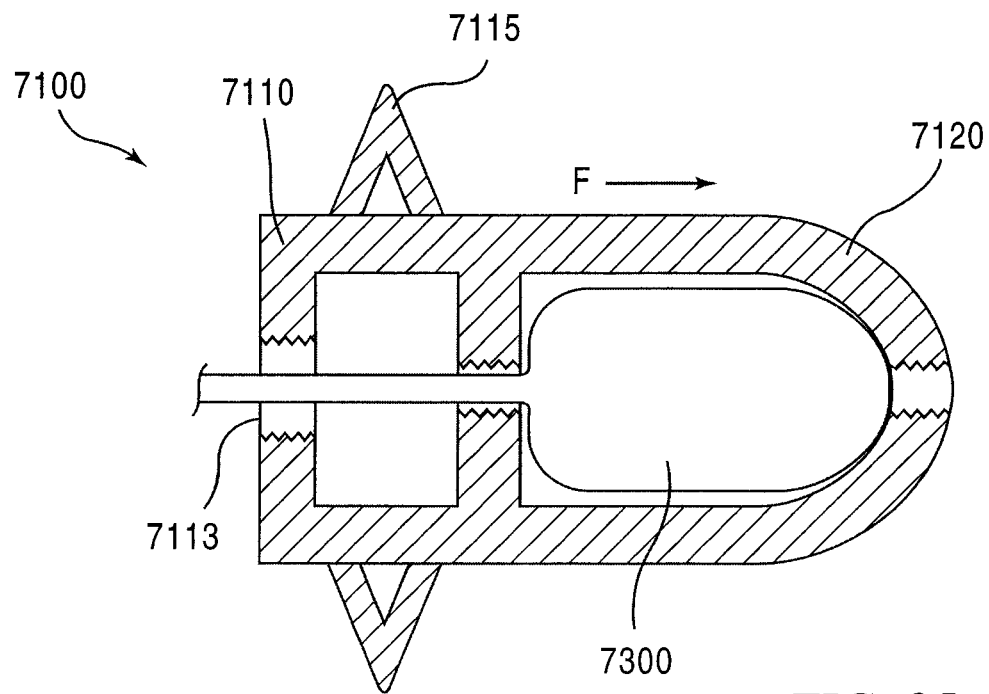
FIG. 85 is a side cross-sectional view of a medical device and an actuator according to an embodiment of the invention with a portion of the medical device moved back to its first configuration.

In some embodiments, the first deformable portion 7110 and the second deformable portion 7120 can be moved between the first and second configuration using a balloon as an actuator. As illustrated in FIG. 85, the second deformable portion 7120 is then moved from the second configuration to the first configuration by imparting a longitudinal force resulting from the inflation of a balloon 7300 with liquid and/or gas. As the balloon 7300 is inflated, it is forced against the central portion 7150 and the second end 7124 of the second deformable portion 7120. The force imparted by the balloon 7300 is generally in the direction indicated by the arrow F. In some embodiments, the balloon 7300 is a low-compliant balloon that is configured to expand to a predefined shape such that a force is imparted primarily in a substantially longitudinal direction indicated by arrow F.

Figure 86:
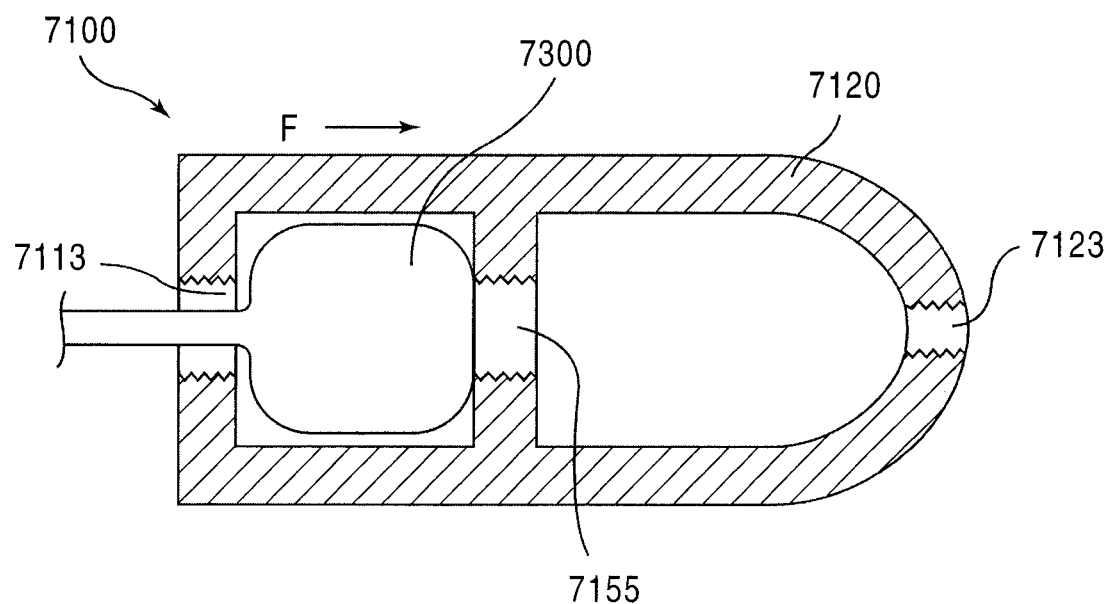
FIG. 86 is a side cross-sectional view of a medical device and an actuator according to an embodiment of the invention with the medical device moved back to its first configuration.

After the second deformable portion 7120 is moved substantially to its collapsed configuration, the balloon 7300 is deflated and moved into the first deformable portion 7110. The balloon 7300 is then inflated as illustrated in FIG. 86 to impart a force in the direction indicated by arrow F. In some embodiments, the same balloon 7300 is used to collapse both the first deformable portion 7110 and the second deformable portion 7120. In other embodiments, a different balloon is used for each portion 7110, 7120. Once the entire implant 7100 is moved to the first configuration, the balloon is deflated and removed. In some embodiments, the balloon 7300 remains in the spinal implant 7100, and the spinal implant 7100 and the balloon 7300 are removed simultaneously.

In some embodiments, the shaft on which the balloon is coupled has external threads (not illustrated) to mate with the first threaded opening 7113, 7113' and/or the second threaded opening 7155, 7155'. In other embodiments, neither the openings nor the shaft on which the balloon is coupled are threaded. In yet other embodiments, the balloon 7300 is inserted through the first portion 7210 of the actuator 7200. Alternatively, the actuator 7200 and the balloon 7300 can be used in conjunction with the spinal implant to expand and/or contract the first deformable portion 7110 and the second deformable portion 7120.

In other embodiments, there are no threaded openings defined in the spinal implant 7100. For example, the spinal implant can have multiple actuator-engaging portions that are not threaded, but are rather contact or bearing surfaces for various types of actuators. For example, an actuator (not illustrated) can be configured to grasp an outer surface of the spinal implant while simultaneously imparting a force against the distal portion of the spinal implant to move the implant to a collapsed configuration.

The spinal implant 7100 can be made from, for example, stainless steel, plastic, polyetheretherketone (PEEK), carbon fiber, ultra-high molecular weight (UHMW) polyethylene, etc. or some combination thereof. For example, the first deformable portion and the second deformable portion can be made from one material and the non-expanding central portion can be made from a different material. The material of such a non-expanding central portion can have a tensile strength similar to or higher than that of bone.

Figure 87:
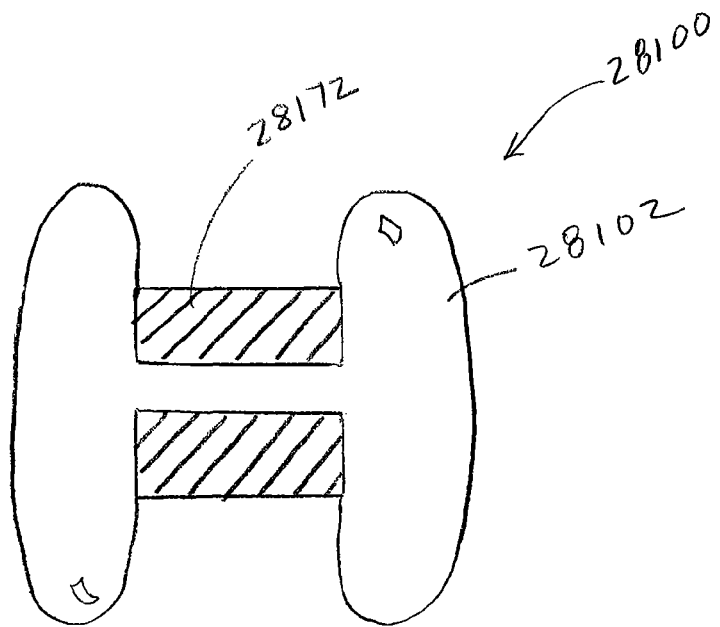
FIG. 87 is a side view partially in cross-section illustrating a medical device according to an embodiment of the invention shown in an expanded configuration.
Figure 88:
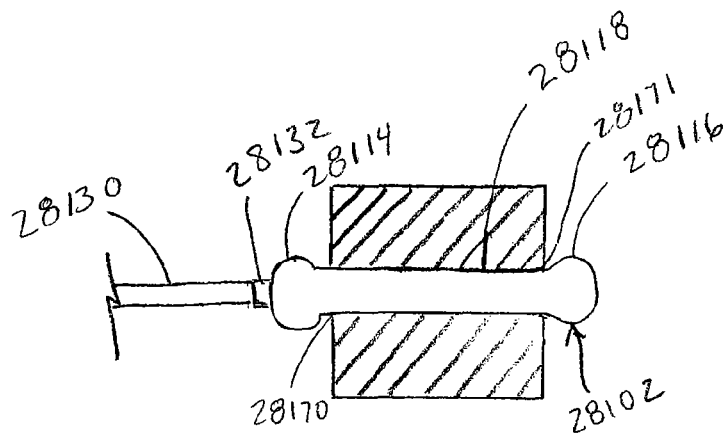
FIG. 88 is a side view partially in cross-section of the medical device of FIG. 87 shown in a collapsed configuration and a portion of an expansion device coupled to the medical device.
Figure 89:
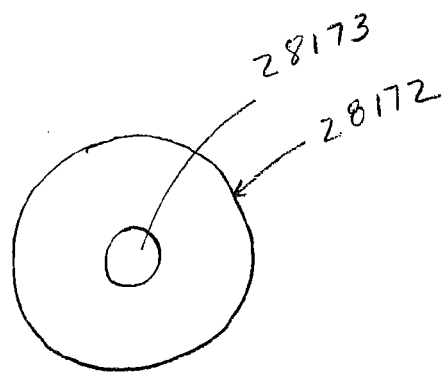
FIG. 89 is an end view of a support member of the medical device of FIG. 87.

FIGS. 87-89 illustrate another spinal implant according to an embodiment of the invention. An implant 28100 includes a support member 28172 and an expandable member 28102. The support member 28172 defines an internal lumen 28173 (see FIG. 89) through which the expandable member 28102 can be received, as shown in FIGS. 87 and 88. In some embodiments, the expandable member 28102 is secured to the support member 28172 with for example, RF bonding.

Figure 91:
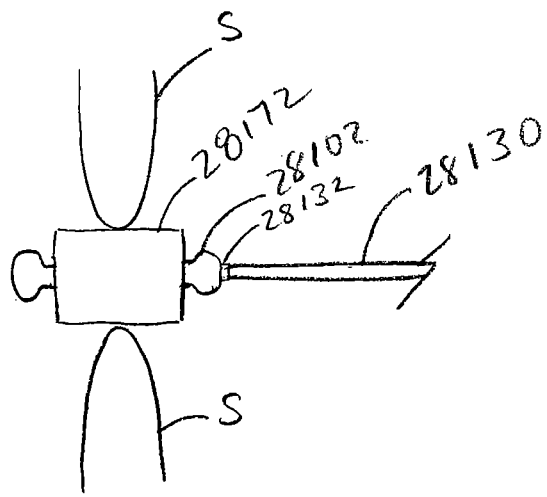
FIG. 91 is a posterior view of adjacent spinous processes and the medical device of FIG. 87 shown in a collapsed configuration disposed therebetween and coupled to a portion of an expansion device.

The expandable member 28102 can include a port or valve 28132 that can be releasably coupled to an expansion device 28130 (also referred to herein as an insertion tool or a deployment tool). Only a portion of the expansion device 28130 is shown in FIGS. 88 and 91. The expansion device can be configured, for example, similar to the expansion device 1500 described above. The expansion device 28130 can be coupled to a source of an expansion medium (not shown), or can contain the medium within a reservoir incorporated with the expansion device 28130. For example, the expansion device 28130 can include a syringe configured to be releasably coupled to the valve 28132. In some embodiments, the expansion device 28130 can include a tubular member releasably coupled to the valve 28132 and coupled to a source of the expansion medium. The expansion device 28130 can be used to insert the implant 28100 into a desired location within a patient's body. The expansion device 28130 can also be used to inject and/or remove a medium (e.g., air, fluid, gel, silicone) into and from the expandable member 28102 to move the expandable member 28102 between an expanded configuration as shown in FIG. 87 and a collapsed configuration as shown in FIG. 88.

The valve 28132 can be any valve suitable for sealingly connecting the expandable member 28102 to an expansion device (e.g., expansion device 28130). For example, in some embodiments, the valve 28132 can be, for example, a poppet valve, a pinch valve or a two-way check valve. In other embodiments, the valve includes a coupling portion (not shown) configured to allow the expansion device 28130 to be repeatably coupled to and removed from the valve 28132. For example, in some embodiments, the valve 28132 can include a threaded portion configured to matingly couple the expansion device 28130 and the valve 28132.

The expandable member 28102 has a proximal end portion 28114, a distal end portion 28116 and a central portion 28118. The proximal end portion 28114 is configured to be disposed outside a proximal end 28170 of the lumen 28173 of the support member 28172 and the distal end portion 28116 is configured to be disposed outside a distal end 28171 of the lumen 28173 of the support member 28172. The central portion 28118 is configured to be substantially or partially disposed within the lumen 28173 of the support member 28172.

When expanded as shown in FIG. 87, the proximal end portion 28114 and the distal end portion 28116 each expand such that they have a size (e.g., outer perimeter or diameter) that is greater than a size (e.g., outer perimeter or diameter) of the support member 28172, as shown in FIG. 87. Thus, the proximal end portion 28114 and the distal end portion 28116 can be used to the support member 28172 and prevent or reduce lateral movement of the support member 28172 when the medical device 28100 is disposed between adjacent spinous processes and the expandable member 29102 is in the expanded configuration.

The expandable member 28102 can have a variety of different shapes and sizes when in the expanded configuration. For example, the expandable member 28102 can be expanded such that the proximal end portion 28114 expands to a different shape and/or size than the distal end portion 28116. In some embodiments, the proximal end portion 28114 and the distal end portion 28116 each expand substantially equally and substantially uniformly or symmetrically as shown in FIG. 87. In other embodiments, the proximal end portion 28114 and the distal end portion 28116 of the expandable member 28102 can expand asymmetrically and/or unequally, in shape and/or in time.

As discussed above with respect to other embodiments of spinal implants, the spinal implant 28100 can be inserted percutaneously between adjacent spinous processes, for example, through a cannula. The spinal implant 28100 can be placed in a space between adjacent spinous processes with the expandable member 28102 disposed within the lumen 28173 of the support member 28172 (e.g., with the expandable member 28102 coupled to the support member 28172), or the support member 28172 and the expandable member 28102 can be inserted into position in two steps (e.g., separately). In either case, the expandable member 28102 is in the collapsed configuration when inserted into a patient's body.

Figure 90:
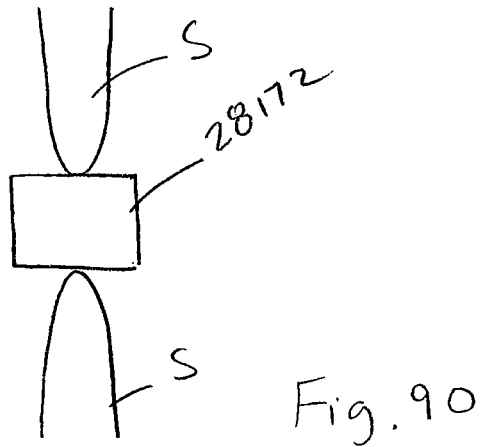
FIG. 90 is a posterior view of adjacent spinous processes and a support member of the medical device of FIG. 87 disposed therebetween.

In one example, the support member 28172 is inserted first and placed in the space between adjacent spinous processes S, as shown in FIG. 90. The expandable member 28102 is then inserted through the lumen 28173 of the support member 28172 while in a collapsed configuration such that the distal end portion 28116 of the expandable member 28102 is disposed outside the distal end 28171 of the lumen 28173 of the support member 28172 and the proximal end portion 28114 is disposed outside the proximal end 28170 of the lumen 28173 of the support member 28172 as shown in FIG. 88. The support member 28172 and the expandable member 28102 can each be sized to account for ligaments and tissue surrounding the spinous processes S during insertion. For purposes of clarity, such surrounding ligaments and tissue are not illustrated.

In an alternative example, the expandable member 28102 is first inserted through the lumen 28173 of the support member 28172 while in the collapsed configuration such that the distal end portion 28116 of the expandable member 28102 is disposed outside the distal end 28171 of the lumen 28173 of the support member 28172, and the proximal end portion 28114 is disposed outside the proximal end 28170 of the lumen 28173 of the support member 28172. As described above, the expandable member 28102 can be secured to the support member 28172 with, for example, RF bonding. The support member 28172 and expandable member 28102 can then collectively be placed in the space between adjacent spinous processes S.

Figure 92:
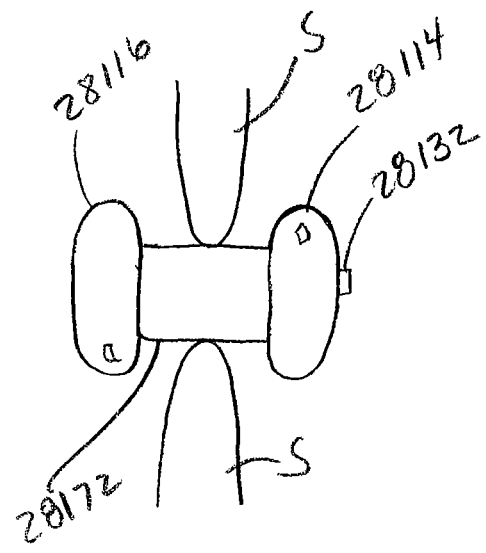
FIG. 92 is a posterior view of adjacent spinous processes and the medical device of FIG. 91 shown in an expanded configuration disposed therebetween.

Once in position, the expandable member 28102 is expanded into the expanded configuration by conveying a medium (not shown), such as for example, silicone, to an inner volume of the expandable member 28102 via the expansion device 28130. This will move the expandable member 28102 to the expanded configuration as shown in FIG. 92.

As described above with reference to implant 4100, the medium can be configured to retain its properties while disposed within the inner volume of the expandable member 28102. In this manner, the spinal implant 28100 can be repeatably transitioned from the expanded configuration to the collapsed configuration by injecting and/or removing the medium from the inner volume of the expandable member 28102. Thus, as described above for implant 4100, the spinal implant 28100 can be repositioned as needed. The spinal implant 28100 can be removed from the patient, for example, by first collapsing the expandable member 28102 and then removing collectively the support member 28172 and the expandable member 28102 from the patient's body (e.g., in an embodiment with the expandable member 28102 secured to the support member 28172). Alternatively, the expandable member 28102 can be collapsed and then removed from the patient prior to removal of the support member 28172.

In some embodiments, the medium used to expand the expandable member can be a biocompatible liquid having constant or nearly constant properties. Such liquids can include, for example, saline solution. In other embodiments, the medium can be a biocompatible liquid configured to have material properties that change over time while still retaining fluidic properties sufficient to allow removal of the fluid. For example, the viscosity of a fluid can be increased by adding a curing agent or the like. In this manner, the medium can provide both the requisite structural support while retaining the ability to be removed from the inner area of the expandable member 28102 via the valve 28132. In yet other embodiments, the medium can be a biocompatible gas or gel. In some embodiments, the medium can be a fluid that can change its viscosity based on a change of temperature. For example, such a medium can be injected into the expandable member at a first temperature and having a first viscosity. When the temperature of the medium is raised, for example, to the body temperature of a patient, the medium can change to a second viscosity that is higher than the first viscosity. When the temperature of the medium is reduced, the viscosity can be reduced to a lower viscosity.

Figure 93:
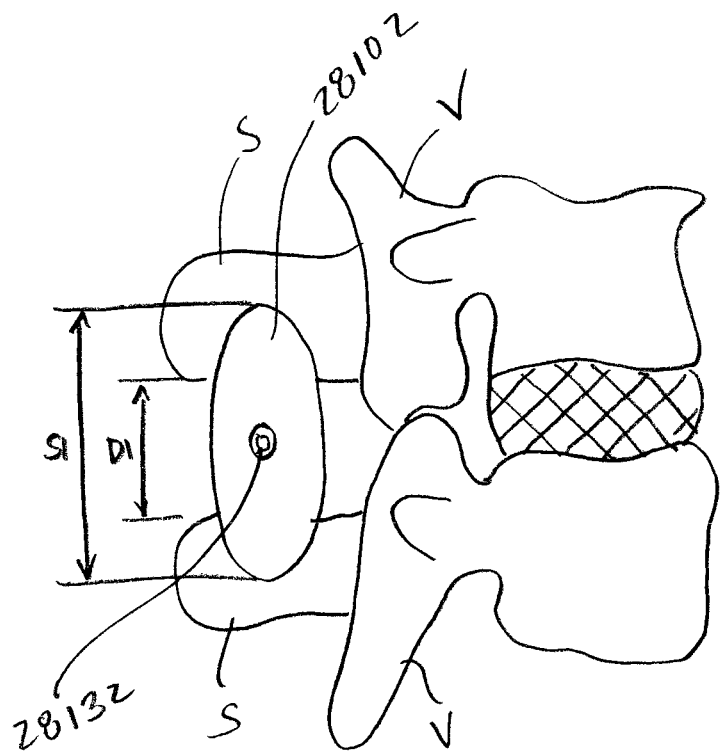
FIG. 93 is a lateral view of adjacent vertebrae with the medical device of FIG. 87 shown in an expanded configuration disposed between adjacent spinous processes

When expanded, the proximal end portion 28114 and the distal end portion 28116 each have a size S1 (shown in FIG. 93) that is greater than the vertical distance D1 (shown in FIG. 93) between the adjacent spinous processes S, when the adjacent spinous processes S are in a flexion position. In some embodiments, the distance D1 between the spinous processes S is, for example, between 8 mm and 16 mm. The distance D1 can be different among patients depending on the particular anatomy of the patients. In this manner, the proximal end portion 28114 and the distal end portion 28116 are disposed on opposite sides (laterally) of the spinous processes S and by either direct contact or through surrounding tissue, can limit the lateral movement of the spinal implant 28100 along a longitudinal axis of the support member 28172.

Also when positioned between the adjacent spinous processes S, the support member 28172 can engage the spinous processes S for at least a portion of the range of motion of the spinous processes S to limit extension/compression of the spinous processes S. In some embodiments, the engagement of the spinous processes S by the support member 28172 is not continuous, but occurs upon spinal extension. As discussed above, the adjacent spinous processes S can be distracted by a trocar and/or any other device suitable for distraction prior to insertion of the implant 28100.

The expandable member 28102 can be made from any number of biocompatible materials, such as, for example, PET, Nylons, cross-linked Polyethylene, Polyurethanes, PVC, titanium and/or polyetheretherketone (PEEK) material. In some embodiments, the chosen material can be substantially inelastic, thereby forming a low-compliant expandable member 28102. In other embodiments, the chosen material can have a higher elasticity, thereby forming a high-compliant expandable member 28102. In yet other embodiments, the expandable member 28102 can be made from a combination of materials such that one portion of the expandable member 28102, such as the central portion 28118, can be low-compliant while other portions of the expandable member 28102, such as the proximal end portion 28114 and/or distal end portion 28116 are more highly compliant. In yet other embodiments, a portion of the expandable member 28102 can include a rigid, inflexible material to provide structural stiffness. For example, the central portion 28118 can be constructed of a composite material that includes a rigid, inflexible material to facilitate distraction of the adjacent spinous processes.

In some embodiments, the expandable member 28102 includes a radiopaque material, such as bismuth, to facilitate tracking the position of the spinal implant 4100 during insertion and/or repositioning. In other embodiments, the medium used to expand the expandable member 28102 includes a radiopaque tracer to facilitate tracking the position of the spinal implant 28100.

Figure 95:
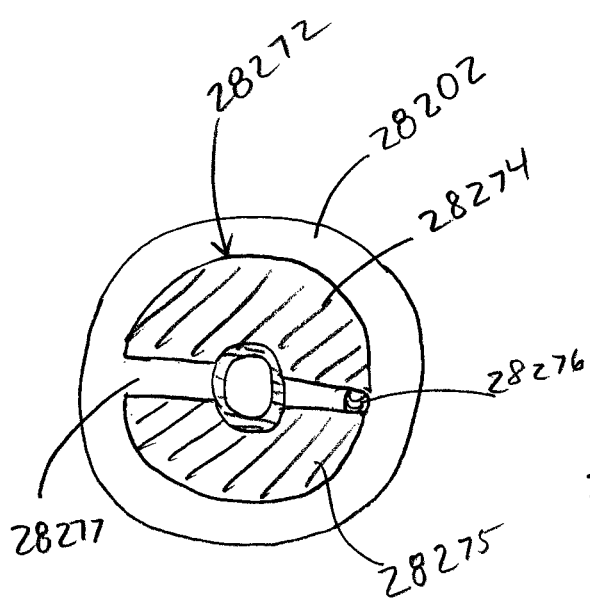
FIG. 95 is a cross-sectional end view of the medical device of FIG. 94 shown in an expanded configuration.
Figure 94:
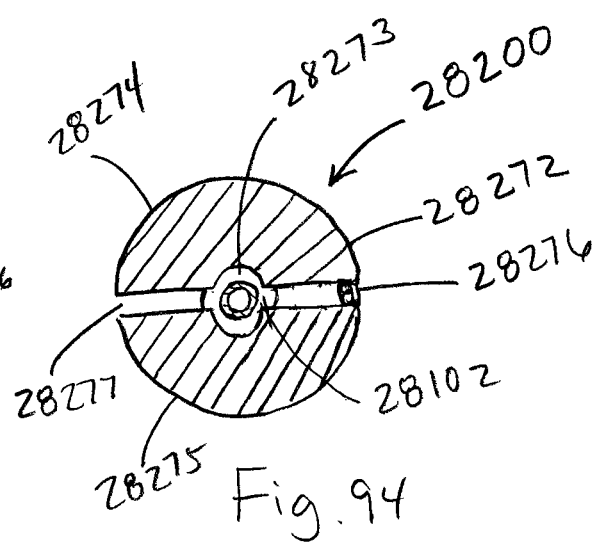
FIG. 94 is a cross-sectional end view of a medical device according to another embodiment of the invention shown in a collapsed configuration.

FIGS. 94 and 95 illustrate a spinal implant 28200 that is similar to the implant 28100. In this embodiment, the implant 28200 includes a support member 28272 that includes a first portion 28274 that is coupled to a second portion 2875. The first portion 28274 can be coupled to the second portion 28275 with, for example, a hinged coupling 28276 to allow the first portion 28274 and the second portion 28275 to move relative to each other. In some embodiments, a gap 28277 is defined between the first portion 28274 and the second portion 28275 as shown in FIGS. 94 and 95.

The first portion 28274 and the second portion 28275 also define an interior region or lumen 28273 through which an expandable member 28202 can be disposed in a similar manner as described above for implant 28100. The expandable member 28202 can be configured substantially the same, and can function in substantially the same manner, as the expandable member 28102, and thus, will not be described in detail with reference to this embodiment.

As stated above, the two-part construction of the support member 28272 allows the first portion 28274 of the support member 28272 and the second portion 28275 of the support member 28272 to move relative to each other. For example, the first portion 28274 and the second portion 282785 are in a first position when the expandable member 28202 is in a collapsed configuration as shown in FIG. 94. When the expandable member 28202 is expanded to an expanded configuration as shown in FIG. 95, the first portion 28274 and the second portion 28275 are in a second position relative to each other (i.e., moved further apart from each other). Thus, when the implant 28200 is disposed between adjacent spinous processes, the support member 28272 in this embodiment can distract the adjacent spinous processes as the expandable member 28202 expands to its expanded configuration.

Figure 96:
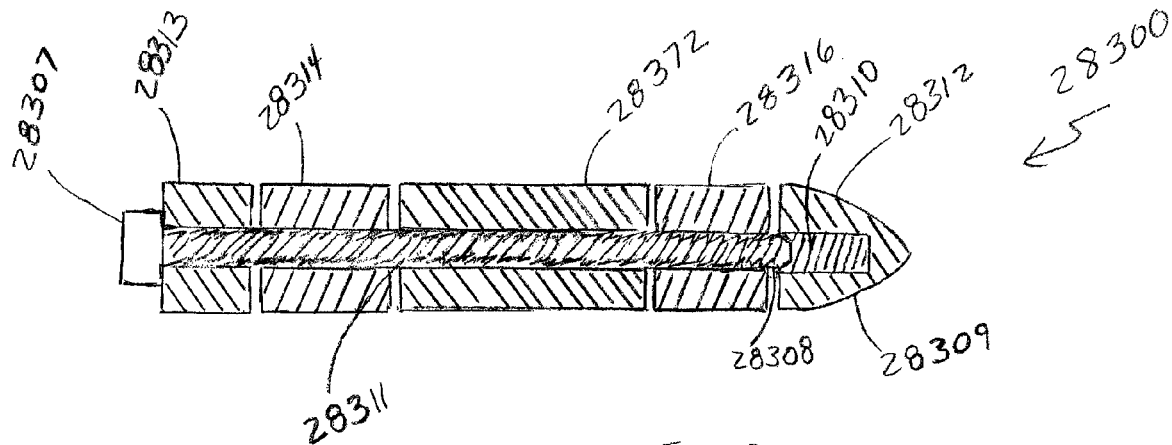
FIG. 96 is a side partial cross-sectional view of a medical device according to another embodiment of the invention shown in a collapsed configuration.
Figure 99:
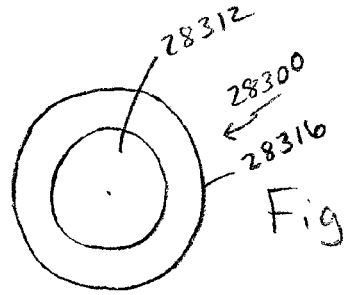
FIG. 99 is a distal end view of the medical device of FIG. 98 shown in an expanded configuration.
Figure 97:
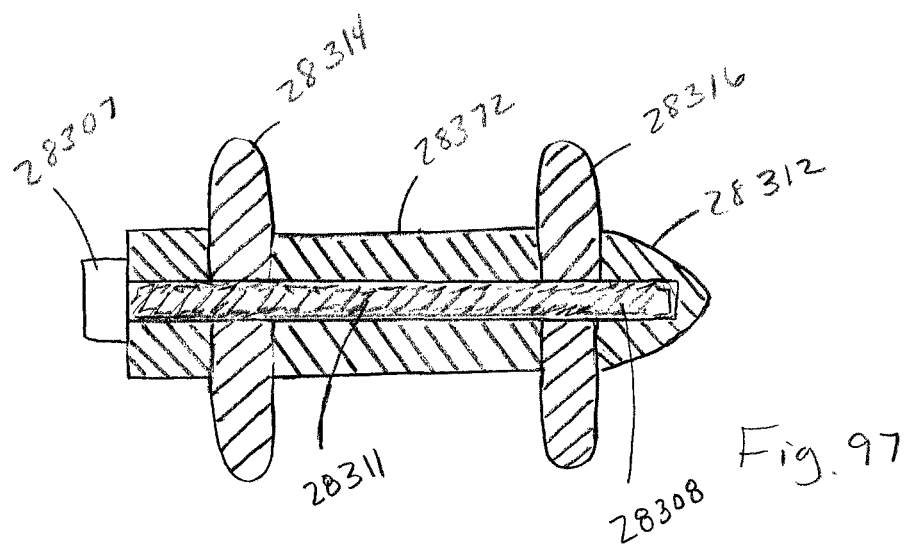
FIG. 97 is a side partial cross-sectional view of the medical device of FIG. 96 shown in an expanded configuration.

FIGS. 96-100 illustrate another embodiment of a spinal implant. An implant 28300 can be moved between a collapsed configuration, as shown in FIG. 96, and an expanded configuration, as shown in FIG. 97. The implant 28300 includes a first expandable member 28314, a second expandable member 28316, a distal hub member 28312 and a support member 28372. The implant 28300 also includes a base member 28313 and an elongate member 28311.

Figure 101:
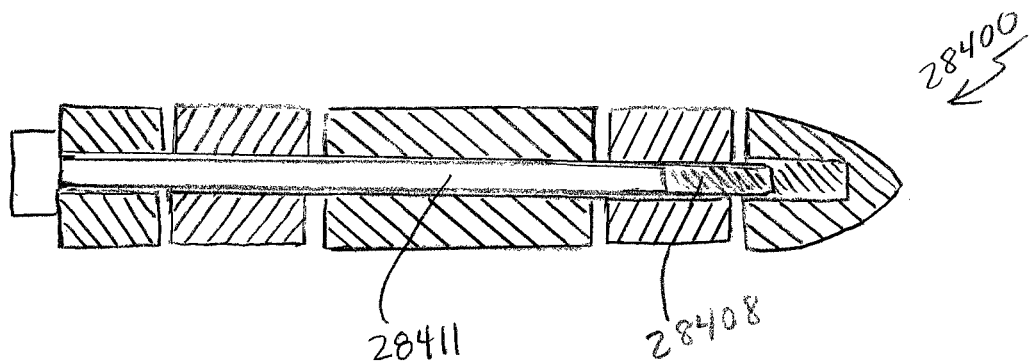
FIG. 101 is a side partial cross-sectional view of a medical device according to another embodiment of the invention shown in a collapsed configuration.

The first expandable member 28314, the second expandable member 28316, the support member 28372 and the base 28313 each define a lumen (collectively labeled 28305 in FIGS. 96 and 97) through which the elongate member 28311 can be received. Thus, the first expandable member 28314, the second expandable member 28316, the support member 28372 and the base 28313 are movably coupled to the elongate member 28311. The distal hub member 28312 includes a lumen 28310 that terminates within the distal hub member 28312. The lumen 28310 includes threaded internal walls configured to threadedly mate or engage a threaded portion 28308 on the elongate member 28311. In some embodiments, the first expandable member 28314, the second expandable member 28316, the support member 28372 and/or the base 28313 can be threadedly coupled to the elongate member 28311. The elongate member 28311 shown in FIGS. 96 and 97 include threads along substantially the entire length of the elongate member. It should be understood, however, that the elongate member 28311 can include only a portion with threads. For example, FIG. 101 illustrates an alternative embodiment of an elongate member 28411 having a threaded portion 28408 only on a distal end portion of the elongate member 28411.

Figure 98:
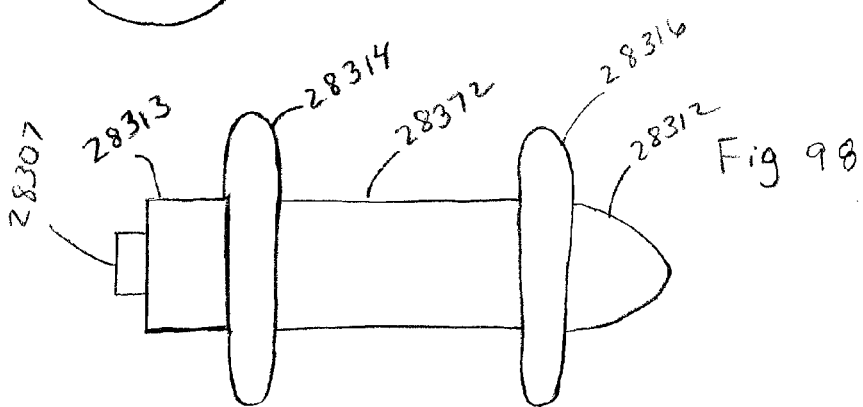
FIG. 98 is a side view of the medical device of FIG. 96 shown in an expanded configuration.

The threaded portion 28308 on the elongate member 28311 is configured to engage the threaded interior walls of the lumen 28310 of the distal hub member 28312 such that when the elongate member 28311 is rotated in a first direction, the distal hub member 28312 is drawn proximally along the elongate member 28311. For example, the elongate member 28311 can be rotated using a tool such as a medical screw driver (not shown) configured to engage a proximal end portion 28307 of the elongate member 28311. The medical screw driver can be incorporated with an insertion tool (described above) or can be a separate tool from the insertion tool. In some embodiments, it may be desirable to use a medical screw driver with a ratchet mechanism. In such a case, the rotation of the elongate member can be limited or controlled with each increment of the ratchet. As the elongate member 28311 is rotated, the distal hub member 28312 is moved (drawn proximally) from a first position (as shown in FIG. 96) along the threaded portion 28308 of the elongate member 28311 to a second position (shown in FIGS. 98 and 99). As the distal hub member 28312 is moved to the second position, it exerts a compressive force on the first expandable member 28316 and the second expandable member 28314 moving them to an expanded configuration as shown in FIGS. 97 and 98. The implant 28300 can be moved back to the collapsed configuration by rotating the elongate member 28311 in an opposite direction such that the distal hub member 28312 is moved distally from the second position back to the first position. As the distal hub member 28312 is moved back to the first position, the first expandable member 28316 and the second expandable member 28314 are free (e.g., the axial force is no longer exerted on them) to move back to their collapsed configuration.

The support member 28372, the distal hub member 28312, and the base 28313 can each be formed with a rigid material, for example, a titanium or PEEK material. The first expandable member 28316 and the second expandable member 28314 can each be formed with a flexible and/or elastic material, for example, a rubber or polymer material that allows for elastic deformation through compression. The material of the first expandable member 28316 and the second expandable member 28314 allows them to be moved back to the collapsed configuration (as shown in FIG. 96) after being deformed into the expanded configuration. In some embodiments, when moved back to the collapsed configuration, the first expandable member 28316 and the second expandable member 28314 return to their original biased shapes. In some embodiments, the first expandable member 28316 and the second expandable member 28314 can be moved back to their original shapes. Thus, the implant 28300 can be repeatedly moved between a collapsed configuration and an expanded configuration as needed, to reposition or remove the implant 28300 within or from a patient's body.

When in the expanded configuration, the first expandable member 28316 and the second expandable member 28314 have a size (e.g., outer perimeter or diameter) that is greater than a size (e.g., an outer perimeter or diameter) of the support member 28372. Thus, the first expandable member 28316 and the second expandable member 28314 can be used to retain the implant 28300 in a desired position within a patient's body. The first expandable member 28316 and the second expandable member 28314 can be a variety of different shapes and sizes depending on the particular application of the implant 28300.

For example, as with other embodiments described herein, the implant 28300 can be inserted into a patient's body while in a collapsed configuration such that the support member 28372 is positioned in a space between adjacent spinous processes. The first expandable member 28316 and the second expandable member 28314 can then be moved (e.g., elastically deformed) to the expanded configuration. The first expandable member 28316 and the second expandable member 28314 can be sized such that when in the expanded configuration, the first expandable member 28316 and the second expandable member 28314 prevent or limit lateral movement of the implant 28300 when disposed between the adjacent spinous processes.

The first expandable member 28314 and the second expandable member 28316 can be a variety of shapes and sizes and can be configured to expand in different manners. for example, the first expandable member 28314 and the second expandable member 28316 in FIGS. 96-99 are substantially symmetric and expand substantially symmetrically.

Figure 100:
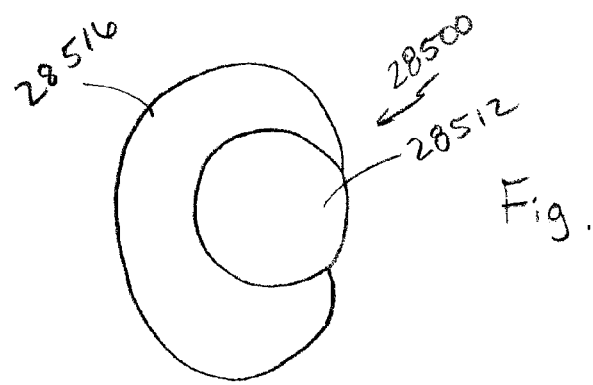
FIG. 100 is a distal end view of another embodiment of a medical device shown in an expanded configuration.

In an alternative embodiment, shown in the distal end view of FIG. 100, an implant 28500 includes a distal hub member 28512 and an expandable member 28516. In this embodiment, the expandable member 28516 is configured to expand asymmetrically with respect to a centerline or longitudinal axis defined by the implant 28500.

In some embodiments, an implant can be configured with an elongate member that is actuated through axial motion, rather than rotational motion. For example, an elongate member can be configured to be releasably coupled to the distal hub member in a similar manner as shown and described with reference to implant 6610. An expansion tool (e.g., tool 1500 or 7500) can be used to exert an axial force on the distal hub member by pulling the elongate member proximally (exerting a proximal force on the elongate member). This will in turn compress (elastically deform) the first expandable member and the second expandable member and move them to their expanded configuration. The tool can be actuated in an opposite direction (applying an axial force on the elongate member in a distal direction) to move the first expandable member and the second expandable member back to the collapsed configuration.

Figure 102:
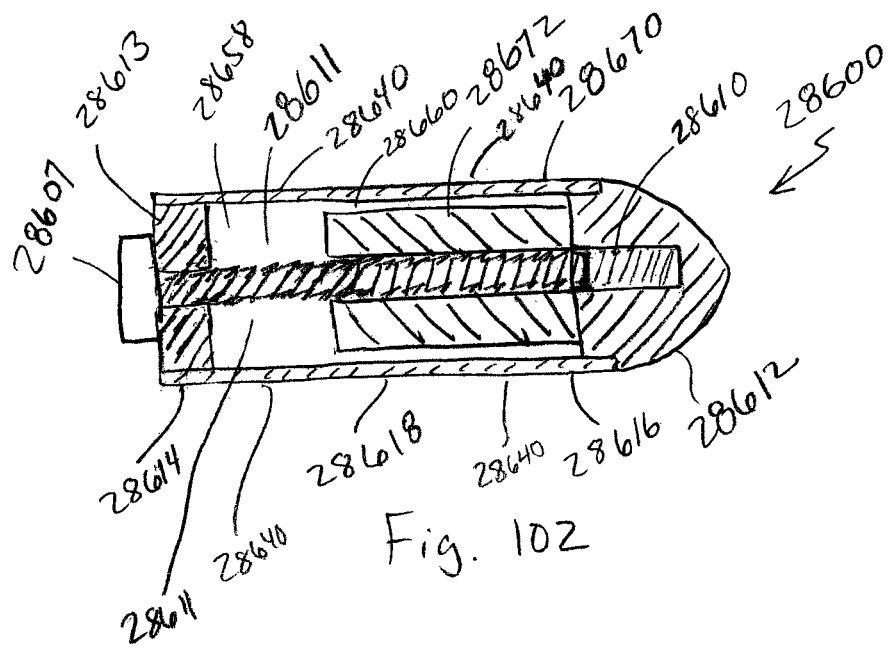
FIG. 102 is a side partial cross-sectional view of a medical device according to another embodiment of the invention shown in a collapsed configuration.
Figure 103:
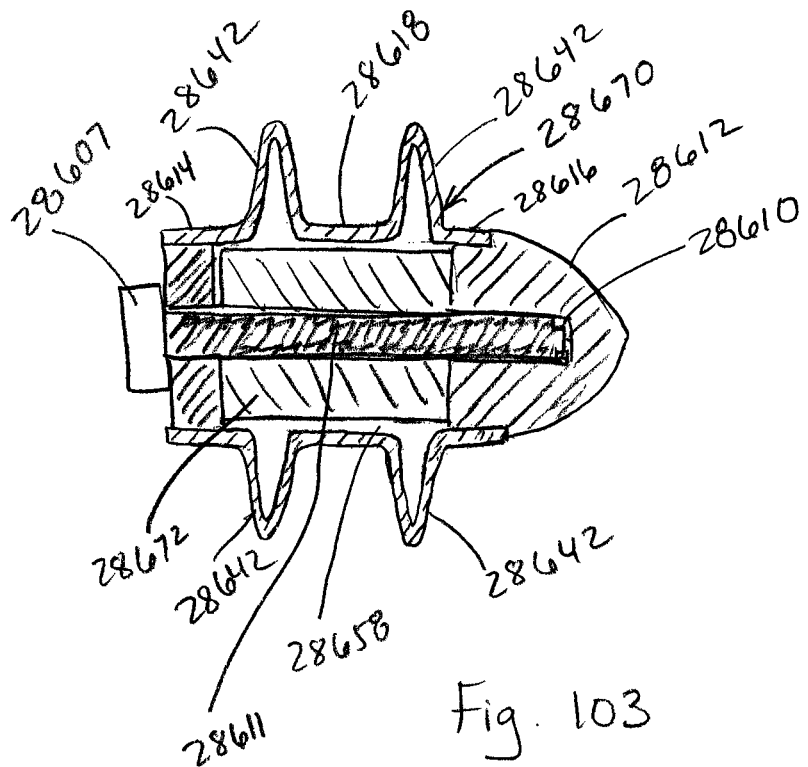
FIG. 103 is a side partial cross-sectional view of a medical device of FIG. 102 shown in an expanded configuration.

FIGS. 102 and 103 illustrate an implant 28600 according to another embodiment of the invention. The implant 28600 can be moved between a collapsed configuration, as shown in FIG. 102, and an expanded configuration, as shown in FIG. 103. The implant 28600 includes an expandable member 28670 (also referred to as an "outer shell"), a distal hub member 28612, a base member 28613 and a support member 28672. Similar to the previous embodiment (implant 28300) the implant 28600 also includes an elongate member 28611 having a threaded portion 29608 and a proximal end portion 28607 configured to be engaged by a tool, such as a medical screw driver.

The expandable member 28670 can be formed similar to the outer shell 6670 illustrated and described with reference to FIGS. 19-31. For example, the expandable member 28670 can define a series of openings (not shown) disposed between a distal portion 28616 and a central portion 28618, and between a proximal portion 28614 and the central portion 28618. The expandable member 28670 can also include a series of tabs (not sown) similar to that described for outer shell 6670. The expandable member 28670 also includes expandable portions 28640, which form extensions 28642 (shown in FIG. 103) that extend radially from the expandable member 28670 when the implant 28600 is in the expanded configuration. The expandable member 28670 can have a variety of different shapes, sizes and arrangements as described above for outer shell 6670.

When the implant 28600 is in the collapsed configuration, the expandable portions 28640 can be contoured (not shown in FIG. 102) to extend slightly radially from remaining portions of the expandable member 28870. The expandable portions 28640 can be biased such that when a compressive force is applied, the expandable portions 28640 will extend outwardly from the expandable member 28670 and form extensions 28642. The expandable portions 28640 can be biased using any suitable mechanism. In some embodiments, for example, the expandable portions can be biased by including a notch in one or more locations along the expandable portion, as previously described. In other embodiments, the expandable portions can be biased by varying the thickness of the expandable portions in an axial direction. In yet other embodiments, the expandable portions can be stressed or bent prior to insertion such that the expandable portions are predisposed to extend outwardly when a compressive force is applied to the implant. In such embodiments, the radius of the expandable portions may be greater than that of the remaining portions of the implant (e.g., the remaining cylindrical portions of the implant).

The support member 28672 is disposed within a lumen 28658 defined by the expandable member 28670. The support member 28672 is configured to help maintain the shape of the implant 28600 during insertion, and help prevent the expandable portions 28640 from extending inwardly into an interior region 28658 of the expandable member 28670 during deployment, and/or help maintain the shape of the central portion 28616 after the implant 28600 is in its desired position (e.g., between adjacent spinous processes). The support member 28672 can provide additional structural support to the expandable member 28670 (e.g., in a direction transverse to an axial direction) when the implant 28600. The support member 28672 can also be formed to provide increased compressive strength to the expandable member 28670. This can increase the amount of compressive force that can be applied to the implant 28600 when moving the implant 28600 from the collapsed configuration to the expanded configuration as described in more detailed below. The support member 28672 can be formed, for example, with various materials, such as polymers, elastic materials, flexible plastic or metallic materials, or substantially rigid plastic or metallic materials.

The expandable member 28670 can be formed with various biocompatible materials that provide flexibility such as various elastic metals or plastics, such as Nitinol. An expandable member 28670 formed, for example, with Nitinol, can provide flexibility and allow the expandable member 28670 to be repeatedly moved between a collapsed configuration (FIG. 102) and an expanded configuration (FIG. 103). The support member 28672, the distal hub member 28612, and the base 28613 can each be formed with various biocompatible metal or plastic materials, for example, a titanium or PEEK material. In some embodiments, the support member 28672 can be formed with a flexible material, such as a polymer.

As shown in FIGS. 102 and 103, the support member 28672 in this embodiment is sized such that a radial gap 28660 is defined between the expandable member 28670 and the support member 28672. The gap 28660 can accommodate for more flexibility or deformation of the expandable member 28670 than if the support member 28672 contacts the interior walls of the expandable member 28670. In some embodiments, however, it may be desirable to have the support member 28672 contact the interior walls of the expandable member 28670 without a gap. The support member 28672 can have a solid construction (as shown) or alternatively can define a lumen (not shown).

The support member 28672 is coupled to the distal hub member 28612 and/or the elongate member 28611 such that the support member 28672 can move with the distal hub member 28612 when the implant 28600 is moved between the collapsed configuration and the expanded configuration, as described in more detail below. The support member 28672 can be coupled to the distal hub member 28612 with, for example, an adhesive, a snap fit connection, with one or more fastener(s), with a threaded connection or other suitable coupling methods. In some embodiments without a gap 28660, the support member 28672 is also attached to the expandable member 28670, with for example, an adhesive. In some embodiments, without a gap, the support member 28672 is coupled to the expandable member 28670 with a friction fit. The distal hub member 28612 is also coupled to the expandable member 28670 with, for example, an adhesive.

Similar to the previous embodiment (implant 28300), the elongate member 28611 extends through a lumen defined by the base member 28613 and a lumen of the support member

28672. The distal hub member 28612 defines a lumen 28610 having threaded interior walls configured to matingly (e.g., threadedly) engage a distal end portion of the elongate member 28611. In this embodiment, the elongate member 28611 includes threads along substantially the entire length of the elongate member 28611. It should be understood, however, that the elongate member 28611 can include only a portion with threads as described previously (see, e.g., FIG. 101).

The implant 28600 can be moved between the collapsed configuration, in which the distal hub member 28612 is in a first position (FIG. 102), and the expanded configuration, in which the distal hub member 28612 is in a second position (FIG. 103), in similar manner as described above for implant 28300. For example, when the elongate member 28611 is rotated in a first direction, the distal hub member 28612 is drawn proximally along the elongate member 28611 and exerts an axial force on the support member 28672 and the expandable member 28670. The axial force exerted on the expandable member 28670 will cause the expandable portions 28640 of the expandable member 28670 to be moved to an expanded configuration, as shown in FIG. 103, forming radial extensions 28642. The implant 28600 can be moved back to the collapsed configuration by rotating the elongate member 28611 in an opposite direction such that the distal hub member 28612 is moved distally from the second position back to the first position. As the distal hub member 28612 is moved back to the first position, the expandable member 28670 unfolds back to a collapsed configuration.

In some embodiments, when the elongate member 28611 is rotated to move the implant 28600 to the expanded configuration, the distal hub member 28612 moves proximally toward the base member 28613 and the base member 28613 moves distally toward the distal hub member 28612. In some embodiments, the base member 28613 moves distally and the distal hub member 28612 does not move.

The extensions 28642 of the expandable member 28670 can be a variety of different shapes and sizes depending on the particular desired application of the implant 28600. When in the expanded configuration, the extensions 28642 of the expandable member 28670 have a size (e.g., outer perimeter or diameter in relation to a longitudinal axis of the implant) that is greater than a size (e.g., outer perimeter or diameter in relation to a longitudinal axis of the implant) of the support member 28672. Thus, the extensions 28642 can be used to retain the implant 28600 in a desired position within a patient's body. For example, as with other embodiments described herein, the implant 28600 can be inserted into a patient's body while in a collapsed configuration such that the center portion 28618 of the expandable member 28670 and the support member 28672 are positioned in a space between adjacent spinous processes. The implant 28600 can then be moved to the expanded configuration as described above. The extensions 28642 of the expandable member 28670 can be sized such that when in the expanded configuration, the extensions 28642 of the expandable member 28670 prevent or limit lateral movement of the implant 28600 and maintain the position of the support member 28372 between the adjacent spinous processes.

As described above for implant 28300, in some embodiments, an implant 28600 can be configured with an elongate member that is actuated through axial motion, rather than rotational motion. For example, an elongate member can be configured to be releasably coupled to the distal hub member in a similar manner as shown and described with reference to implant 6610. An expansion tool (e.g., tool 1500 or 7500) can be used to exert an axial force on the distal hub member by pulling the elongate member proximally (exerting a proximal force on the elongate member). This will in turn compress (elastically deform) the first expandable member and the second expandable member and move them to their expanded configuration. The tool can be actuated in an opposite direction (applying an axial force on the elongate member in a distal direction) to move the first expandable member and the second expandable member back to the collapsed configuration.

The various implants and deployment/insertion tools described herein can be constructed with various biocompatible materials such as, for example, titanium, titanium alloyed, surgical steel, biocompatible metal alloys, stainless steel, Nitinol, plastic, polyetheretherketone (PEEK), carbon fiber, ultra-high molecular weight (UHMW) polyethylene, biocompatible polymeric materials, etc. The material of a central portion of the implant can have, for example, a compressive strength similar to or higher than that of bone. In one embodiment, the central portion of the implant, which is placed between the two adjacent spinous processes, is configured with a material having an elastic modulus higher than the elastic modulus of the bone, which forms the spinous processes. In another embodiment, the central portion of the implant is configured with a material having a higher elastic modulus than the materials used to configure the distal and proximal portions of the implant. For example, the central portion of the implant may have an elastic modulus higher than bone, while the proximal and distal portions have a lower elastic modulus than bone. In yet another embodiment, where the implant is configured with an outer shell and an inner core. The outer shell (e.g., can be configured with material having a higher elastic modulus than the inner core (e.g., outer shell 6670, expandable member 28670) can be made with, for example, a titanium alloyed material or Nitinol, while the inner core (e.g., inner core 6672 or support member 28672) can be made with a polymeric material). Alternatively, the outer shell can be configured with a material having a lower elastic modulus than the inner core (e.g., the outer shell is made with a polymeric material while the inner core is made with a titanium alloyed material).

While various embodiments of the invention have been described above, it should be understood that they have been presented by way of example only, and not limitation. Where methods and steps described above indicate certain events occurring in certain order, those of ordinary skill in the art having the benefit of this disclosure would recognize that the ordering of certain steps may be modified and that such modifications are in accordance with the variations of the invention. Additionally, certain of the steps may be performed concurrently in a parallel process when possible, as well as performed sequentially as described above. Thus, the breadth and scope of the invention should not be limited by any of the above-described embodiments, but should be defined only in accordance with the following claims and their equivalents. While the invention has been particularly shown and described with reference to specific embodiments thereof, it will be understood that various changes in form and details may be made.

For example, although the embodiments above are primarily described as being spinal implants configured to be positioned in a space between adjacent spinous processes, in alternative embodiments, the implants are configured to be positioned adjacent any bone, tissue or other bodily structure where it is desirable to maintain spacing while preventing axial or longitudinal movement of the implant.

Although the medical devices are shown and described as including an implant and/or a deployment tool, in some embodiments a kit can include any number of implants and/or any number of deployment tools as described above. For example, a kit can include an implant and two deployment tools, one deployment tool configured to be used to move the implant from a collapsed configuration to an expanded configuration, and another deployment tool configured to be used to move the implant from the expanded configuration to the collapsed configuration. Alternatively, a kit can include a single deployment tool have multiple engaging portions as described herein, that can be releasably coupled to an implant. For example, one type or style of engaging portion can be used to move the implant from a collapsed configuration to an expanded configuration, and another type or style of engaging portion can be used to move the implant from the expanded configuration to the collapsed configuration. The kit can include engaging portions having one of a variety of different shapes and sizes, such that a user can select a particular engaging portion(s) for use in a particular application.

Similarly, although various embodiments have been described as having particular features and/or combinations of components, other embodiments are possible having a combination or sub-combination of any features and/or components from any of embodiments as discussed above. For example, the implant 6610 can be configured to be actuated with a threaded elongate member, such as elongate members 28311 or 28611. In another example, the implants 28300 and 28600 can be configured to be actuated with a such as insertion tools 7500 or 1500.

Although various implants have been shown and described above as having a first configuration and a second configuration (e.g., a collapsed configuration and an expanded configuration), in some embodiments, an implant can include three or more configurations. For example, in some embodiments, an implant can have a first configuration, in which the implant can be inserted between the spinous processes unimpeded by a retention member of the implant, a second configuration, in which lateral movement of the implant is limited by the retention member and a third configuration in which the implant can move in one lateral direction, but not the other.

Similarly, in some embodiments, a deployment tool, an expansion device and/or an insertion tool can be configured to perform any combination of functions described herein. For example, in some embodiments, a deployment tool, an expansion device and/or an insertion tool can be configured to insert a spinal implant into a body, move a spinal implant between a retracted configuration and an expanded configuration within a body, reposition a spinal implant within the body and/or remove a spinal implant within the body. In some embodiments, a deployment tool, an expansion device and/or an insertion tool can be configured to perform only a single function, such as, for example, removing a spinal implant from the body. In other embodiments, a kit can include a deployment tool, an expansion device and/or an insertion tool along with various implements so that the deployment tool, expansion device and/or insertion tool can be re-configured to perform any combination of functions described herein.

What is claimed is:

1. A method, comprising:
disposing at least a portion of a support member into a space between adjacent spinous processes, the support member having a central portion of the support member and defining a lumen extending from a proximal exterior endface of the support member to a distal exterior endface of the support member, the support member having a noncontiguous outer surface and includes a first portion having a first end and a second end and a second portion being separate from the first portion, the second portion having a first end and a second end, a hinge pivotally coupling the first end of the first portion to the first end of the second portion, a gap formed between the second end of the first portion and the second end of the second portion, inserting an expandable member through the lumen of the support member such that a distal end portion of the expandable member is disposed outside a distal end of the lumen of the support member and a proximal end portion of the expandable member is disposed outside a proximal end of the lumen of the support member, the expandable member includes a central portion between the distal end portion of the expandable member and the proximal end portion of the expandable member;

after the disposing and the inserting and while the lumen extends transversely through a sagittal plane defined by the spinous processes and the expandable member is in contact with the lumen along substantially the entire length thereof, expanding the distal end portion of the expandable member and the proximal end portion of the expandable member by injecting a medium into an interior of the expandable member such that:

each of the distal end portion of the expandable member and the proximal end portion of the expandable member has an outer diameter greater than an outer diameter of the support member;

the distal end portion of the expandable member extends more distally than the support member and is disposed on a first lateral side of the sagittal plane; and the proximal end portion of the expandable member extends more proximally than the support member and is disposed on an opposite lateral side of the sagittal plane;

the central portion of the support member expands such that the first portion of the support member moves relative to the second portion of the support member about the hinge and the adjacent spinous processes are distracted;

during the expanding the central portion of the support member expands such that the first portion of the support member moves relative to and away from the second portion of the support member such that the gap increases in size;

wherein a longitudinal length of the support member is substantially the same the prior to the expanding of the expandable member and after the expanding of the expandable member, the longitudinal length extending from the distal end of the support member to the proximal end of the support member;

wherein, prior to the expanding of the expandable member, the support member extends farther outward radially with respect to a longitudinal axis of the lumen than both the distal and proximal end portions of the expandable member.

2. The method of claim 1, wherein the disposing includes disposing the support member at a first location within a space between adjacent spinous processes, the method further comprising:

after the expanding, collapsing the distal end portion of the expandable member and the proximal end portion of the expandable member; and disposing the support member at a second location within the space between adjacent spinous processes, the second location being different than the first location.

3. The method of claim 1, further comprising:

after the expanding, collapsing the distal end portion of the expandable member and the proximal end portion of the expandable member; and removing the expandable member from the support member.

4. The method of claim 1, further comprising:
after the expanding, collapsing the distal end portion of the expandable member and the proximal end portion of the expandable member;
removing the expandable member from the support member; and
after the removing, removing the support member from the space between the adjacent spinous processes.

5. The method of claim 1, wherein the inserting the expandable member is after the disposing.

6. The method of claim 1:
wherein the expanding comprises moving, in response to said injecting, the first portion of the support member and the second portion of the support member from a collapsed configuration to an expanded configuration.

7. The method of claim 6, further comprising:
prior to the disposing, inserting a guide wire into the space between adjacent spinous processes,
the disposing includes passing the support member of the spinal implant over the guidewire via the lumen of the support member.

8. The method of claim 6, further comprising:
after the expanding, collapsing the distal end portion of the expandable member and the proximal end portion of the expandable member;
after the collapsing, removing the expandable member from the support member while the support member is at least partially disposed in the space between the adjacent spinous processes; and
after the removing, of the expandable member removing the support member from the space between the adjacent spinous processes.

9. The method of claim 6, wherein the disposing includes disposing the support member at a first location within a space between adjacent spinous processes, the method further comprising:
after the expanding, collapsing the distal end portion of the expandable member and the proximal end portion of the expandable member; and
disposing the support member at a second location within the space between adjacent spinous processes, the second location being different than the first location.

10. The method of claim 6 wherein the moving the first portion of the support member and the second portion of the support member from the collapsed configuration to the expanded configuration comprises rotating the first portion of the support member relative to the second portion of the support member about the hinge that interconnects the first and second portions of the support member.

* * * * *